US012215108B2

(12) United States Patent
Suto et al.

(10) Patent No.: US 12,215,108 B2
(45) Date of Patent: Feb. 4, 2025

(54) DEVELOPMENT OF POTENTIAL ANTIDOTES FOR ARSENICALS

(71) Applicants: Southern Research Institute, Birmingham, AL (US); UAB Research Foundation, Birmingham, AL (US); The United States Government as represented by the Department of Veterans Affairs, Washington, DC (US)

(72) Inventors: Mark J. Suto, Homewood, AL (US); Bini Mathew, Hoover, AL (US); Corinne E. Augelli-Szafran, Homewood, AL (US); Marina Fosso Yatchang, Chelsea, AL (US); Mohammad Athar, Hoover, AL (US); Anupam Agarwal, Mountain Brook, AL (US); Ritesh Kumar Srivastava, Vestavial Hills, AL (US); Suhail Muzaffar, Birmingham, AL (US); Jasim Khan, Birmingham, AL (US)

(73) Assignees: Southern Research Institute, Birmingham, AL (US); UAB Research Foundation, Birmingham, AL (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 18/095,429

(22) Filed: Jan. 10, 2023

(65) Prior Publication Data

US 2023/0219958 A1     Jul. 13, 2023

Related U.S. Application Data

(60) Provisional application No. 63/298,162, filed on Jan. 10, 2022.

(51) Int. Cl.
   C07D 473/32    (2006.01)
   A61P 39/02     (2006.01)

(52) U.S. Cl.
   CPC ........... *C07D 473/32* (2013.01); *A61P 39/02* (2018.01)

(58) Field of Classification Search
   CPC .................................................. C07D 473/32
   See application file for complete search history.

(56) References Cited

U.S. PATENT DOCUMENTS 9,725,450 B2    8/2017  Clareen et al.

FOREIGN PATENT DOCUMENTS

| CN | 104250250 | 12/2014 |
|----|-----------|---------|
| CN | 112759594 | 5/2021 |
| WO | WO 98/35048 | 8/1998 |
| WO | WO 2000/042042 | 7/2000 |
| WO | WO 2006/076595 | * 7/2006 |
| WO | WO 2008/039359 | 4/2008 |
| WO | WO 2016/061144 A1 | 4/2016 |
| WO | WO 2018/208132 | 11/2018 |
| WO | WO 2019/204399 A1 | 10/2019 |

OTHER PUBLICATIONS

Jun et al. (2021) "Discovery of a Potent and Selective JNK3 Inhibitor with Neuroprotective Effect Against Amyloid β-Induced Neurotoxicity in Primary Rat Neurons," *International Journal of Molecular Sciences* 22: 1-17.

Picaud et al. (2015) "9H-purine scaffold reveals induced-fit pocket plasticity of the BRD9 bromodomain," *Journal of Medicinal Chemistry* 58: 2718-2736.

* cited by examiner

*Primary Examiner* — Marcos L Sznaidman
(74) *Attorney, Agent, or Firm* — Ballard Spahr LLP

(57) ABSTRACT

The present disclosure is concerned with purine diamine compounds for the treatment of conditions associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters. This abstract is intended as a scanning tool for purposes of searching in the particular art and is not intended to be limiting of the present invention.

15 Claims, 11 Drawing Sheets

DEVELOPMENT OF POTENTIAL ANTIDOTES FOR ARSENICALS

CROSS-REFERENCE TO RELATED APPLICATIONS

This application claims the benefit of U.S. Application No. 63/298,162, filed on Jan. 10, 2022, the contents of which are incorporated herein by reference in their entirety.

STATEMENT REGARDING FEDERALLY SPONSORED RESEARCH

This invention was made with government support under grant number U54 ES030246 awarded by the National Institutes of Health-U54 (NIH-U54) Program. The government has certain rights in the invention.

BACKGROUND

Globally, millions of people are at risk for the adverse effects of arsenic exposure. The majority of harmful arsenic exposure comes from drinking water from wells drilled through arsenic-bearing sediments. Drinking water contains primarily inorganic arsenic, which is more acutely toxic than the organic form. The other major sources of arsenic exposure are through food, soil, and air. For most people, in fact, the primary exposure to arsenic comes from food, but dietary arsenic includes primarily organic forms, which are relatively nontoxic and contribute little, if any, to the overall risk associated with exposure.

Cutaneous arsenic exposure places people at risk for a host of adverse health effects, from skin and internal cancers (of the bladder, kidney, liver, lung, colon, uterus, prostate, and stomach) to diabetes mellitus and vascular, reproductive, developmental, and neurological effects. Noncancerous effects of arsenic arise from both acute and chronic exposures. Among those symptoms linked with acute exposure to arsenic-laced well water (typically containing more than 1,200 micrograms per liter (μg/L)) are abdominal pain, vomiting, diarrhea, muscular weakness and cramping, pain to the extremities, erythematous skin eruptions, and swelling of the eyelids, feet, and hands. A progressive deterioration in the motor and sensory responses may also result, finally leading to shock and death. The effects of chronic arsenic poisoning (also called arsenicosis) are more complex. Aside from cancer, these chronic effects include dysfunction of systemic organs, atherosclerosis, diabetes, hypertension, anemia, liver disorders, kidney damage, headache, confusion, peripheral neuropathy, and a variety of skin lesions, notably hyperkeratosis, or thickening of the skin, and both hypo- and hyperpigmentation.

Despite the widespread prevalence of arsenic exposure, and the wide range of conditions associated therewith, methods of treating arsenic poisoning have remaind elusive. Thus, there remains a need for compounds and compositions for treating conditions associated with arsenic exposure, and methods of making and using same.

SUMMARY

In accordance with the purpose(s) of the invention, as embodied and broadly described herein, the invention, in one aspect, relates to compounds and compositions for use in the prevention and treatment of conditions associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters.

Thus, disclosed are compounds having a structure represented by a formula:

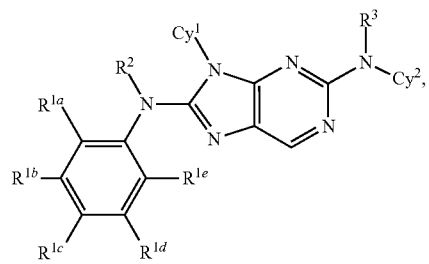

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein $Cy^1$ is a structure having a formula selected from:

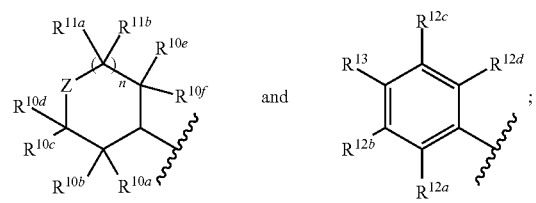

wherein n, when present, is 0 or 1; wherein Z, when present, is selected from —O—, —S—, and —NR$^{20}$—; wherein $R^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein $Cy^2$ is a structure having a formula selected from:

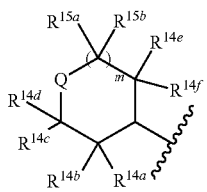 and 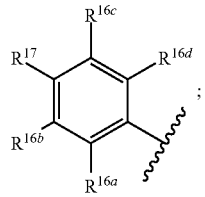 ;

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of R$^{14a}$, R$^{14b}$, R$^{14c}$, R$^{14d}$, R$^{14e}$, and R$^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{15a}$ and R$^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$, R$^{16b}$, R$^{16c}$, and R$^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when Cy$^1$ is

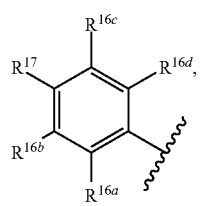

and at least seven of R$^{10a}$, R$^{10b}$, R$^{1c}$, R$^{10d}$, R$^{10e}$, R$^{10f}$, R$^{11a}$, and R$^{11b}$ are hydrogen, and when Cy$^2$ is

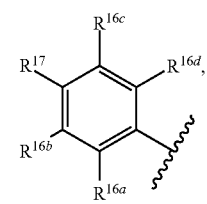

then either: (a) each of R$^{1a}$, R$^{1b}$, R$^{1c}$, and R$^{1e}$ is halogen; or (b) Z is —O—, each of R$^{16a}$, R$^{16b}$, R$^{16c}$, and R$^{16d}$ is hydrogen, and R$^{17}$ is —OH, —NH$_2$, C1-C4 alkoxy, C1-C4 alkylamino, or (C1-C4)(C1-C4) dialkylamino, provided that when Cy$^1$ is

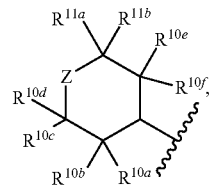

then Cy$^2$ is

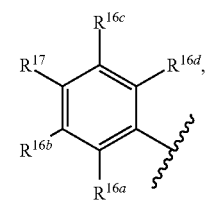

provided that when Cy$^1$ is and Cy$^2$ is

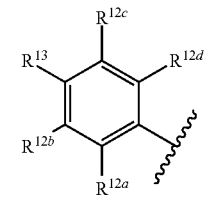

then R$^{17}$ is a non-hydrogen group, and provided that when Cy$^1$ is

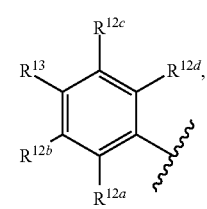

Cy² is

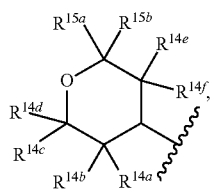

and at least seven of $R^{14a}$, $R^{14b}$, $R^{14c}$, $R^{14d}$, $R^{14e}$, $R^{14f}$, $R^{15a}$, and $R^{15b}$ are hydrogen, then each of $R^{12a}$, $R^{12b}$, $R^{12c}$, and $R^{12d}$ is hydrogen, or a pharmaceutically acceptable salt thereof.

Also disclosed are pharmaceutical compositions comprising an effective amount of a disclosed compound, and a pharmaceutically acceptable carrier.

Also disclosed are methods of treating a condition associated with signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure represented by a formula:

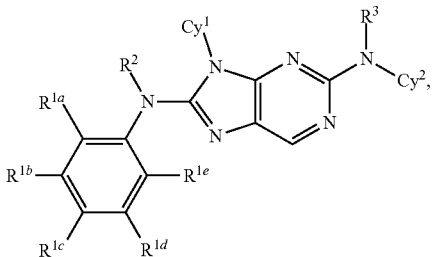

wherein each of $R^{1a}$, $R^{1b}$, $R^{1c}$, $R^{1d}$, and $R^{1e}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy¹ is a structure having a formula selected from:

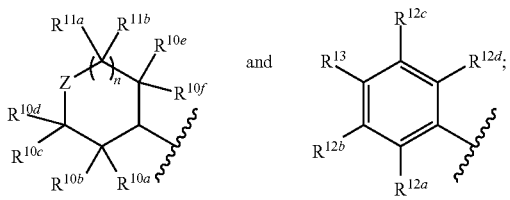

wherein n, when present, is 0 or 1; wherein Z, when present, is selected from —O—, —S—, and —NR²⁰—; wherein $R^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH₂, C1-C4 alkoxy, C1-C4 alkylamino, and (C1-C4)(C1-C4) dialkylamino; and wherein Cy² is a structure having a formula selected from:

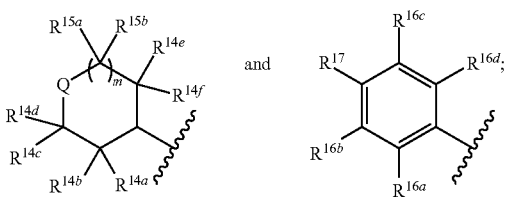

wherein m, when present, is 0 or 1; wherein Q, when present, is selected from —O—, —S—, and —NR²¹—; wherein $R^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO₂H, and —CO₂(C1-C4 alkyl), or a pharmaceutically acceptable salt thereof, thereby treating the condition.

Also disclosed are methods of modifying signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure represented by a formula:

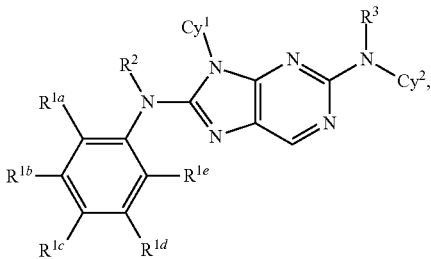

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

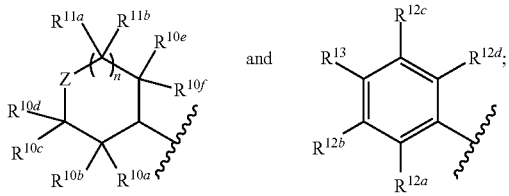

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$ when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

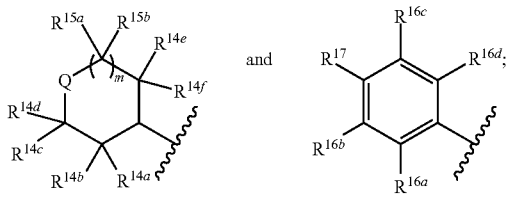

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), or a pharmaceutically acceptable salt thereof, thereby modifying signaling of one or more of BRD4, RIP3K, and IL6.

Also disclosed are methods of modifying signaling of one or more of bromodomain-containing protein 4 (BRD4), receptor-interacting serine/threonine-protein kinase 3 (RIP3K), and interleukin 6 (IL6) in a cell, the method comprising administering to the subject an effective amount of a compound having a structure represented by a formula:

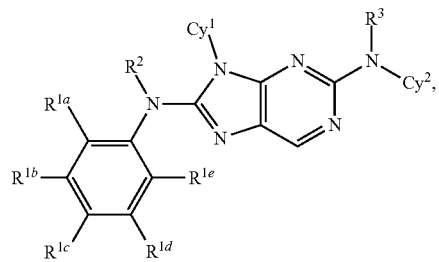

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

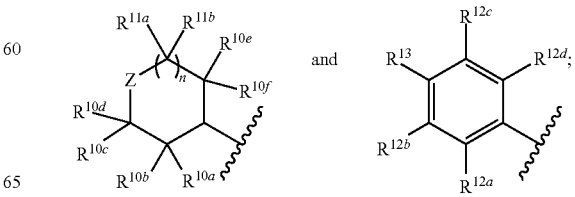

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{11a}$ and R$^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{12a}$, R$^{12b}$, R$^{12c}$, and R$^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

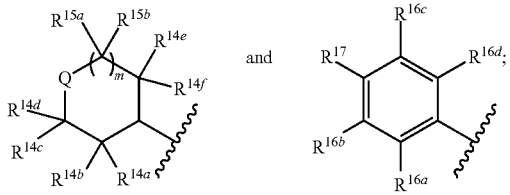

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of R$^{14a}$, R$^{14b}$, R$^{14c}$, R$^{14d}$, R$^{14e}$, and R$^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{15a}$ and R$^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$, R$^{16b}$, R$^{16c}$, and R$^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$ (C1-C4 alkyl), or a pharmaceutically acceptable salt thereof, thereby modifying signaling of one or more of BRD4, RIP3K, and IL6 in the cell.

Also disclosed are kits comprising a compound having a structure represented by a formula:

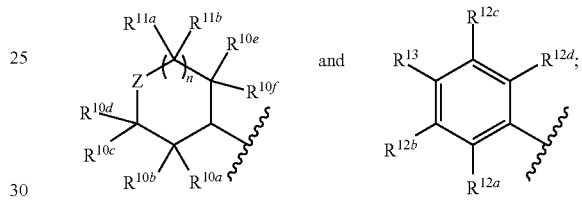

wherein each of R$^{1a}$, R$^{1b}$, R$^{1c}$, R$^{1d}$, and R$^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^2$ and R$^3$ is independently selected from hydrogen and C1-C4 alkyl; wherein Cy$^1$ is a structure having a formula selected from:

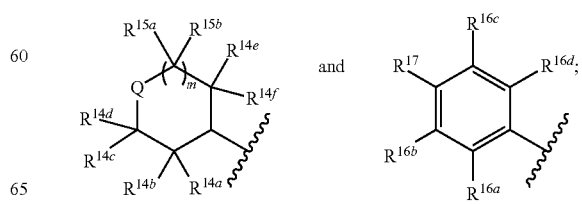

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{11a}$ and R$^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$, R$^{12b}$, R$^{12c}$, and R$^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of R$^{14a}$, R$^{14b}$, R$^{14c}$, R$^{14d}$, R$^{14e}$, and R$^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{15a}$ and R$^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$, R$^{16b}$, R$^{16c}$, and R$^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), or a pharmaceutically acceptable salt thereof, and one or more of: (a) an agent associated with the treatment of a condition associated with BRD4, RIP3K, and/or IL6 signaling dysfunction; (b) instructions for administering the compound in connection with treating a condition associated with BRD4, RIP3K, and/or IL6 signaling dysfunction; and (c) instructions for treating a condition associated with BRD4, RIP3K, and/or IL6 signaling dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings.

FIG. 1C shows a densitometry analysis of western blot band intensity and FIG. 1D shows a RT-PCR analysis of BRD4-regulated inflammatory and tissue damage-related genes in murine skin.

FIG. 2A shows an exposure paradigm in which inhibitors were applied two times post lewisite challenge. First application was made at 30 minute post lewisite and second application was 6 hr post lewisite. Mice photographs are shown illustrating skin gross injury by each treatment group. FIG. 2B shows the effects of compound no. 11 and other BRD4 inhibitors on lewisite-induced skin-bifold thickness and Draize score. FIG. 2C shows a representative histological analysis of skin sections by H&E staining. FIG. 2D shows a representative Western blot analysis of BRD4 and H3/H4 histone acetylation marks. FIG. 2E shows a representative densitometry analysis of western blot band intensity. FIG. 2F shows a representative immunohistochemistry of BRD4 and H3K9ac in the murine skin. FIG. 2G shows a representative Western blot analysis of RIPK signaling protein markers in the skin tissue lysates obtained from indicated treatment groups. FIG. 2H shows a representative densitometry analysis of western blot band intensity. FIGS. 2I and 2J shows representative RT-PCR analysis of BRD4-regulated inflammatory and tissue damage related genes respectively in murine skin.

Figure 1A:
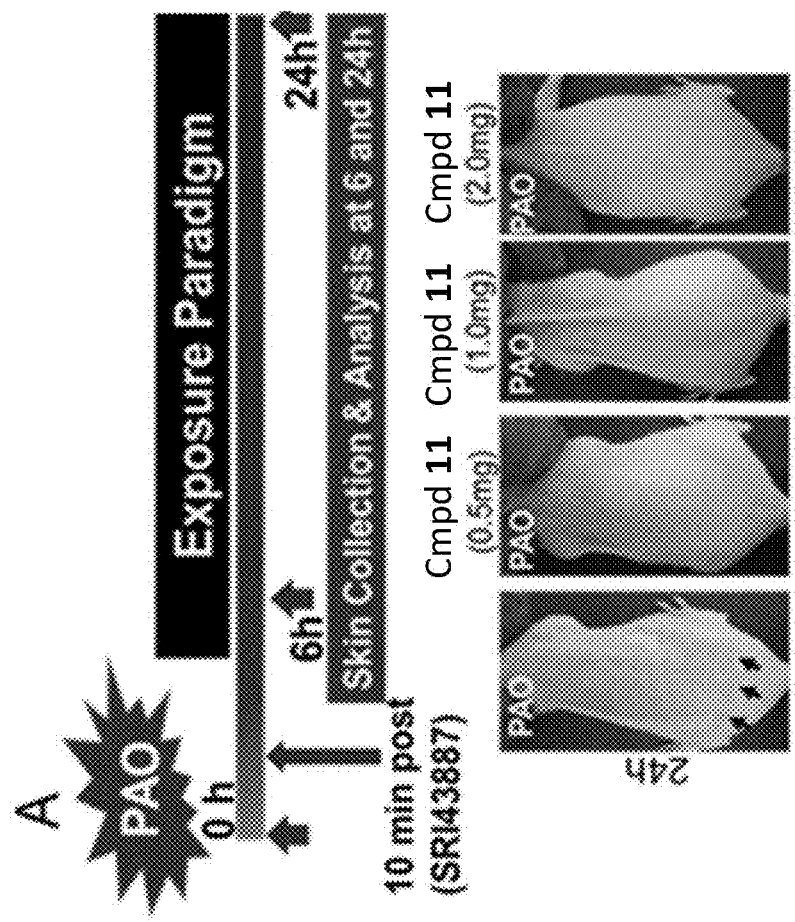
FIG. 1A-D show representative data illustrating the effects of compound no. 11 on PAO-induced skin injury. Specifically, an exposure paradigm is shown in FIG. 1A. A Western Blot analysis of skin tissue lysates from indicated treatment groups is shown in FIG. 1B.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease, disorder, or condition. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the condition being treated and the severity of the condition; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-cancer and anti-neoplastic agents such as kinase inhibitors, poly ADP ribose polymerase (PARP) inhibitors and other DNA damage response modifiers, epigenetic agents such as bromodomain and extra-terminal (BET) inhibitors, histone deacetylase (HDAc) inhibitors, iron chelators and other ribonucleotides reductase inhibitors, proteasome inhibitors and Nedd8-activating enzyme (NAE) inhibitors, mammalian target of rapamycin (mTOR) inhibitors, traditional cytotoxic agents such as paclitaxel, dox, irinotecan, and platinum compounds, immune checkpoint blockade agents such as cytotoxic T lymphocyte antigen-4 (CTLA-4) monoclonal antibody (mAB), programmed cell death protein 1 (PD-1)/programmed cell death-ligand 1 (PD-L1) mAB, cluster of differentiation 47 (CD47) mAB, toll-like receptor (TLR) agonists and other immune modifiers, cell therapeutics such as chimeric antigen receptor T-cell (CAR-T)/chimeric antigen receptor natural killer (CAR-NK) cells, and proteins such as interferons (IFNs), interleukins (ILs), and mAbs; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide" as used herein can be used interchangeably and refer to F, Cl, Br, or I.

The terms "pseudohalide," "pseudohalogen," or "pseudohalo" as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}$-Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, C1-6 aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$-Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

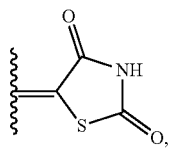

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di-, or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

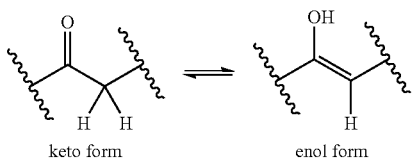

keto form    enol form

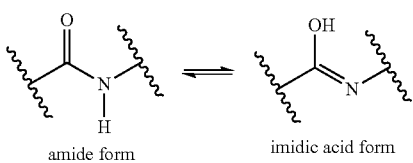

amide form    imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

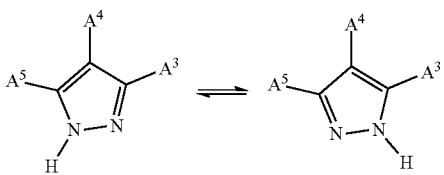

Unless stated to the contrary, the invention includes all such possible tautomers.

It is known that chemical substances form solids, which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

which is understood to be equivalent to a formula:

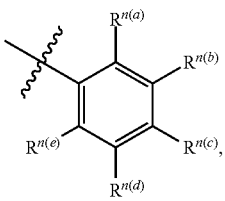

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compounds and compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Purine Diamines

In one aspect, the invention relates to purine diamines useful in preventing and treating conditions associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters.

In one aspect, the compounds of the invention are useful in the treatment of cancer, as further described herein. In one aspect, the compounds of the invention are useful in the treatment of arsenicosis or arsenic poisoning, as further described herein. In one aspect, the compounds of the invention are useful in the treatment of inflammation, skin lesions, dysfunction of systemic organs, and/or skin blisters, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

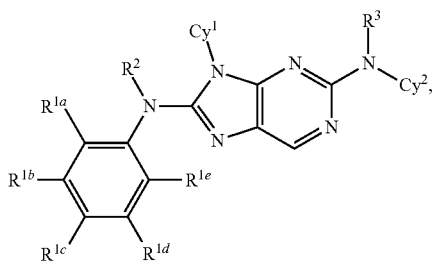

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

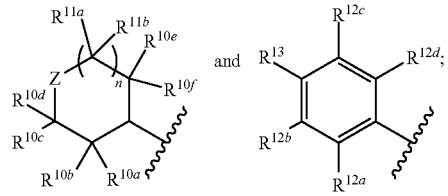

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

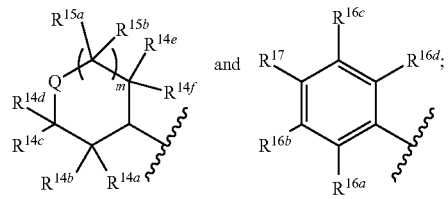

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), provided that when Cy$^1$ is

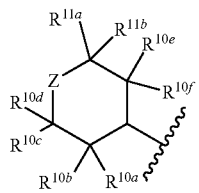

and at least seven of $R^{10a}$, $R^{10b}$, $R^{10c}$, $R^{10d}$, $R^{10e}$, $R^{10f}$, $R^{11a}$, and $R^{11b}$ are hydrogen, and when Cy$^2$ is

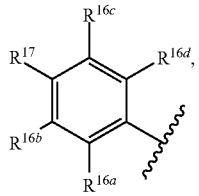

then either: (a) each of $R^{1a}$, $R^{1c}$, and $R^{1e}$ is halogen; or (b) Z is —O—, each of $R^{16a}$, $R^{16b}$, $R^{16c}$, and $R^{16d}$ is hydrogen, and $R^{17}$ is —OH, —NH$_2$, C1-C4 alkoxy, C1-C4 alkylamino, or (C1-C4)(C1-C4) dialkylamino, provided that when Cy$^1$ is

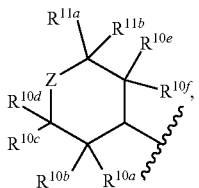

then Cy$^2$ is

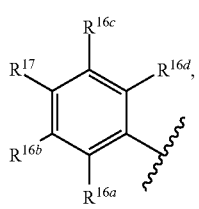

provided that when Cy$^1$ is

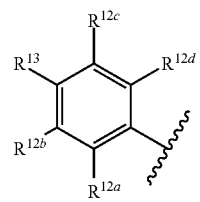

and Cy$^2$ is

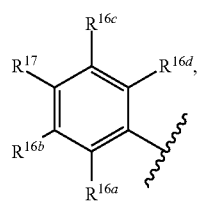

then $R^{17}$ is a non-hydrogen group, and provided that when Cy$^1$ is

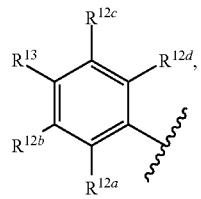

Cy$^2$ is

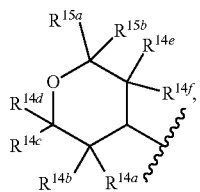

and at least seven of $R^{14a}$, $R^{14b}$, $R^{14c}$, $R^{14d}$, $R^{14e}$, $R^{14f}$, $R^{15a}$, and $R^{15b}$ are hydrogen, then each of $R^{12a}$, $R^{12b}$, $R^{12c}$ and $R^{12d}$ is hydrogen, or a pharmaceutically acceptable salt thereof.

In various aspects, the compound has a structure represented by a formula:

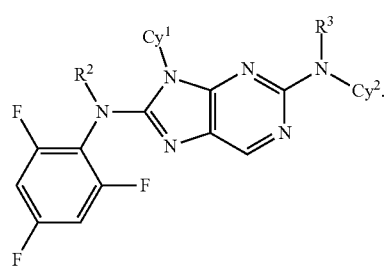

In various aspects, the compound has a structure represented by a formula:

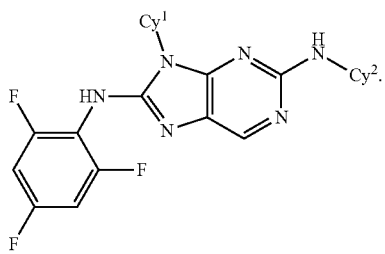

In various aspects, the compound has a structure represented by a formula:

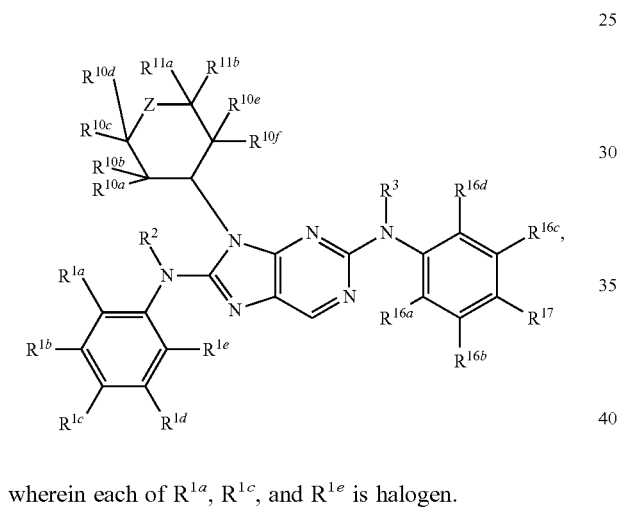

wherein each of $R^{1a}$, $R^{1c}$, and $R^{1e}$ is halogen.

In various aspects, the compound has a structure represented by a formula:

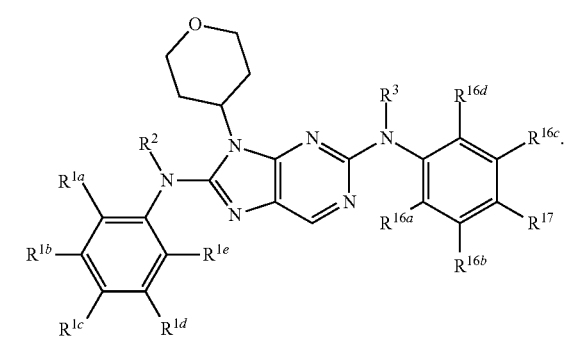

In various aspects, the compound has a structure represented by a formula:

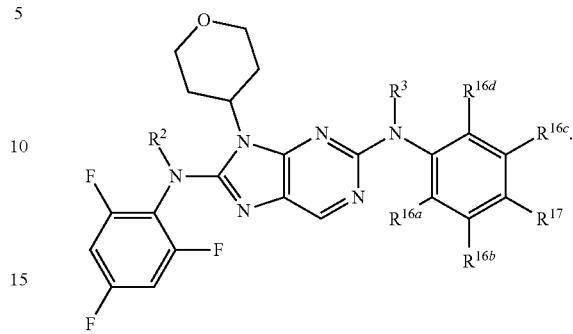

In various aspects, the compound has a structure represented by a formula:

wherein $R^{17}$ is selected from —OH, —NH$_2$, C1-C4 alkoxy, C1-C4 alkylamino, and (C1-C4)(C1-C4) dialkylamino.

In various aspects, the compound has a structure represented by a formula:

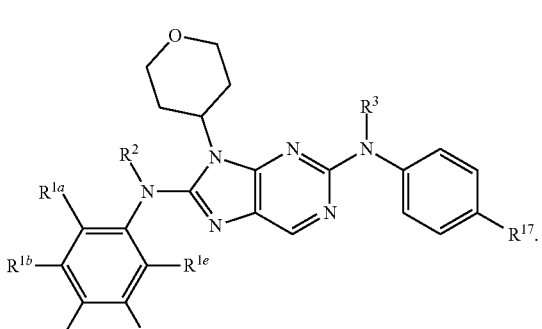

In various aspects, the compound has a structure represented by a formula:

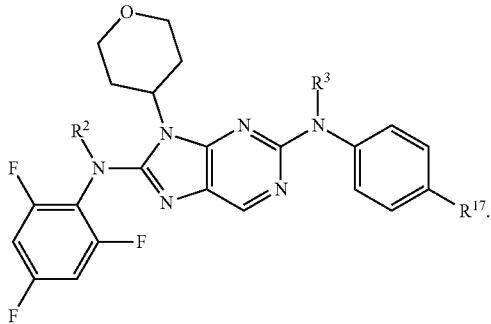

In various aspects, the compound has a structure represented by a formula:

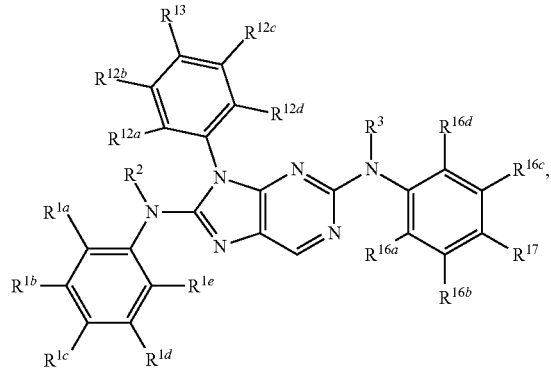

wherein $R^{17}$, when present, is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl).

In various aspects, the compound has a structure represented by a formula:

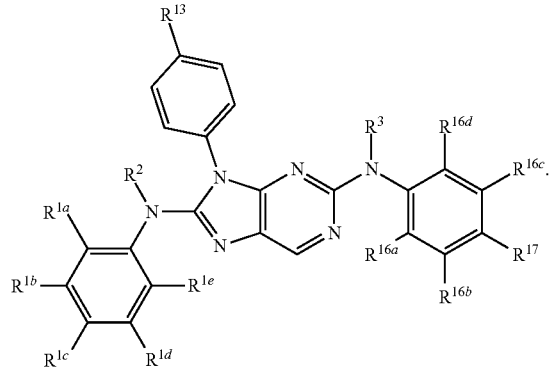

In various aspects, the compound has a structure represented by a formula:

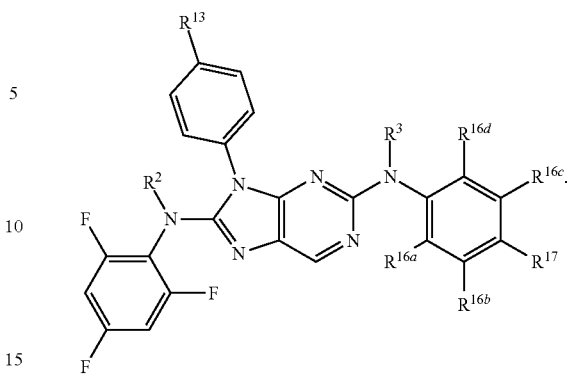

In various aspects, the compound has a structure represented by a formula:

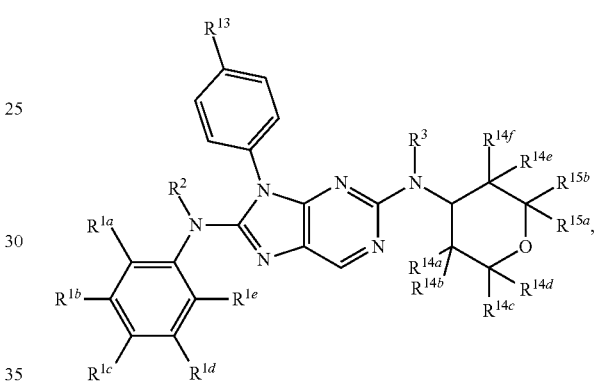

wherein one of $R^{14a}$, $R^{14b}$, $R^{14c}$, $R^{14d}$, $R^{14e}$, $R^{14f}$, $R^{15a}$, and $R^{15b}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein the remaining $R^{14a}$, $R^{14b}$, $R^{14c}$, $R^{14d}$, $R^{14e}$, $R^{14f}$, $R^{15a}$, and $R^{15b}$ groups are hydrogen.

In various aspects, the compound has a structure represented by a formula:

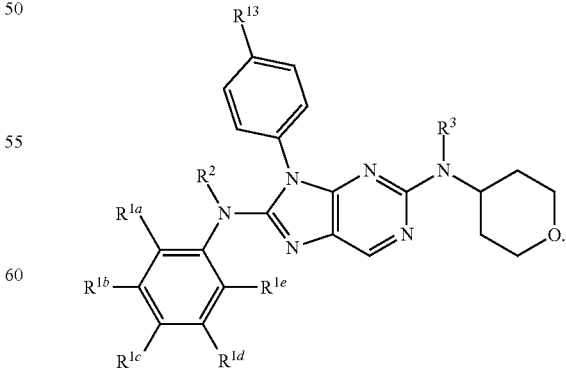

In various aspects, the compound has a structure represented by a formula:

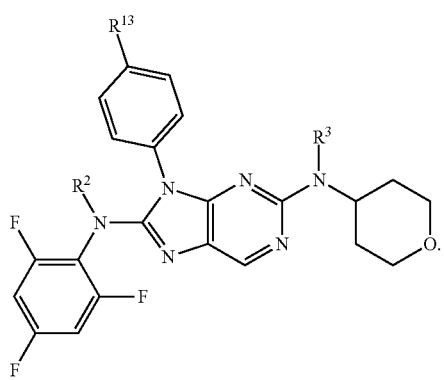
In various aspects, the compound is selected from:
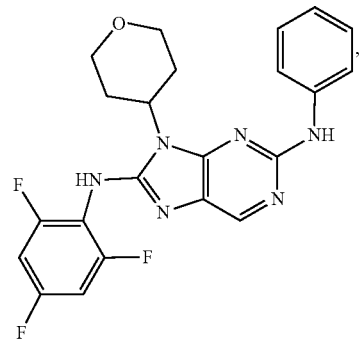
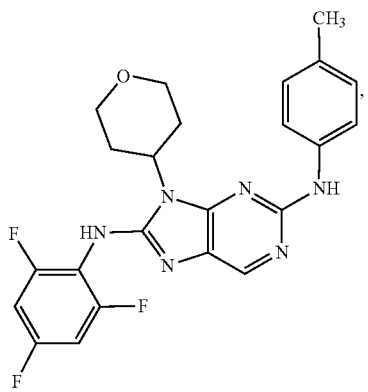
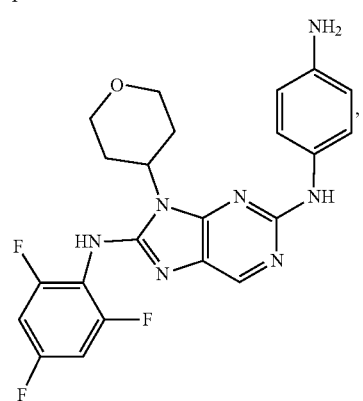
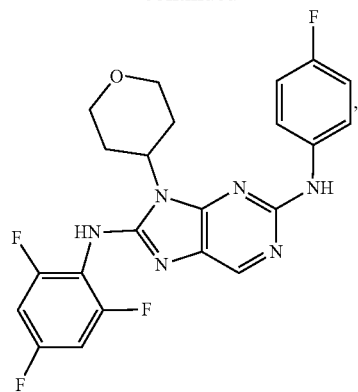
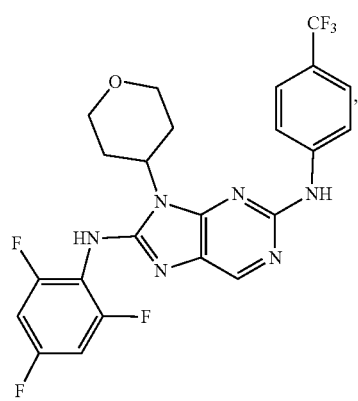
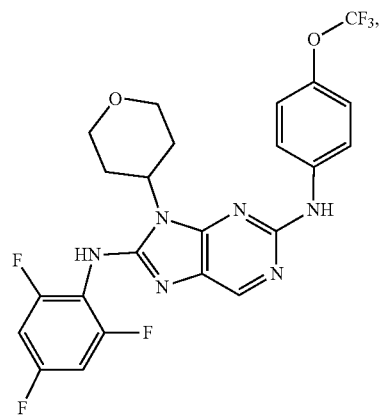
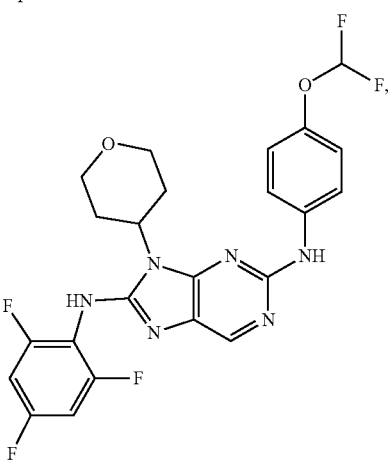

-continued
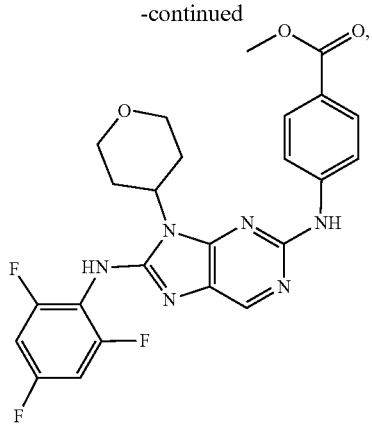
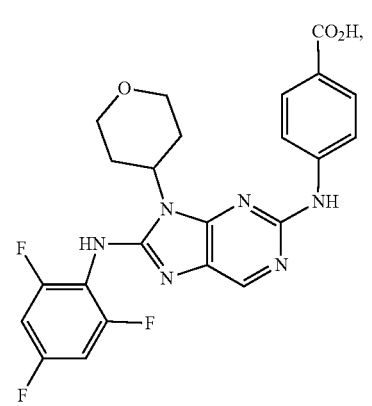
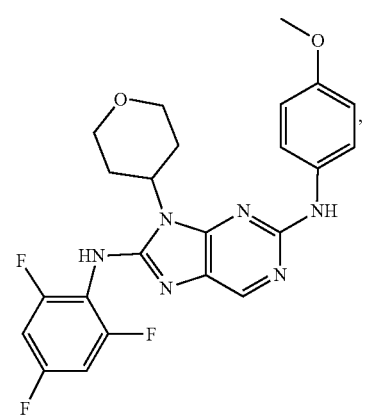
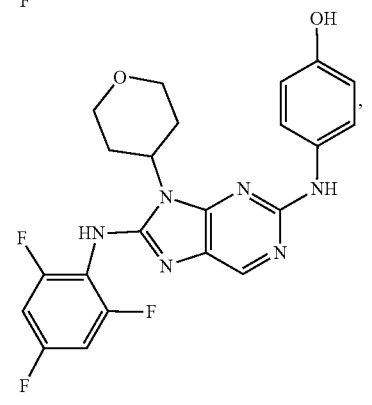
-continued
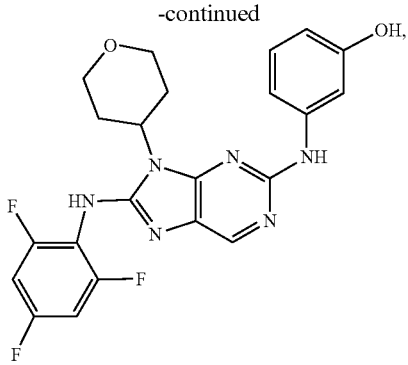
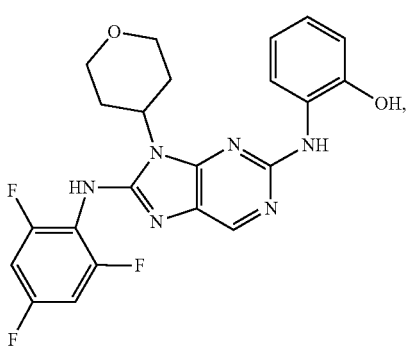
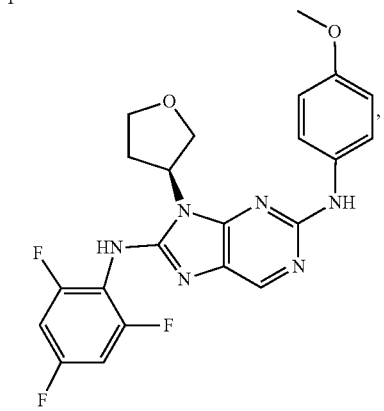
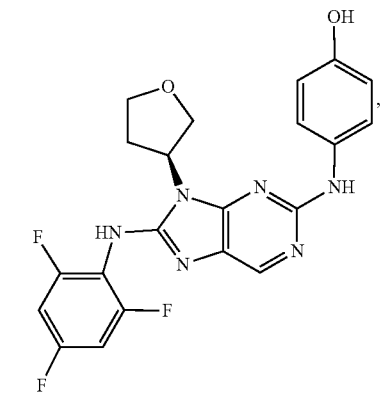

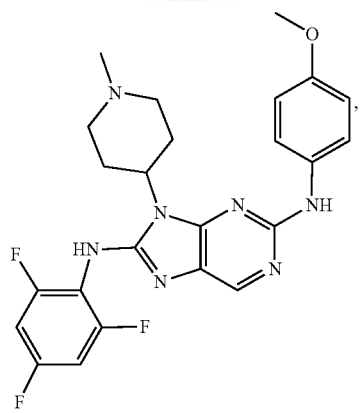
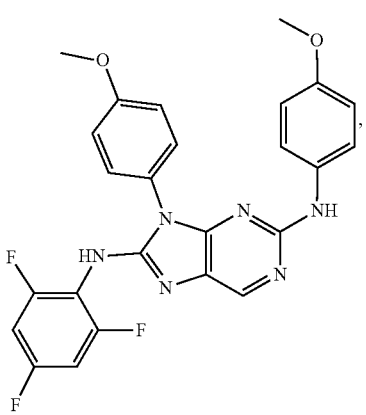
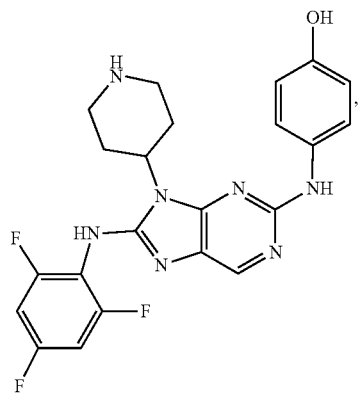
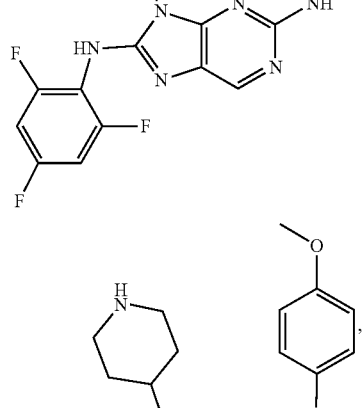
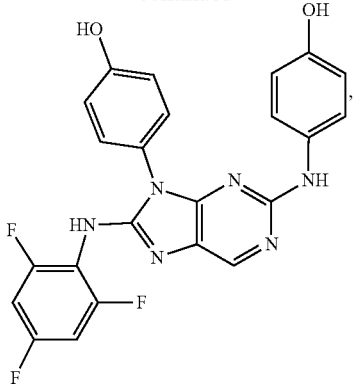
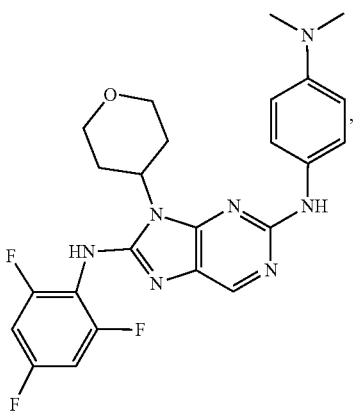
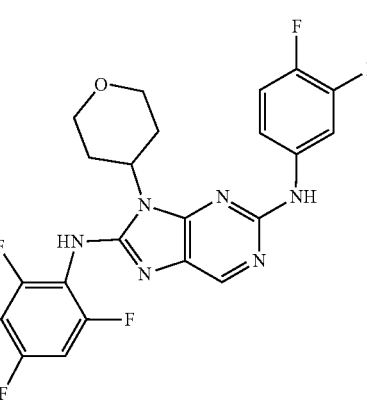
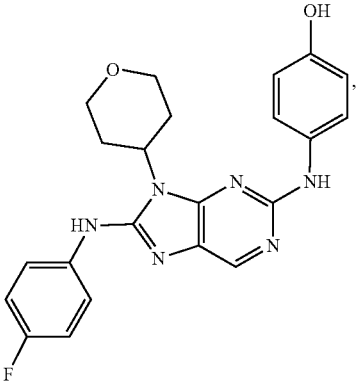

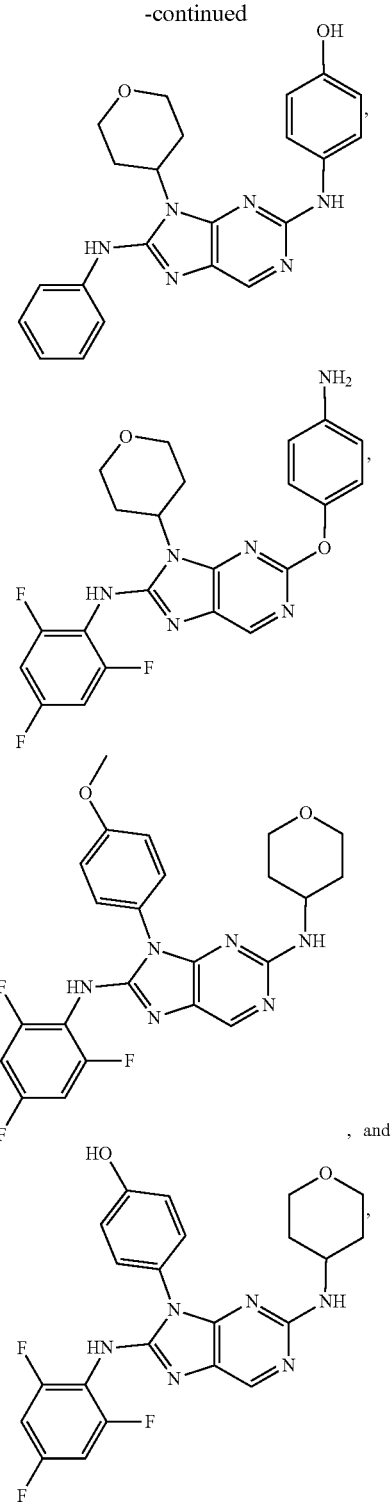

In various aspects, n, when present, is 0 or 1. In a further aspect, n, when present, is 0. In a still further aspect, n, when present, is 1.

In various aspects, m, when present, is 0 or 1. In a further aspect, m, when present, is 0. In a still further aspect, m, when present, is 1.

a. Z Groups

In one aspect, Z, when present, is selected from —O—, —S—, and —NR$^{20}$—. In a further aspect, Z, when present, is selected from —O— and —NR$^{20}$—. In a still further aspect, Z, when present, is selected from —S— and —NR$^{20}$—. In yet a further aspect, Z, when present, is —NR$^{20}$—. In an even further aspect, Z, when present, is —S—. In a still further aspect, Z, when present, is —O—.

a. Q Groups

In one aspect, Q, when present, is selected from —O—, —S—, and —NR$^{21}$—. In a further aspect, Q, when present, is selected from —O— and —NR$^{21}$—. In a still further aspect, Q, when present, is selected from —S— and —NR$^{21}$—. In yet a further aspect, Q, when present, is —NR$^{21}$—. In an even further aspect, Q, when present, is —S—. In a still further aspect, Q, when present, is —O—.

b. $R^{1A}$, $R^{1B}$, $R^{1C}$, $R^{1D}$, and $R^{1E}$ Groups

In one aspect, each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, and C2-C4 alkenyl. In a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, methyl, ethyl, and ethenyl. In yet a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, and methyl.

In various aspects, each of $R^{1a}$, $R^{1b}$, $R^{1c}$, $R^{1d}$, and $R^{1e}$ is independently selected from hydrogen, C1-C4 alkyl, and C2-C4 alkenyl. In a further aspect, each of $R^{1a}$, $R^{1b}$, $R^{1c}$, $R^{1d}$, and $R^{1e}$ is independently selected from hydrogen, methyl, ethyl, n-propyl, isopropyl, ethenyl, and propenyl. In a still further aspect, each of $R^{1a}$, $R^{1b}$, $R^{1c}$, $R^{1d}$, and $R^{1e}$ is independently selected from hydrogen, methyl, ethyl, and ethenyl. In yet a further aspect, each of $R^{1a}$, $R^{1b}$, $R^{1c}$, $R^{1d}$, and $R^{1e}$ is independently selected from hydrogen and methyl.

In various aspects, each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 haloalkyl, and C1-C4 cyanoalkyl. In a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{1a}$, $R^{1b}$, and $R^{1c}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{1a}$, $R^{1b}$, $R^{1c}$, $R^{1d}$, and $R^{1e}$ is independently selected from hydrogen, C1-C4 haloalkyl, and C1-C4 cyanoalkyl. In a further aspect, each of $R^{1a}$, $R^{1b}$, $R^{1c}$, $R^{1d}$, and $R^{1e}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{1a}$, $R^{1b}$, $R^{1c}$, $R^{1d}$, and $R^{1e}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{1a}$, $R^{1b}$, $R^{1c}$, $R^{1d}$, and $R^{1e}$ is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{1a}$, $R^{1b}$, $R^{1c}$, $R^{1d}$, and $R^{1e}$ is independently selected from hydrogen, C1-C4 hydroxyalkyl, C1-C4 haloalkoxy, and C1-C4 alkoxy. In a further aspect, each of $R^{1a}$, $R^{1b}$, $R^{1c}$, $R^{1d}$, and $R^{1e}$ is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{1a}$, $R^{1b}$, $R^{1c}$, $R^{1d}$, and $R^{1e}$ is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{1a}$, $R^{1b}$, $R^{1c}$, $R^{1d}$, and $R^{1e}$ is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of $R^{1a}$, $R^{1b}$, $R^{1c}$, $R^{1d}$, and $R^{1e}$ is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of $R^{1a}$, $R^{1b}$, $R^{1c}$, $R^{1d}$, and $R^{1e}$ is independently selected from hydrogen, C1-C4 alkylamino, (C1-C4)(C1-C4) dialkylamino, and C1-C4 aminoalkyl. In a further aspect, each of $R^{1a}$, $R^{1b}$, $R^{1c}$, $R^{1d}$, and $R^{1e}$ is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{1a}$, $R^{1b}$, $R^{1c}$, $R^{1d}$, and $R^{1e}$ is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{1a}$, $R^{1b}$, $R^{1c}$, $R^{1d}$, and $R^{1e}$ is independently selected from hydrogen, —NHCH$_3$, —N(CH$_3$)$_2$, and —CH$_2$NH$_2$.

In various aspects, each of $R^{1a}$, $R^{1b}$, $R^{1c}$, $R^{1d}$, and $R^{1e}$ is independently selected from hydrogen, halogen, C1-C4 alkyl, C1-C4 haloalkyl, C1-C4 haloalkoxy, and C1-C4 alkoxy. In a further aspect, each of $R^{1a}$, $R^{1b}$, $R^{1c}$, $R^{1d}$, and $R^{1e}$ is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{1a}$, $R^{1b}$, $R^{1c}$, $R^{1d}$, and $R^{1e}$ is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{1a}$, R$^{1b}$, R$^{1c}$, R$^{1d}$, and R$^{1e}$ is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of R$^{1a}$, R$^{1b}$, R$^{1c}$, R$^{1d}$, and R$^{1e}$ is independently selected from hydrogen and halogen. In a further aspect, each of R$^{1a}$, R$^{1b}$, R$^{1c}$, R$^{1d}$, and R$^{1e}$ is independently selected from hydrogen, —F, —Cl, and —Br. In a still further aspect, each of R$^{1a}$, R$^{1b}$, R$^{1c}$, R$^{1d}$, and R$^{1e}$ is independently selected from hydrogen, —F, and —Cl. In yet a further aspect, each of R$^{1a}$, R$^{1b}$, R$^{1c}$, R$^{1d}$, and R$^{1e}$ is independently selected from hydrogen and —F. In an even further aspect, each of R$^{1a}$, R$^{1b}$, R$^{1c}$, R$^{1d}$, and R$^{1e}$ is independently selected from hydrogen and —Cl.

In various aspects, each of R$^{1a}$, R$^{1b}$, R$^{1c}$, R$^{1d}$, and R$^{1e}$ is hydrogen. In a further aspect, at least one of R$^{1a}$, R$^{1b}$, R$^{1c}$, R$^{1d}$, and R$^{1e}$ is hydrogen. In a still further aspect, two of R$^{1a}$, R$^{1b}$, R$^{1c}$, R$^{1d}$, and R$^{1e}$ is hydrogen. In yet further aspect, three of R$^{1a}$, R$^{1b}$, R$^{1c}$, R$^{1d}$, and R$^{1e}$ is hydrogen. In an even further aspect, four of R$^{1a}$, R$^{1b}$, R$^{1c}$, R$^{1d}$, and R$^{1e}$ is hydrogen.

c. R$^2$ and R$^3$ Groups

In one aspect, each of R$^2$ and R$^3$ is independently selected from hydrogen and C1-C4 alkyl. In a further aspect, each of R$^2$ and R$^3$ is independently selected from hydrogen, methyl, ethyl, n-propyl, and isopropyl. In a still further aspect, each of R$^2$ and R$^3$ is independently selected from hydrogen, methyl, and ethyl. In yet a further aspect, each of R$^2$ and R$^3$ is independently selected from hydrogen and ethyl. In an even further aspect, each of R$^2$ and R$^3$ is independently selected from hydrogen and methyl. In a still further aspect, each of R$^2$ and R$^3$ is hydrogen.

In various aspects, R$^2$ is selected from hydrogen and C1-C4 alkyl. In a further aspect, R$^2$ is selected from hydrogen, methyl, ethyl, n-propyl, and isopropyl. In a still further aspect, R$^2$ is selected from hydrogen, methyl, and ethyl. In yet a further aspect, R$^2$ is selected from hydrogen and ethyl. In an even further aspect, R$^2$ is selected from hydrogen and methyl.

In various aspects, R$^3$ is selected from hydrogen and C1-C4 alkyl. In a further aspect, R$^3$ is selected from hydrogen, methyl, ethyl, n-propyl, and isopropyl. In a still further aspect, R$^3$ is selected from hydrogen, methyl, and ethyl. In yet a further aspect, R$^3$ is selected from hydrogen and ethyl. In an even further aspect, R$^3$ is selected from hydrogen and methyl.

In various aspects, each of R$^2$ and R$^3$ is independently C1-C4 alkyl. In a further aspect, each of R$^2$ and R$^3$ is independently selected from methyl, ethyl, n-propyl, and isopropyl. In a still further aspect, each of R$^2$ and R$^3$ is independently selected from methyl and ethyl. In yet a further aspect, each of R$^2$ and R$^3$ is ethyl. In an even further aspect, each of R$^2$ and R$^3$ is methyl.

d. R$^{10A}$, R$^{10B}$, R$^{10C}$, R$^{10D}$, R$^{10E}$, and R$^{10F}$ Groups

In one aspect, each of R$^{10a}$, R$^{10b}$, R$^{10c}$, R$^{10d}$, R$^{10e}$, and R$^{10f}$ when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{10a}$, R$^{10b}$, R$^{10c}$, R$^{10d}$, R$^{10e}$, and R$^{10f}$ when present, is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 alkyl, and C2-C4 alkenyl. In a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, methyl, ethyl, n-propyl, isopropyl, ethenyl, and propenyl. In a still further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, methyl, ethyl, and ethenyl. In yet a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, and methyl.

In various aspects, each of R$^{10a}$, R$^{10b}$, R$^{10c}$, R$^{10d}$, R$^{10e}$, and R$^{10f}$, when present, is independently selected from hydrogen, C1-C4 alkyl, and C2-C4 alkenyl. In a further aspect, each of R$^{10a}$, R$^{10b}$, R$^{10c}$, R$^{10d}$, R$^{10e}$, and R$^{10f}$ when present, is independently selected from hydrogen, methyl, ethyl, n-propyl, isopropyl, ethenyl, and propenyl. In a still further aspect, each of R$^{10a}$, R$^{10b}$, R$^{10c}$, R$^{10d}$, R$^{10e}$, and R$^{10f}$, when present, is independently selected from hydrogen, methyl, ethyl, and ethenyl. In yet a further aspect, each of R$^{10a}$, R$^{10b}$, R$^{10c}$, R$^{10d}$, R$^{10e}$, and R$^{10f}$ when present, is independently selected from hydrogen and methyl.

In various aspects, each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 haloalkyl, and C1-C4 cyanoalkyl. In a further aspect, each of R$^{10a}$, R$^{10b}$, R$^{10c}$, R$^{10d}$, R$^{10e}$, and R$^{10f}$ when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of R$^{10a}$, R$^{10b}$, R$^{10c}$, R$^{10d}$, R$^{10e}$, and R$^{10f}$ when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of R$^{10a}$, R$^{10b}$, R$^{10c}$, R$^{10d}$, R$^{10e}$, and R$^{10f}$, when present, is independently selected from hydrogen, C1-C4 haloalkyl, and C1-C4 cyanoalkyl. In a further aspect, each of R$^{10a}$, R$^{10b}$, R$^{10c}$, R$^{10d}$, R$^{10e}$, and R$^{10f}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of R$^{10a}$, R$^{10b}$, R$^{10c}$, R$^{10d}$, R$^{10e}$, and R$^{10f}$ when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of R$^{10a}$, R$^{10b}$, R$^{10c}$, R$^{10d}$, R$^{10e}$, and R$^{10f}$, when present, is independently selected from hydrogen, —CCl$_3$, —CF$_3$, —CHCl$_2$, —CHF$_2$, —CH$_2$Cl, —CH$_2$F, and —CH$_2$CN.

In various aspects, each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{10a}$, R$^{10b}$, R$^{10c}$, R$^{10d}$, R$^{10e}$, and R$^{10f}$, when present, is independently selected from hydrogen, C1-C4 hydroxyalkyl, C1-C4 haloalkoxy, and C1-C4 alkoxy. In a further aspect, each of R$^{10a}$, R$^{10b}$, R$^{10c}$, R$^{10d}$, R$^{10e}$, and R$^{10f}$, when present, is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{10a}$, R$^{10b}$, R$^{10c}$, R$^{10d}$, R$^{10e}$, and R$^{10f}$, when present, is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of R$^{10a}$, R$^{10b}$, R$^{10c}$, R$^{10d}$, R$^{10e}$, and R$^{10f}$, when present, is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of R$^{10a}$, R$^{10b}$, R$^{10c}$, R$^{10d}$, R$^{10e}$, and R$^{10f}$, when present, is independently selected from hydrogen, C1-C4 alkylamino, (C1-C4)(C1-C4) dialkylamino, and C1-C4 aminoalkyl. In a further aspect, each of R$^{10a}$, R$^{10b}$, R$^{10c}$, R$^{10d}$, R$^{10e}$, and R$^{10f}$, when present, is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{10a}$, R$^{10b}$, R$^{10c}$, R$^{10d}$, R$^{10e}$, and R$^{10f}$, when present, is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{10a}$, R$^{10b}$, R$^{10c}$, R$^{10d}$, R$^{10e}$, and R$^{10f}$, when present, is independently selected from hydrogen, —NHCH$_3$, —N(CH$_3$)$_2$, and —CH$_2$NH$_2$.

In various aspects, each of R$^{10a}$, R$^{10b}$, R$^{10c}$, R$^{10d}$, R$^{10e}$, and R$^{10f}$, when present, is independently selected from hydrogen, halogen, C1-C4 alkyl, C1-C4 haloalkyl, C1-C4 haloalkoxy, and C1-C4 alkoxy. In a further aspect, each of R$^{10a}$, R$^{10b}$, R$^{10c}$, R$^{10d}$, R$^{10e}$, and R$^{10f}$, when present, is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{10a}$, R$^{10b}$, R$^{10c}$, R$^{10d}$, R$^{10e}$, and R$^{10f}$, when present, is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{10a}$, R$^{10b}$, R$^{10c}$, R$^{10d}$, R$^{10e}$, and R$^{10f}$ when present, is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of $R^{10a}$, $R^{10b}$, $R^{10c}$, $R^{10d}$, $R^{10e}$, and $R^{10f}$, when present, is independently selected from hydrogen and halogen. In a further aspect, each of $R^{10a}$, $R^{10b}$, $R^{10c}$, $R^{10d}$, $R^{10e}$, and $R^{10f}$, when present, is independently selected from hydrogen, —F, —Cl, and —Br. In a still further aspect, each of $R^{10a}$, $R^{10b}$, $R^{10c}$, $R^{10d}$, $R^{10e}$, and $R^{10f}$, when present, is independently selected from hydrogen, —F, and —Cl. In yet a further aspect, each of $R^{10a}$, $R^{10b}$, $R^{10c}$, $R^{10d}$, $R^{10e}$, and $R^{10f}$, when present, is independently selected from hydrogen and —F. In an even further aspect, each of $R^{10a}$, $R^{10b}$, $R^{10c}$, $R^{10d}$, $R^{10e}$, and $R^{10f}$, when present, is independently selected from hydrogen and —Cl.

In various aspects, each of $R^{10a}$, $R^{10b}$, $R^{10c}$, $R^{10d}$, $R^{10e}$, and $R^{10f}$, when present, is hydrogen. In a further aspect, at least one of $R^{10a}$, $R^{10b}$, $R^{10c}$, $R^{10d}$, $R^{10e}$, and $R^{10f}$ when present, is hydrogen. In a still further aspect, two of $R^{10a}$, $R^{10b}$, $R^{10c}$, $R^{10d}$, $R^{10e}$, and $R^{10f}$, when present, is hydrogen. In yet further aspect, three of $R^{10a}$, $R^{10b}$, $R^{10c}$, $R^{10d}$, $R^{10e}$, and $R^{10f}$, when present, is hydrogen. In an even further aspect, four of $R^{10a}$, $R^{10b}$, $R^{10c}$, $R^{10d}$, $R^{10e}$, and $R^{10f}$ when present, is hydrogen.

e. $R^{11A}$ and $R^{11B}$ Groups

In one aspect, each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{11a}$ and $R^{11b}$, when present, is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{11a}$ and $R^{11b}$, when present, is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{11a}$ and $R^{11b}$, when present, is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{11a}$ and $R^{11b}$, when present, is independently selected from hydrogen, halogen, —CN, —NH$_2$, —OH, —NO$_2$, C1-C4 alkyl, and C2-C4 alkenyl. In a further aspect, each of $R^{11a}$ and $R^{11b}$, when present, is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{11a}$ and $R^{11b}$, when present, is independently selected from hydrogen, —F, —Cl, —CN, —NH$_2$, —OH, —NO$_2$, methyl, ethyl, and ethenyl. In yet a further aspect, each of $R^{11a}$ and $R^{11b}$, when present, is independently selected from hydrogen, —F, —Cl, —CN, —NH$_2$, —OH, —NO$_2$, and methyl.

In various aspects, each of $R^{11a}$ and $R^{11b}$, when present, is independently selected from hydrogen, C1-C4 alkyl, and C2-C4 alkenyl. In a further aspect, each of $R^{11a}$ and $R^{11b}$, when present, is independently selected from hydrogen, methyl, ethyl, n-propyl, isopropyl, ethenyl, and propenyl. In a still further aspect, each of $R^{11a}$ and $R^{11b}$, when present, is independently selected from hydrogen, methyl, ethyl, and ethenyl. In yet a further aspect, each of $R^{11a}$ and $R^{11b}$, when present, is independently selected from hydrogen and methyl.

In various aspects, each of $R^{11a}$ and $R^{11b}$, when present, is independently selected from hydrogen, halogen, —CN, —NH$_2$, —OH, —NO$_2$, C1-C4 haloalkyl, and C1-C4 cyanoalkyl. In a further aspect, each of $R^{11a}$ and $R^{11b}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{11a}$ and $R^{11b}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{11a}$ and $R^{11b}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{11a}$ and $R^{11b}$, when present, is independently selected from hydrogen, C1-C4 haloalkyl, and C1-C4 cyanoalkyl. In a further aspect, each of $R^{11a}$ and $R^{11b}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{11a}$ and $R^{11b}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{11a}$ and $R^{11b}$, when present, is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{11a}$ and $R^{11b}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{11a}$ and $R^{11b}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{11a}$ and $R^{11b}$, when present, is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{11a}$ and R$^{11b}$, when present, is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{11a}$ and R$^{11b}$, when present, is independently selected from hydrogen, C1-C4 hydroxyalkyl, C1-C4 haloalkoxy, and C1-C4 alkoxy. In a further aspect, each of R$^{11a}$ and R$^{11b}$, when present, is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{11a}$ and R$^{11b}$, when present, is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{11a}$ and R$^{11b}$, when present, is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{11a}$ and R$^{11b}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of R$^{11a}$ and R$^{11b}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{11a}$ and R$^{1b}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of R$^{11a}$ and R$^{11b}$, when present, is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of R$^{11a}$ and R$^{11b}$, when present, is independently selected from hydrogen, C1-C4 alkylamino, (C1-C4)(C1-C4) dialkylamino, and C1-C4 aminoalkyl. In a further aspect, each of R$^{11a}$ and R$^{11b}$, when present, is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{11a}$ and R$^{1b}$, when present, is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{11a}$ and R$^{11b}$, when present, is independently selected from hydrogen, —NHCH$_3$, —N(CH$_3$)$_2$, and —CH$_2$NH$_2$.

In various aspects, each of R$^{11a}$ and R$^{11b}$, when present, is independently selected from hydrogen, halogen, C1-C4 alkyl, C1-C4 haloalkyl, C1-C4 haloalkoxy, and C1-C4 alkoxy. In a further aspect, each of R$^{11a}$ and R$^{11b}$, when present, is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$) CH$_2$F, —OCH$_3$, —OCH$_2$CH$_3$, —OCH$_2$CH$_2$CH$_3$, and —OCH(CH$_3$)$_2$. In a still further aspect, each of R$^{11a}$ and R$^{11b}$ when present, is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{11a}$ and R$^{11b}$, when present, is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of R$^{11a}$ and R$^{11b}$, when present, is independently selected from hydrogen and halogen. In a further aspect, each of R$^{11a}$ and R$^{11b}$, when present, is independently selected from hydrogen, —F, —Cl, and —Br. In a still further aspect, each of R$^{11a}$ and R$^{1b}$, when present, is independently selected from hydrogen, —F, and —Cl. In yet a further aspect, each of R$^{11a}$ and R$^{11b}$, when present, is independently selected from hydrogen and —F. In an even further aspect, each of R$^{11a}$ and R$^{11b}$, when present, is independently selected from hydrogen and —Cl.

In various aspects, each of R$^{11a}$ and R$^{1b}$, when present, is hydrogen. In a further aspect, one of R$^{11a}$ and R$^{11b}$ when present, is hydrogen.

f. R$^{12A}$, R$^{12B}$, R$^{12C}$, and R$^{12D}$ Groups

In one aspect, each of R$^{12a}$, R$^{12b}$, R$^{12c}$, and R$^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of R$^{12a}$, R$^{12b}$, R$^{12c}$, and R$^{12d}$, when present, is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$) CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$) CH$_2$NH$_2$. In a still further aspect, each of R$^{12a}$, R$^{12b}$, R$^{12c}$ and R$^{12d}$, when present, is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$) CH$_2$CH$_3$, —CH$_2$NH$_2$, and —CH$_2$CH$_2$NH$_2$. In yet a further aspect, each of R$^{12a}$, R$^{12b}$, R$^{12c}$, and R$^{12d}$, when present, is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, and C2-C4 alkenyl. In a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, methyl, ethyl, and ethenyl. In yet a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, and methyl.

In various aspects, each of $R^{12a}$, $R^{12b}$, $R^{12c}$, and $R^{12d}$, when present, is independently selected from hydrogen, C1-C4 alkyl, and C2-C4 alkenyl. In a further aspect, each of $R^{12a}$, $R^{12b}$, $R^{12c}$, and $R^{12d}$, when present, is independently selected from hydrogen, methyl, ethyl, n-propyl, isopropyl, ethenyl, and propenyl. In a still further aspect, each of $R^{12a}$, $R^{12b}$, $R^{12c}$, and $R^{12d}$, when present, is independently selected from hydrogen, methyl, ethyl, and ethenyl. In yet a further aspect, each of $R^{12a}$, $R^{12b}$, $R^{12c}$, and $R^{12d}$, when present, is independently selected from hydrogen and methyl.

In various aspects, each of $R^{12}$, $R^{12b}$, $R^{12c}$, and $R^{12d}$, when present, is independently selected from hydrogen, halogen, —CN, —NH$_2$, —OH, —NO$_2$, C1-C4 haloalkyl, and C1-C4 cyanoalkyl. In a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{12a}$, $R^{12b}$, $R^{12c}$ and $R^{12d}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{12a}$, $R^{12b}$, $R^{12c}$, and $R^{12d}$, when present, is independently selected from hydrogen, C1-C4 haloalkyl, and C1-C4 cyanoalkyl. In a further aspect, each of $R^{12}$, $R^{12b}$, $R^{12c}$, and $R^{12d}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{12a}$, $R^{12b}$, $R^{12c}$, and $R^{12d}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{12a}$, $R^{12b}$, $R^{12c}$, and $R^{12d}$, when present, is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{12a}$, $R^{12b}$, $R^{12c}$, and $R^{12d}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{12a}$, $R^{12b}$, $R^{12c}$, and $R^{12d}$, when present, is independently selected from hydrogen, C1-C4 hydroxyalkyl, C1-C4 haloalkoxy, and C1-C4 alkoxy. In a further aspect, each of $R^{12a}$, $R^{12b}$, $R^{12c}$, and $R^{12d}$, when present, is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{12a}$, $R^{12b}$, $R^{12c}$, and $R^{12d}$, when present, is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{12a}$, $R^{12b}$, $R^{12c}$, and $R^{12d}$, when present, is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of $R^{12a}$, $R^{12b}$, $R^{12c}$, and $R^{12d}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{12a}$, $R^{12b}$, $R^{12c}$ and $R^{12d}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of $R^{12a}$, $R^{12b}$, $R^{12c}$, and $R^{12a}$, when present, is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of $R^{12a}$, $R^{12b}$, $R^{12c}$, and $R^{12a}$, when present, is independently selected from hydrogen, C1-C4 alkylamino, (C1-C4)(C1-C4) dialkylamino, and C1-C4 aminoalkyl. In a further aspect, each of $R^{12a}$, $R^{12b}$, $R^{12c}$, and $R^{12d}$, when present, is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{12a}$, R$^{12b}$, R$^{12c}$, and R$^{12d}$, when present, is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{12a}$, R$^{12b}$, R$^{12c}$, and R$^{12d}$, when present, is independently selected from hydrogen, —NHCH$_3$, —N(CH$_3$)$_2$, and —CH$_2$NH$_2$.

In various aspects, each of R$^{12a}$, R$^{12b}$, R$^{12c}$, and R$^{12d}$, when present, is independently selected from hydrogen, halogen, C1-C4 alkyl, C1-C4 haloalkyl, C1-C4 haloalkoxy, and C1-C4 alkoxy. In a further aspect, each of R$^{12a}$, R$^{12b}$, R$^{12c}$, and R$^{12d}$, when present, is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{12a}$, R$^{12b}$, R$^{12c}$, and R$^{12d}$, when present, is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{12a}$, R$^{12b}$, R$^{12c}$, and R$^{12d}$, when present, is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of R$^{12a}$, R$^{12b}$, R$^{12c}$, and R$^{12d}$, when present, is independently selected from hydrogen and halogen. In a further aspect, each of R$^{12a}$, R$^{12b}$, R$^{12c}$, and R$^{12d}$, when present, is independently selected from hydrogen, —F, —Cl, and —Br. In a still further aspect, each of R$^{12a}$, R$^{12b}$, R$^{12c}$, and R$^{12d}$, when present, is independently selected from hydrogen, —F, and —Cl. In yet a further aspect, each of R$^{12a}$, R$^{12b}$, R$^{12c}$, and R$^{12d}$, when present, is independently selected from hydrogen and —F. In an even further aspect, each of R$^{12a}$, R$^{12b}$, R$^{12c}$, and R$^{12d}$, when present, is independently selected from hydrogen and —Cl.

In various aspects, each of R$^{12a}$, R$^{12b}$, R$^{12c}$, and R$^{12d}$, when present, is hydrogen. In a further aspect, at least one of R$^{12a}$, R$^{12b}$, R$^{12c}$, and R$^{12d}$, when present, is hydrogen. In a still further aspect, two of R$^{12a}$, R$^{12b}$, R$^{12c}$, and R$^{12d}$, when present, is hydrogen. In yet further aspect, three of R$^{12a}$, R$^{12b}$, R$^{12c}$, and R$^{12d}$, when present, is hydrogen. In an even further aspect, four of R$^{12a}$, R$^{12b}$, R$^{12c}$, and R$^{12d}$, when present, is hydrogen.

g. R$^{13}$ Groups

In one aspect, R$^{13}$, when present, is selected from —OH, —NH$_2$, C1-C4 alkoxy, C1-C4 alkylamino, and (C1-C4)(C1-C4) dialkylamino. In a further aspect, R$^{13}$, when present, is selected from —OH, —NH$_2$, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, and —N(CH$_3$)CH(CH$_3$)$_2$. In a still further aspect, R$^{13}$, when present, is selected from —OH, —NH$_2$, —OCH$_3$, —OCH$_2$CH$_3$, —NHCH$_3$, —NHCH$_2$CH$_3$, —N(CH$_3$)$_2$, and —N(CH$_3$)CH$_2$CH$_3$. In yet a further aspect, R$^{13}$, when present, is selected from —OH, —NH$_2$, —OCH$_3$, —NHCH$_3$, and —N(CH$_3$)$_2$.

In various aspects, R$^{13}$, when present, is selected from —OH and C1-C4 alkoxy. In a further aspect, R$^{13}$, when present, is selected from —OH, —OCH$_3$, —OCH$_2$CH$_3$, —OCH$_2$CH$_2$CH$_3$, and —OCH(CH$_3$)$_2$. In a still further aspect, R$^{13}$, when present, is selected from —OH, —OCH$_3$, and —OCH$_2$CH$_3$. In yet a further aspect, R$^{13}$, when present, is selected from —OH and —OCH$_3$.

In various aspects, R$^{13}$, when present, is selected from —NH$_2$, C1-C4 alkylamino, and (C1-C4)(C1-C4) dialkylamino. In a further aspect, R$^{13}$, when present, is selected from —NH$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, and —N(CH$_3$)CH(CH$_3$)$_2$. In a still further aspect, R$^{13}$, when present, is selected from —NH$_2$, —NHCH$_3$, —NHCH$_2$CH$_3$, —N(CH$_3$)$_2$, and —N(CH$_3$)CH$_2$CH$_3$. In yet a further aspect, R$^{13}$, when present, is selected from —NH$_2$, —NHCH$_3$, and —N(CH$_3$)$_2$.

In various aspects, R$^{13}$, when present, is —OH. In a further aspect, R$^{13}$, when present, is —NH$_2$.

h. R$^{14A}$, R$^{14B}$, R$^{14C}$, R$^{14D}$, R$^{14E}$, and R$^{14F}$ Groups

In one aspect, each of R$^{14a}$, R$^{14b}$, R$^{14c}$, R$^{14d}$, R$^{14e}$, and R$^{14f}$ when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of R$^{14a}$, R$^{14b}$, R$^{14c}$, R$^{14d}$, R$^{14e}$, and R$^{14f}$ when present, is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{14a}$, R$^{14b}$, R$^{14c}$, R$^{14d}$, R$^{14e}$, and R$^{14f}$ when present, is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{14a}$, R$^{14b}$, R$^{14c}$, R$^{14d}$, R$^{14e}$, and R$^{14f}$ when present, is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of R$^{14a}$, R$^{14b}$, R$^{14c}$, R$^{14d}$, R$^{14e}$, and R$^{14f}$, when present, is independently selected from hydrogen, halogen, —CN, —NH$_2$, —OH, —NO$_2$, C1-C4 alkyl, and C2-C4 alkenyl. In a further aspect, each of R$^{14a}$, R$^{14b}$, R$^{14c}$, R$^{14d}$, R$^{14e}$, and R$^{14f}$ when present, is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, methyl, ethyl, and ethenyl. In yet a further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, and methyl.

In various aspects, each of $R^{14a}$, $R^{14b}$, $R^{14c}$, $R^{14d}$, $R^{14e}$, and $R^{14f}$, when present, is independently selected from hydrogen, C1-C4 alkyl, and C2-C4 alkenyl. In a further aspect, each of $R^{14a}$, $R^{14b}$, $R^{14c}$, $R^{14d}$, $R^{14e}$, and $R^{14f}$, when present, is independently selected from hydrogen, methyl, ethyl, n-propyl, isopropyl, ethenyl, and propenyl. In a still further aspect, each of $R^{14a}$, $R^{14b}$, $R^{14c}$, $R^{14d}$, $R^{14e}$, and $R^{14f}$, when present, is independently selected from hydrogen, methyl, ethyl, and ethenyl. In yet a further aspect, each of $R^{14a}$, $R^{14b}$, $R^{14c}$, $R^{14d}$, $R^{14e}$, and $R^{14f}$, when present, is independently selected from hydrogen and methyl.

In various aspects, each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 haloalkyl, and C1-C4 cyanoalkyl. In a further aspect, each of $R^{14a}$, $R^{14b}$, $R^{14c}$, $R^{14d}$, $R^{14e}$, and $R^{14}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{14a}$, $R^{14b}$, $R^{14c}$, $R^{14d}$, $R^{14e}$, and $R^{14f}$ when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{14a}$, $R^{14b}$, $R^{14c}$, $R^{14d}$, $R^{14e}$, and $R^{14f}$, when present, is independently selected from hydrogen, C1-C4 haloalkyl, and C1-C4 cyanoalkyl. In a further aspect, each of $R^{14a}$, $R^{14b}$, $R^{14c}$, $R^{14d}$, $R^{14e}$, and $R^{14f}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{14a}$, $R^{14b}$, $R^{14c}$, $R^{14d}$, $R^{14e}$, and $R^{14f}$ when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{14a}$, $R^{14b}$, $R^{14c}$, $R^{14d}$, $R^{14e}$, and $R^{14f}$, when present, is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{14a}$, $R^{14b}$, $R^{14c}$, $R^{14d}$, $R^{14e}$, and $R^{14f}$, when present, is independently selected from hydrogen, C1-C4 hydroxyalkyl, C1-C4 haloalkoxy, and C1-C4 alkoxy. In a further aspect, each of $R^{14a}$, $R^{14b}$, $R^{14c}$, $R^{14d}$, $R^{14e}$, and $R^{14f}$, when present, is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{14a}$, $R^{14b}$, $R^{14c}$, $R^{14d}$, $R^{14e}$, and $R^{14f}$, when present, is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{14a}$, $R^{14b}$, $R^{14c}$, $R^{14d}$, $R^{14e}$, and $R^{14f}$, when present, is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{14a}$, $R^{14b}$, $R^{14c}$, $R^{14d}$, $R^{14e}$, and $R^{14f}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of $R^{14a}$, $R^{14b}$, $R^{14c}$, $R^{14d}$, $R^{14e}$, and $R^{14f}$ when present, is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of $R^{14a}$, $R^{14b}$, $R^{14c}$, $R^{14d}$, $R^{14e}$, and $R^{14f}$, when present, is independently selected from hydrogen, C1-C4 alkylamino, (C1-C4)(C1-C4) dialkylamino, and C1-C4 aminoalkyl. In a further aspect, each of $R^{14a}$, $R^{14b}$, $R^{14c}$, $R^{14d}$, $R^{14e}$, and $R^{14f}$ when present, is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{14a}$, $R^{14b}$, $R^{14c}$, $R^{14d}$, $R^{14e}$, and $R^{14f}$ when present, is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{14a}$, $R^{14b}$, $R^{14c}$, $R^{14d}$, $R^{14e}$, and $R^{14f}$ when present, is independently selected from hydrogen, —NHCH$_3$, —N(CH$_3$)$_2$, and —CH$_2$NH$_2$.

In various aspects, each of $R^{14a}$, $R^{14b}$, $R^{14c}$, $R^{14d}$, $R^{14e}$, and $R^{14f}$, when present, is independently selected from hydrogen, halogen, C1-C4 alkyl, C1-C4 haloalkyl, C1-C4 haloalkoxy, and C1-C4 alkoxy. In a further aspect, each of $R^{14a}$, $R^{14b}$, $R^{14c}$, $R^{14d}$, $R^{14e}$, and $R^{14f}$ when present, is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{14a}$, $R^{14b}$, $R^{14c}$, $R^{14d}$, $R^{14e}$, and $R^{14f}$, when present, is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{14a}$, $R^{14b}$, $R^{14c}$, $R^{14d}$, $R^{14e}$, and $R^{14f}$ when present, is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of $R^{14a}$, $R^{14b}$, $R^{14c}$, $R^{14d}$, $R^{14e}$, and $R^{14f}$, when present, is independently selected from hydrogen and halogen. In a further aspect, each of $R^{14a}$, $R^{14b}$, $R^{14c}$, $R^{14d}$, $R^{14e}$, and $R^{14f}$, when present, is independently selected from hydrogen, —F, —Cl, and —Br. In a still further aspect, each of $R^{14a}$, $R^{14b}$, $R^{14c}$, $R^{14d}$, $R^{14e}$, and $R^{14f}$, when present, is independently selected from hydrogen, —F, and —Cl. In yet a further aspect, each of $R^{14a}$, $R^{14b}$, $R^{14c}$, $R^{14d}$, $R^{14e}$, and $R^{14f}$ when present, is independently selected from hydrogen and —F. In an even further aspect, each of $R^{14a}$, $R^{14b}$, $R^{14c}$, $R^{14d}$, $R^{14e}$, and $R^{14f}$, when present, is independently selected from hydrogen and —Cl.

In various aspects, each of $R^{14a}$, $R^{14b}$, $R^{14c}$, $R^{14d}$, $R^{14e}$, and $R^{14f}$, when present, is hydrogen. In a further aspect, at least one of $R^{14a}$, $R^{14b}$, $R^{14c}$, $R^{14d}$, $R^{14e}$, and $R^{14f}$, when present, is hydrogen. In a still further aspect, two of $R^{14a}$, $R^{14b}$, $R^{14c}$, $R^{14d}$, $R^{14e}$, and $R^{14f}$ when present, is hydrogen. In yet further aspect, three of $R^{14a}$, $R^{14b}$, $R^{14c}$, $R^{14d}$, $R^{14e}$, and $R^{14f}$ when present, is hydrogen. In an even further aspect, four of $R^{14a}$, $R^{14b}$, $R^{14c}$, $R^{14d}$, $R^{14e}$, and $R^{14f}$, when present, is hydrogen.

i. $R^{15A}$ and $R^{15B}$ Groups

In one aspect, each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{15a}$ and $R^{15b}$, when present, is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$F, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{15a}$ and $R^{15b}$, when present, is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{15a}$ and $R^{15b}$, when present, is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{15a}$ and $R^{15b}$, when present, is independently selected from hydrogen, halogen, —CN, —NH$_2$, —OH, —NO$_2$, C1-C4 alkyl, and C2-C4 alkenyl. In a further aspect, each of $R^{15a}$ and $R^{15b}$, when present, is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{15a}$ and $R^{15b}$, when present, is independently selected from hydrogen, —F, —Cl, —CN, —NH$_2$, —OH, —NO$_2$, methyl, ethyl, and ethenyl. In yet a further aspect, each of $R^{15a}$ and $R^{15b}$, when present, is independently selected from hydrogen, —F, —Cl, —CN, —NH$_2$, —OH, —NO$_2$, and methyl.

In various aspects, each of $R^{15a}$ and $R^{15b}$, when present, is independently selected from hydrogen, C1-C4 alkyl, and C2-C4 alkenyl. In a further aspect, each of $R^{15a}$ and $R^{15b}$, when present, is independently selected from hydrogen, methyl, ethyl, n-propyl, isopropyl, ethenyl, and propenyl. In a still further aspect, each of $R^{15a}$ and $R^{15b}$, when present, is independently selected from hydrogen, methyl, ethyl, and ethenyl. In yet a further aspect, each of $R^{15a}$ and $R^{15b}$, when present, is independently selected from hydrogen and methyl.

In various aspects, each of $R^{15a}$ and $R^{15b}$, when present, is independently selected from hydrogen, halogen, —CN, —NH$_2$, —OH, —NO$_2$, C1-C4 haloalkyl, and C1-C4 cyanoalkyl. In a further aspect, each of $R^{15a}$ and $R^{15b}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{15a}$ and $R^{15b}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{15a}$ and $R^{15b}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{15a}$ and $R^{15b}$, when present, is independently selected from hydrogen, C1-C4 haloalkyl, and C1-C4 cyanoalkyl. In a further aspect, each of $R^{15a}$ and $R^{15b}$, when present, is independently selected from hydrogen, —CCl₃, —CF₃, —CHCl₂, —CHF₂, —CH₂Cl, —CH₂F, —CH₂CH₂Cl, —CH₂CH₂F, —CH₂CH₂CH₂Cl, —CH₂CH₂CH₂F, —CH(CH₃)CH₂Cl, —CH(CH₃)CH₂F, —CH₂CN, —CH₂CH₂CN, —CH₂CH₂CH₂CN, and —CH(CH₃)CH₂CN. In a still further aspect, each of $R^{15a}$ and $R^{15b}$, when present, is independently selected from hydrogen, —CCl₃, —CF₃, —CHCl₂, —CHF₂, —CH₂Cl, —CH₂F, —CH₂CH₂Cl, —CH₂CH₂F, —CH₂CN, and —CH₂CH₂CN. In yet a further aspect, each of $R^{15a}$ and $R^{15b}$, when present, is independently selected from hydrogen, —CCl₃, —CF₃, —CHCl₂, —CHF₂, —CH₂Cl, —CH₂F, and —CH₂CN.

In various aspects, each of $R^{15a}$ and $R^{15b}$, when present, is independently selected from hydrogen, halogen, —CN, —NH₂, —OH, —NO₂, C1-C4 hydroxyalkyl, C1-C4 haloalkoxy, and C1-C4 alkoxy. In a further aspect, each of $R^{15a}$ and $R^{15b}$, when present, is independently selected from hydrogen, —F, —Cl, —CN, —NH₂, —OH, —NO₂, —CH₂OH, —CH₂CH₂OH, —CH₂CH₂CH₂OH, —CH(CH₃)CH₂OH, —OCCl₃, —OCF₃, —OCHCl₂, —OCHF₂, —OCH₂Cl, —OCH₂F, —OCH₂CH₂Cl, —OCH₂CH₂F, —OCH₂CH₂CH₂Cl, —OCH₂CH₂CH₂F, —OCH(CH₃)CH₂Cl, —OCH(CH₃)CH₂F, —OCH₃, —OCH₂CH₃, —OCH₂CH₂CH₃, and —OCH(CH₃)₂. In a still further aspect, each of $R^{15a}$ and $R^{15b}$, when present, is independently selected from hydrogen, —F, —Cl, —CN, —NH₂, —OH, —NO₂, —CH₂OH, —CH₂CH₂OH, —OCCl₃, —OCF₃, —OCHCl₂, —OCHF₂, —OCH₂Cl, —OCH₂F, —OCH₂CH₂Cl, —OCH₂CH₂F, —OCH₃, and —OCH₂CH₃. In yet a further aspect, each of $R^{15a}$ and $R^{15b}$, when present, is independently selected from hydrogen, —F, —Cl, —CN, —NH₂, —OH, —NO₂, —CH₂OH, —OCCl₃, —OCF₃, —OCHCl₂, —OCHF₂, —OCH₂Cl, —OCH₂F, and —OCH₃.

In various aspects, each of $R^{15a}$ and $R^{15b}$, when present, is independently selected from hydrogen, C1-C4 hydroxyalkyl, C1-C4 haloalkoxy, and C1-C4 alkoxy. In a further aspect, each of $R^{15a}$ and $R^{15b}$, when present, is independently selected from hydrogen, —CH₂OH, —CH₂CH₂OH, —CH₂CH₂CH₂OH, —CH(CH₃)CH₂OH, —OCCl₃, —OCF₃, —OCHCl₂, —OCHF₂, —OCH₂Cl, —OCH₂F, —OCH₂CH₂Cl, —OCH₂CH₂F, —OCH₂CH₂CH₂Cl, —OCH₂CH₂CH₂F, —OCH(CH₃)CH₂Cl, —OCH(CH₃)CH₂F, —OCH₃, —OCH₂CH₃, —OCH₂CH₂CH₃, and —OCH(CH₃)₂. In a still further aspect, each of $R^{15a}$ and $R^{15b}$, when present, is independently selected from hydrogen, —CH₂OH, —CH₂CH₂OH, —OCCl₃, —OCF₃, —OCHCl₂, —OCHF₂, —OCH₂Cl, —OCH₂F, —OCH₂CH₂Cl, —OCH₂CH₂F, —OCH₃, and —OCH₂CH₃. In yet a further aspect, each of $R^{15a}$ and $R^{15b}$, when present, is independently selected from hydrogen, —CH₂OH, —OCCl₃, —OCF₃, —OCHCl₂, —OCHF₂, —OCH₂Cl, —OCH₂F, and —OCH₃.

In various aspects, each of $R^{15a}$ and $R^{15b}$, when present, is independently selected from hydrogen, halogen, —CN, —NH₂, —OH, —NO₂, C1-C4 alkylamino, (C1-C4)(C1-C4) dialkylamino, and C1-C4 aminoalkyl. In a further aspect, each of $R^{15a}$ and $R^{15b}$, when present, is independently selected from hydrogen, —F, —Cl, —CN, —NH₂, —OH, —NO₂, —NHCH₃, —NHCH₂CH₃, —NHCH₂CH₂CH₃, —NHCH(CH₃)₂, —N(CH₃)₂, —N(CH₃)CH₂CH₃, —N(CH₂CH₃)CH₂CH₂CH₃, —N(CH₃)CH(CH₃)₂, —CH₂NH₂, —CH₂CH₂NH₂, —CH₂CH₂CH₂NH₂, and —CH(CH₃)CH₂NH₂. In a still further aspect, each of $R^{15a}$ and $R^{15b}$, when present, is independently selected from hydrogen, —F, —Cl, —CN, —NH₂, —OH, —NO₂, —NHCH₃, —NHCH₂CH₃, —N(CH₃)₂, —N(CH₃)CH₂CH₃, —CH₂CH₃, —CH₂NH₂, —CH₂CH₂NH₂. In yet a further aspect, each of $R^{15a}$ and $R^{15b}$, when present, is independently selected from hydrogen, —F, —Cl, —CN, —NH₂, —OH, —NO₂, —NHCH₃, —N(CH₃)₂, and —CH₂NH₂.

In various aspects, each of $R^{15a}$ and $R^{15b}$, when present, is independently selected from hydrogen, C1-C4 alkylamino, (C1-C4)(C1-C4) dialkylamino, and C1-C4 aminoalkyl. In a further aspect, each of $R^{15a}$ and $R^{15b}$, when present, is independently selected from hydrogen, —NHCH₃, —NHCH₂CH₃, —NHCH₂CH₂CH₃, —NHCH(CH₃)₂, —N(CH₃)₂, —N(CH₃)CH₂CH₃, —N(CH₂CH₃)CH₂CH₂CH₃, —N(CH₃)CH(CH₃)₂, —CH₂NH₂, —CH₂CH₂NH₂, —CH₂CH₂CH₂NH₂, and —CH(CH₃)CH₂NH₂. In a still further aspect, each of $R^{15a}$ and $R^{15b}$, when present, is independently selected from hydrogen, —NHCH₃, —NHCH₂CH₃, —N(CH₃)₂, —N(CH₃)CH₂CH₃, —CH₂NH₂, and —CH₂CH₂NH₂. In yet a further aspect, each of $R^{15a}$ and $R^{15b}$, when present, is independently selected from hydrogen, —NHCH₃, —N(CH₃)₂, and —CH₂NH₂.

In various aspects, each of $R^{15a}$ and $R^{15b}$, when present, is independently selected from hydrogen, halogen, C1-C4 alkyl, C1-C4 haloalkyl, C1-C4 haloalkoxy, and C1-C4 alkoxy. In a further aspect, each of $R^{15a}$ and $R^{15b}$, when present, is independently selected from hydrogen, —F, —Cl, methyl, ethyl, n-propyl, isopropyl, —CCl₃, —CF₃, —CHCl₂, —CHF₂, —CH₂Cl, —CH₂F, —CH₂CH₂Cl, —CH₂CH₂F, —CH₂CH₂CH₂Cl, —CH₂CH₂CH₂F, —CH(CH₃)CH₂Cl, —CH(CH₃)CH₂F, —OCCl₃, —OCF₃, —OCHCl₂, —OCHF₂, —OCH₂Cl, —OCH₂F, —OCH₂CH₂Cl, —OCH₂CH₂F, —OCH₂CH₂CH₂Cl, —OCH₂CH₂CH₂F, —OCH(CH₃)CH₂Cl, —OCH(CH₃)CH₂F, —OCH₃, —OCH₂CH₃, —OCH₂CH₂CH₃, and —OCH(CH₃)₂. In a still further aspect, each of $R^{15a}$ and $R^{15b}$, when present, is independently selected from hydrogen, —F, —Cl, methyl, ethyl, —CCl₃, —CF₃, —CHCl₂, —CHF₂, —CH₂Cl, —CH₂F, —CH₂CH₂Cl, —CH₂CH₂F, —OCCl₃, —OCF₃, —OCHCl₂, —OCHF₂, —OCH₂Cl, —OCH₂F, —OCH₂CH₂Cl, —OCH₂CH₂F, —OCH₃, and —OCH₂CH₃. In yet a further aspect, each of $R^{15a}$ and $R^{15b}$, when present, is independently selected from hydrogen, —F, —Cl, methyl, —CCl₃, —CF₃, —CHCl₂, —CHF₂, —CH₂Cl, —CH₂F, —OCCl₃, —OCF₃, —OCHCl₂, —OCHF₂, —OCH₂Cl, —OCH₂F, and —OCH₃.

In various aspects, each of $R^{15a}$ and $R^{15b}$, when present, is independently selected from hydrogen and halogen. In a further aspect, each of $R^{15a}$ and $R^{15b}$, when present, is independently selected from hydrogen, —F, —Cl, and —Br. In a still further aspect, each of $R^{15a}$ and $R^{15b}$, when present, is independently selected from hydrogen, —F, and —Cl. In yet a further aspect, each of $R^{15a}$ and $R^{15b}$, when present, is independently selected from hydrogen and —F. In an even further aspect, each of $R^{15a}$ and $R^{15b}$, when present, is independently selected from hydrogen and —Cl.

In various aspects, each of $R^{15a}$ and $R^{15b}$, when present, is hydrogen. In a further aspect, one of $R^{15a}$ and $R^{15b}$, when present, is hydrogen.

j. $R^{16A}$, $R^{16B}$, $R^{16C}$, and $R^{16D}$ Groups

In one aspect, each of $R^{16a}$, $R^{16b}$, $R^{16c}$, and $R^{16d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{16a}$, $R^{16b}$, $R^{16c}$, and $R^{16d}$, when present, is independently selected from hydrogen, —F, —Cl, —CN, —NH₂, —OH, —NO₂, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, and C2-C4 alkenyl. In a further aspect, each of $R^{6a}$, $R^{16b}$, $R^{16c}$, and $R^{16d}$, when present, is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{1a}$, $R^{16b}$, $R^{16c}$, and $R^{16d}$, when present, is independently selected from hydrogen, —F, —Cl, —CN, —NH$_2$, —OH, —NO$_2$, methyl, ethyl, and ethenyl. In yet a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, and methyl.

In various aspects, each of $R^{16a}$, $R^{16b}$, $R^{16c}$, and $R^{16d}$, when present, is independently selected from hydrogen, C1-C4 alkyl, and C2-C4 alkenyl. In a further aspect, each of $R^{6a}$, $R^{16b}$, $R^{16c}$, and $R^{16d}$, when present, is independently selected from hydrogen, methyl, ethyl, n-propyl, isopropyl, ethenyl, and propenyl. In a still further aspect, each of $R^{16a}$, $R^{16b}$, $R^{16c}$, and $R^{16d}$, when present, is independently selected from hydrogen, methyl, ethyl, and ethenyl. In yet a further aspect, each of $R^{16a}$, $R^{16b}$, $R^{16c}$, and $R^{16d}$, when present, is independently selected from hydrogen and methyl.

In various aspects, each of $R^{16a}$, $R^{16b}$, $R^{16c}$, and $R^{16d}$, when present, is independently selected from hydrogen, halogen, —CN, —NH$_2$, —OH, —NO$_2$, C1-C4 haloalkyl, and C1-C4 cyanoalkyl. In a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{16a}$, $R^{16b}$, $R^{16c}$, and $R^{16d}$, when present, is independently selected from hydrogen, C1-C4 haloalkyl, and C1-C4 cyanoalkyl. In a further aspect, each of $R^{16a}$, $R^{16b}$, $R^{16c}$, and $R^{16d}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{16a}$, $R^{16b}$, $R^{16c}$, and $R^{16d}$, when present, is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{16a}$, $R^{16b}$, $R^{16c}$, and $R^{16d}$, when present, is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{16a}$, $R^{16b}$, $R^{16c}$, and $R^{16d}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{16a}$, $R^{16b}$, $R^{16c}$, and $R^{16d}$, when present, is independently selected from hydrogen, C1-C4 hydroxyalkyl, C1-C4 haloalkoxy, and C1-C4 alkoxy. In a further aspect, each of $R^{16a}$, $R^{16b}$, $R^{16c}$, and $R^{16d}$, when present, is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{16a}$, $R^{16b}$, $R^{16c}$, and $R^{16d}$, when present, is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{16a}$, $R^{16b}$, $R^{16c}$, and $R^{16d}$, when present, is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of $R^{16a}$, $R^{16b}$, $R^{16c}$, and $R^{16d}$, when present, is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of $R^{16a}$, $R^{16b}$, $R^{16c}$, and $R^{16d}$, when present, is independently selected from hydrogen, C1-C4 alkylamino, (C1-C4)(C1-C4) dialkylamino, and C1-C4 aminoalkyl. In a further aspect, each of $R^{16a}$, $R^{16b}$, $R^{16c}$, and $R^{16d}$, when present, is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{16a}$, $R^{16b}$, $R^{16c}$, and $R^{16d}$, when present, is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{16a}$, $R^{16b}$, $R^{16c}$, and $R^{16d}$, when present, is independently selected from hydrogen, —NHCH$_3$, —N(CH$_3$)$_2$, and —CH$_2$NH$_2$.

In various aspects, each of $R^{16a}$, $R^{16b}$, $R^{16c}$, and $R^{16d}$, when present, is independently selected from hydrogen, halogen, C1-C4 alkyl, C1-C4 haloalkyl, C1-C4 haloalkoxy, and C1-C4 alkoxy. In a further aspect, each of $R^{16a}$, $R^{16b}$, $R^{16c}$, and $R^{16d}$, when present, is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{16a}$, $R^{16b}$, $R^{16c}$, and $R^{16d}$, when present, is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{16a}$, $R^{16b}$, $R^{16c}$, and $R^{16d}$, when present, is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of $R^{16a}$, $R^{16b}$, $R^{16c}$, and $R^{16d}$, when present, is independently selected from hydrogen and halogen. In a further aspect, each of $R^{16a}$, $R^{16b}$, $R^{16c}$, and $R^{16d}$, when present, is independently selected from hydrogen, —F, —Cl, and —Br. In a still further aspect, each of $R^{16a}$, $R^{16b}$, $R^{16c}$, and $R^{16d}$, when present, is independently selected from hydrogen, —F, and —Cl. In yet a further aspect, each of $R^{16a}$, $R^{16b}$, $R^{16c}$, and $R^{16d}$, when present, is independently selected from hydrogen and —F. In an even further aspect, each of $R^{16a}$, $R^{16b}$, $R^{16c}$, and $R^{16d}$, when present, is independently selected from hydrogen and —Cl.

In various aspects, each of $R^{16a}$, $R^{16b}$, $R^{16c}$, and $R^{16d}$, when present, is hydrogen. In a further aspect, at least one of $R^{16a}$, $R^{16b}$, $R^{16c}$, and $R^{16d}$, when present, is hydrogen. In a still further aspect, two of $R^{16a}$, $R^{16b}$, $R^{16c}$, and $R^{16d}$, when present, is hydrogen. In yet further aspect, three of $R^{16a}$, $R^{16b}$, $R^{16c}$, and $R^{16d}$, when present, is hydrogen.

k. $R^{17}$ Groups

In one aspect, $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl). In a further aspect, $R^{17}$, when present, is selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, —CH(CH$_3$)CH$_2$NH$_2$, —CO$_2$H, —CO$_2$CH$_3$, —CO$_2$CH$_2$CH$_3$, —CO$_2$CH$_2$CH$_2$CH$_3$, and —CO$_2$CH(CH$_3$)$_2$. In a still further aspect, $R^{17}$, when present, is selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$, —CO$_2$H, and —CO$_2$CH$_3$. In yet a further aspect, $R^{17}$, when present, is selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, —CH$_2$NH$_2$, —CO$_2$H, and —CO$_2$CH$_3$.

In various aspects, $R^{17}$, when present, is selected from hydrogen, halogen, —CN, —NH$_2$, —OH, —NO$_2$, C1-C4 alkyl, and C2-C4 alkenyl. In a further aspect, $R^{17}$, when present, is selected from hydrogen, —F, —Cl, —CN, —NH$_2$, —OH, —NO$_2$, methyl, ethyl, n-propyl, isopropyl, ethenyl, and propenyl. In a still further aspect, $R^{17}$, when present, is selected from hydrogen, —F, —Cl, —CN, —NH$_2$, —OH, —NO$_2$, methyl, ethyl, and ethenyl. In yet a further aspect, $R^{17}$, when present, is selected from hydrogen, —F, —Cl, —CN, —NH$_2$, —OH, —NO$_2$, and methyl.

In various aspects, $R^{17}$, when present, is selected from hydrogen, C1-C4 alkyl, and C2-C4 alkenyl. In a further aspect, $R^{17}$, when present, is selected from hydrogen, methyl, ethyl, n-propyl, isopropyl, ethenyl, and propenyl. In a still further aspect, $R^{17}$, when present, is selected from hydrogen, methyl, ethyl, and ethenyl. In yet a further aspect, $R^{17}$, when present, is selected from hydrogen and methyl.

In various aspects, $R^{17}$, when present, is selected from hydrogen, halogen, —CN, —NH$_2$, —OH, —NO$_2$, C1-C4 haloalkyl, and C1-C4 cyanoalkyl. In a further aspect, $R^{17}$, when present, is selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, $R^{17}$, when present, is selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, $R^{17}$, when present, is selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, $R^{17}$, when present, is selected from hydrogen, C1-C4 haloalkyl, and C1-C4 cyanoalkyl. In a further aspect, $R^{17}$, when present, is selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, $R^{17}$, when present, is selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, $R^{17}$, when present, is selected from hydrogen, —CCl$_3$, —CF$_3$, —CHCl$_2$, —CHF$_2$, —CH$_2$Cl, —CH$_2$F, and —CH$_2$CN.

In various aspects, $R^{17}$, when present, is selected from hydrogen, halogen, —CN, —NH$_2$, —OH, —NO$_2$, C1-C4 hydroxyalkyl, C1-C4 haloalkoxy, and C1-C4 alkoxy. In a further aspect, $R^{17}$, when present, is selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, $R^{17}$, when present, is selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, $R^{17}$, when present, is selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, $R^{17}$, when present, is selected from hydrogen, C1-C4 hydroxyalkyl, C1-C4 haloalkoxy, and C1-C4 alkoxy. In a further aspect, $R^{17}$, when present, is selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, $R^{17}$, when present, is selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, $R^{17}$, when present, is selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, $R^{17}$, when present, is selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, $R^{17}$, when present, is selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, $R^{17}$, when present, is selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, $R^{17}$, when present, is selected from hydrogen, —F, —Cl, —CN, —NH$_2$, —OH, —NO$_2$, —NHCH$_3$, —N(CH$_3$)$_2$, and —CH$_2$NH$_2$.

In various aspects, $R^{17}$, when present, is selected from hydrogen, C1-C4 alkylamino, (C1-C4)(C1-C4) dialkylamino, and C1-C4 aminoalkyl. In a further aspect, $R^{17}$, when present, is selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, $R^{17}$, when present, is selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, $R^{17}$, when present, is selected from hydrogen, —NHCH$_3$, —N(CH$_3$)$_2$, and —CH$_2$NH$_2$.

In various aspects, $R^{17}$, when present, is selected from hydrogen, halogen, C1-C4 alkyl, C1-C4 haloalkyl, C1-C4 haloalkoxy, and C1-C4 alkoxy. In a further aspect, $R^{17}$, when present, is selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, $R^{17}$, when present, is selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, $R^{17}$, when present, is selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, $R^{17}$, when present, is selected from hydrogen and halogen. In a further aspect, $R^{17}$, when present, is selected from hydrogen, —F, —Cl, and —Br. In a still further aspect, $R^{17}$, when present, is selected from hydrogen, —F, and —Cl. In yet a further aspect, $R^{17}$, when present, is selected from hydrogen and —F. In an even further aspect, $R^{17}$, when present, is selected from hydrogen and —Cl.

In various aspects, $R^{17}$, when present, is selected from hydrogen, —CO$_2$H, and —CO$_2$(C1-C4 alkyl). In a further aspect, $R^{17}$, when present, is selected from hydrogen, —CO$_2$H, —CO$_2$CH$_3$, —CO$_2$CH$_2$CH$_3$, —CO$_2$CH$_2$CH$_2$CH$_3$, and —CO$_2$CH(CH$_3$)$_2$. In a still further aspect, R$^{17}$, when present, is selected from hydrogen, —CO$_2$H, —CO$_2$CH$_3$, and —CO$_2$CH$_2$CH$_3$. In yet a further aspect, R$^{17}$, when present, is selected from hydrogen, —CO$_2$H, and —CO$_2$CH$_3$.

In various aspects, R$^{17}$, when present, is hydrogen.

l. R$^{20}$ Groups

In one aspect, R$^{20}$, when present, is selected from hydrogen and C1-C4 alkyl. In a further aspect, R$^{20}$, when present, is selected from hydrogen, methyl, ethyl, n-propyl, and isopropyl. In a still further aspect, R$^{20}$, when present, is selected from hydrogen, methyl, and ethyl. In yet a further aspect, R$^{20}$, when present, is selected from hydrogen and ethyl. In an even further aspect, R$^{20}$, when present, is selected from hydrogen and methyl.

In various aspects, R$^{20}$, when present, is C1-C4 alkyl. In a further aspect, R$^{20}$, when present, is selected from methyl, ethyl, n-propyl, and isopropyl. In a still further aspect, R$^{20}$, when present, is selected from methyl and ethyl. In yet a further aspect, R$^{20}$, when present, is ethyl. In an even further aspect, R$^{20}$, when present, is methyl.

In a further aspect, R$^{20}$, when present, is hydrogen.

m. R$^{21}$ Groups

In one aspect, R$^{21}$, when present, is selected from hydrogen and C1-C4 alkyl. In a further aspect, R$^{21}$, when present, is selected from hydrogen, methyl, ethyl, n-propyl, and isopropyl. In a still further aspect, R$^{21}$, when present, is selected from hydrogen, methyl, and ethyl. In yet a further aspect, R$^{21}$, when present, is selected from hydrogen and ethyl. In an even further aspect, R$^{21}$, when present, is selected from hydrogen and methyl.

In various aspects, R$^{21}$, when present, is C1-C4 alkyl. In a further aspect, R$^{21}$, when present, is selected from methyl, ethyl, n-propyl, and isopropyl. In a still further aspect, R$^{21}$, when present, is selected from methyl and ethyl. In yet a further aspect, R$^{21}$, when present, is ethyl. In an even further aspect, R$^{21}$, when present, is methyl.

In a further aspect, R$^{21}$, when present, is hydrogen.

n. CY$^1$ Groups

In one aspect, Cy$^1$ is a structure having a formula selected from:

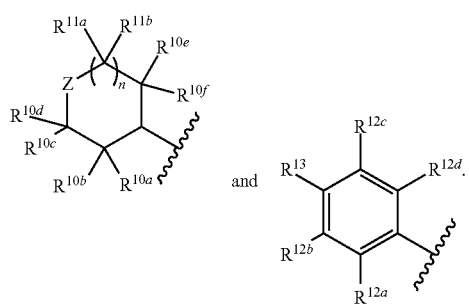

In a further aspect, Cy$^1$ is a structure having a formula:

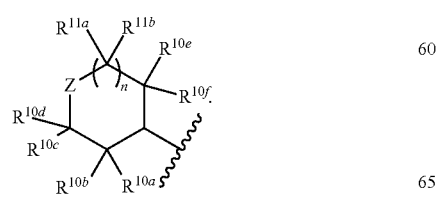

In a further aspect, Cy$^1$ is a structure having a formula:

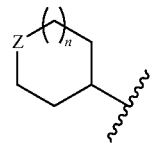

In a further aspect, Cy$^1$ is a structure having a formula selected from:

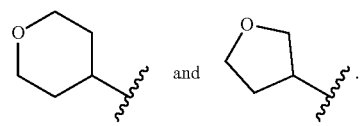 [SMILES: *C1CCOCC1 ; *C1CCOC1]

In a further aspect, Cy$^1$ is a structure having a formula:

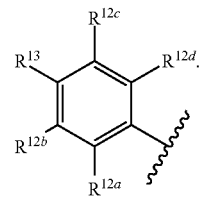

In a further aspect, Cy$^1$ is a structure having a formula:

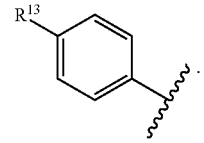

o. CY$^2$ Groups

In one aspect, Cy$^2$ is a structure having a formula selected from:

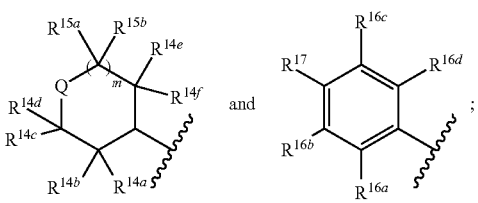

In a further aspect, Cy$^2$ is a structure having a formula:

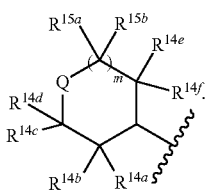

In a further aspect, Cy² is a structure having a formula:
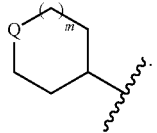
In a further aspect, Cy² is a structure having a formula:
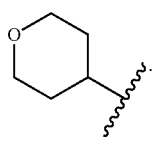
In a further aspect, Cy² is a structure having a formula:
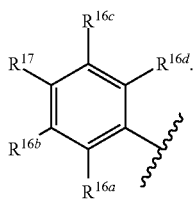
In a further aspect, Cy² is a structure having a formula:
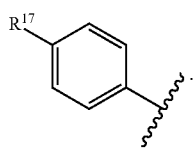
2. Example Purine Diamines
In one aspect, a compound can be present as:
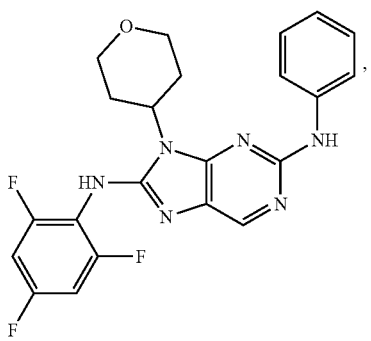
-continued
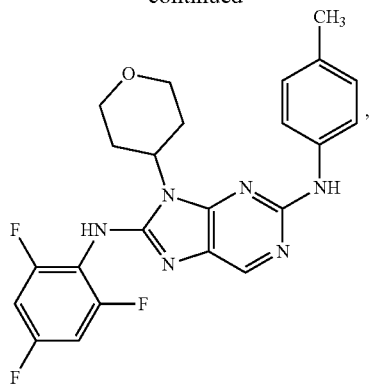
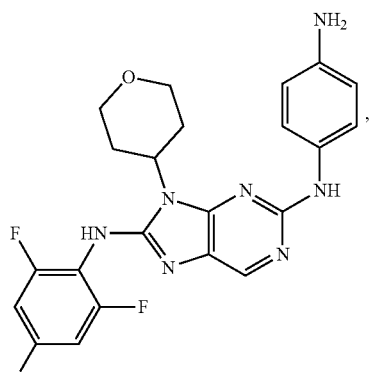
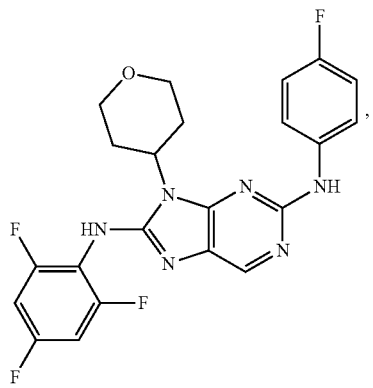
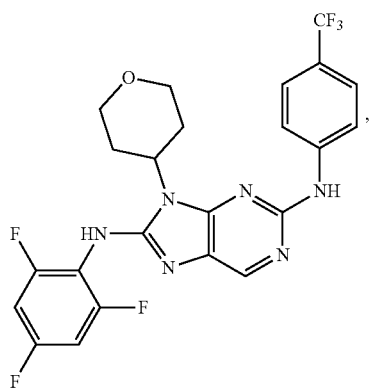

-continued
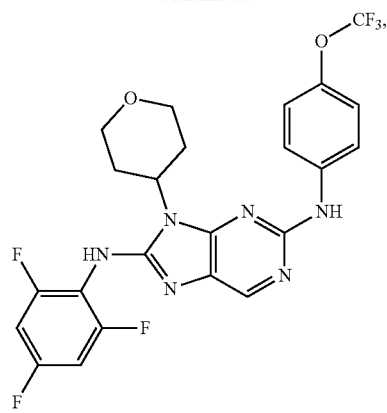
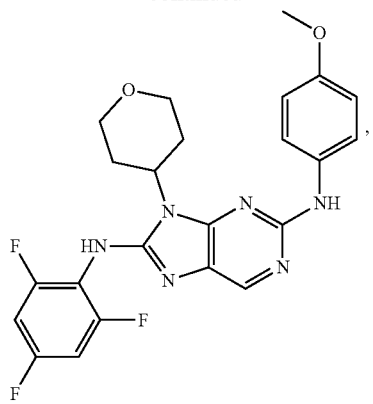
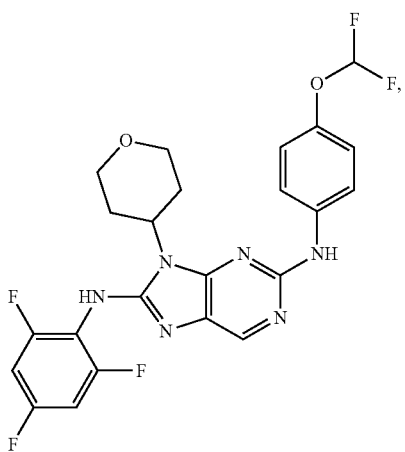
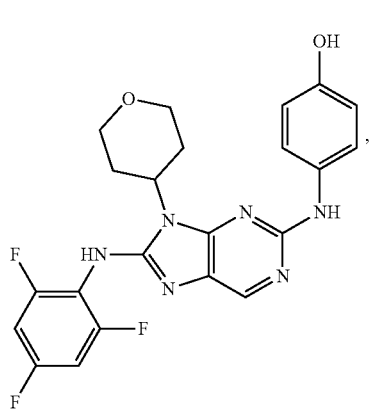
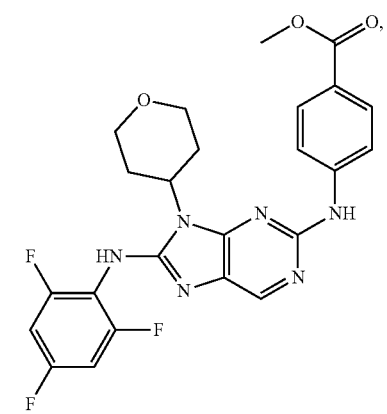
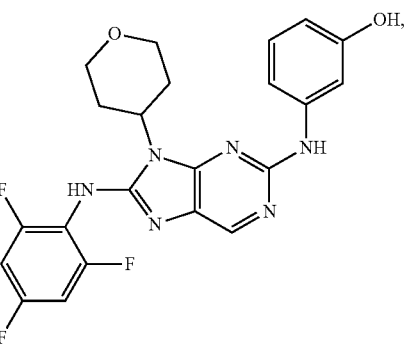
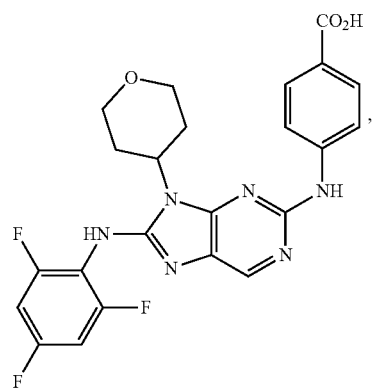
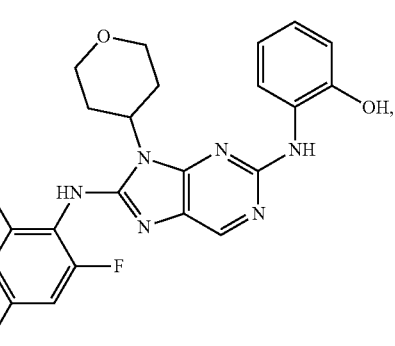

-continued
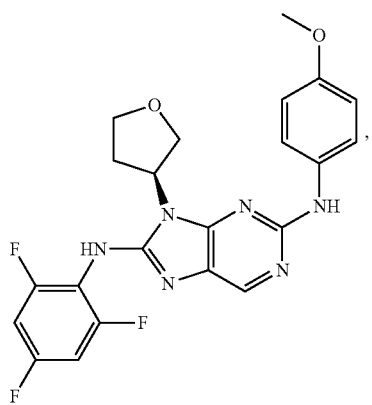
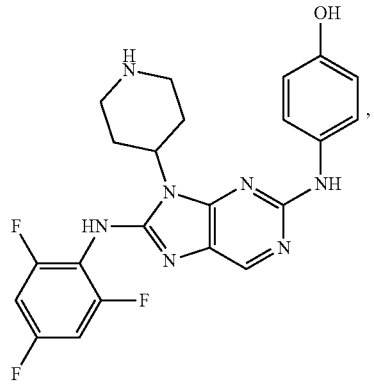
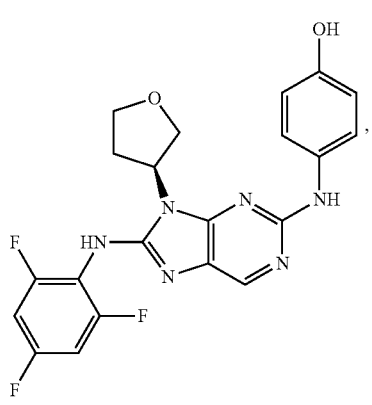
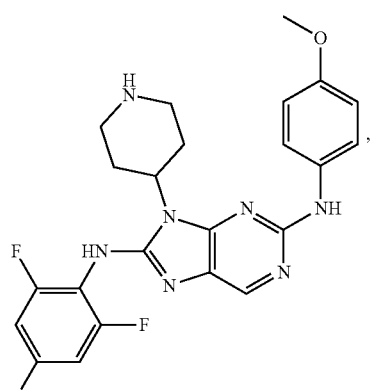
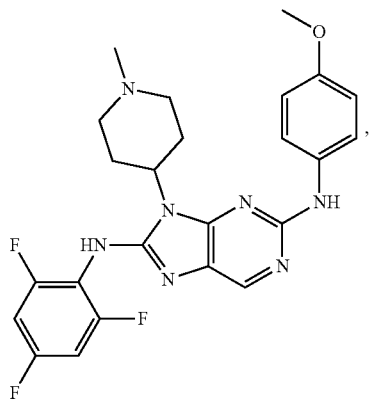
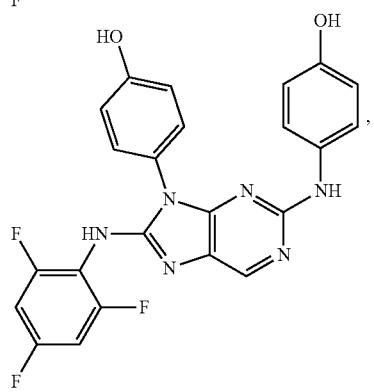
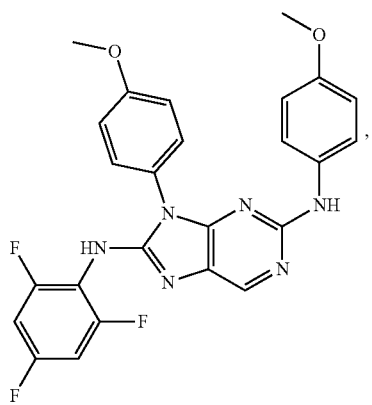
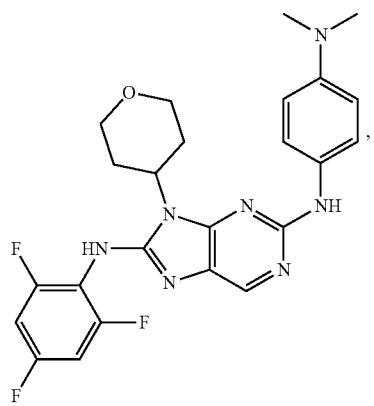

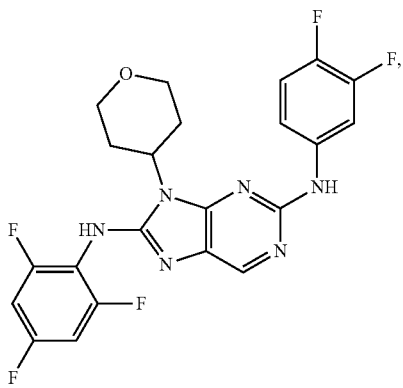

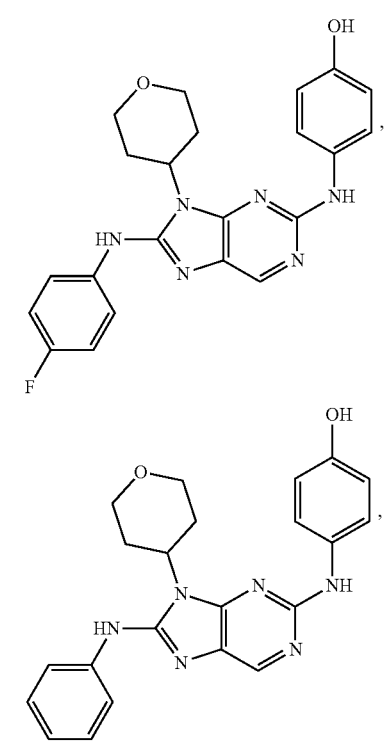

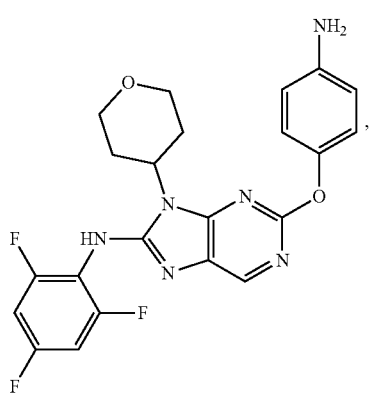

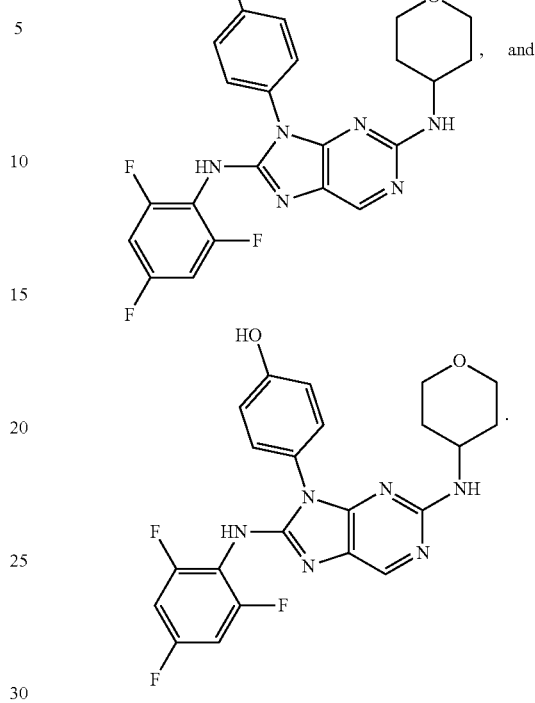

or a pharmaceutically acceptable salt thereof.

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, disclosed are pharmaceutical compositions comprising an effective amount of a disclosed compound and a pharmaceutically acceptable carrier.

Thus, in one aspect, disclosed are pharmaceutical compositions comprising a therapeutically effective amount of a compound having a structure represented by a formula:

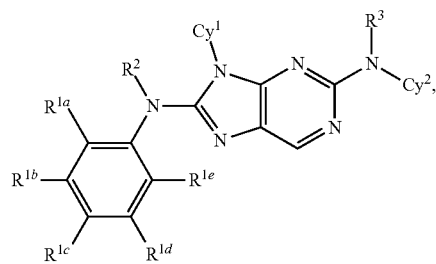

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

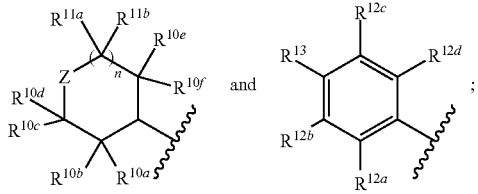

wherein n, when present, is 0 or 1; wherein Z, when present, is selected from —O—, —S—, and —NR$^{20}$—; wherein $R^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

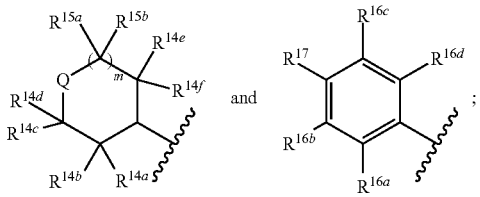

wherein m, when present, is 0 or 1; wherein Q, when present, is selected from —O—, —S—, and —NR$^{21}$—; wherein $R^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), provided that when Cy$^1$ is

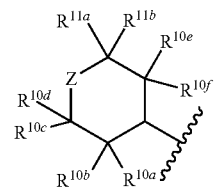

and at least seven of $R^{10a}$, $R^{10b}$, $R^{10c}$, $R^{10d}$, $R^{10e}$, $R^{10f}$, $R^{11a}$, and $R^{11b}$ are hydrogen, and when Cy$^2$ is

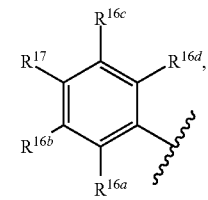

then either: (a) each of $R^{1a}$, $R^{1c}$, and $R^{1e}$ is halogen; or (b) Z is —O—, each of $R^{16a}$, $R^{16b}$, $R^{16c}$, and $R^{16d}$ is hydrogen, and $R^{17}$ is —OH, —NH$_2$, C1-C4 alkoxy, C1-C4 alkylamino, or (C1-C4)(C1-C4) dialkylamino, provided that when Cy$^1$ is

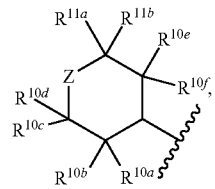

then Cy$^2$ is

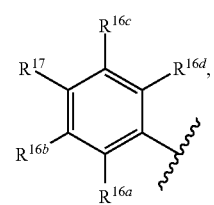

provided that when Cy¹ is

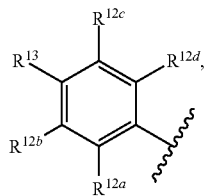

and Cy² is

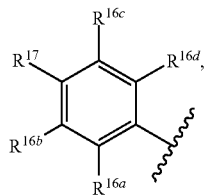

then R¹⁷ is a non-hydrogen group, and provided that when Cy¹ is

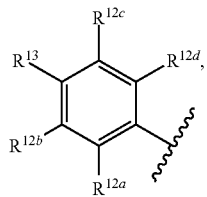

Cy² is

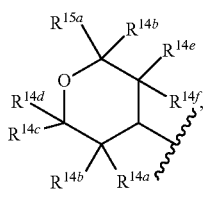

and at least seven of $R^{14a}$, $R^{14b}$, $R^{14c}$, $R^{14d}$, $R^{14e}$, $R^{14f}$, $R^{15a}$, and $R^{15b}$ are hydrogen, then each of $R^{12a}$, $R^{12b}$, $R^{12c}$ and $R^{12d}$ is hydrogen, or a pharmaceutically acceptable salt thereof, and a pharmaceutically acceptable carrier.

In various aspects, disclosed are pharmaceutical compositions comprising an effective amount of a compound selected from:

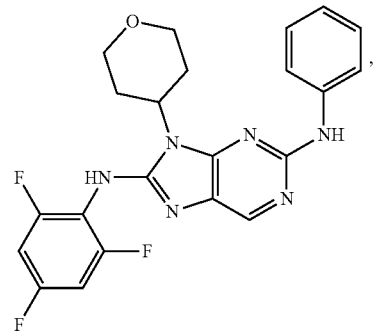

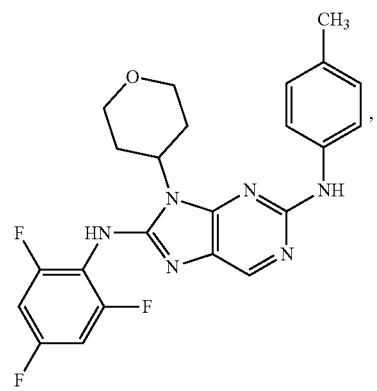

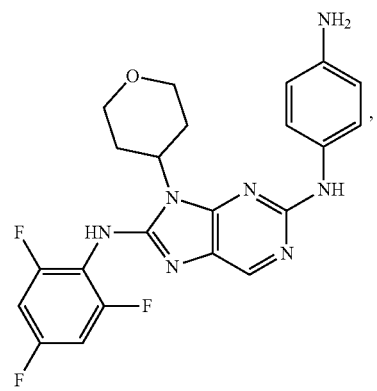

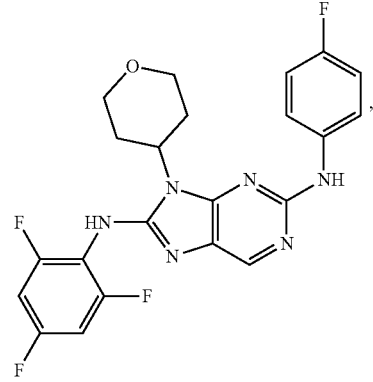

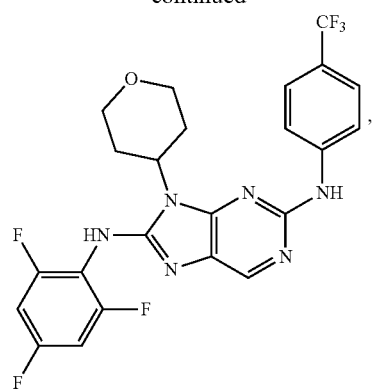
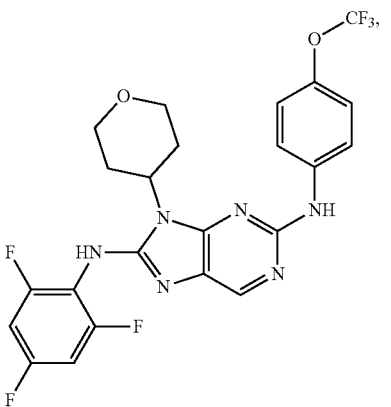
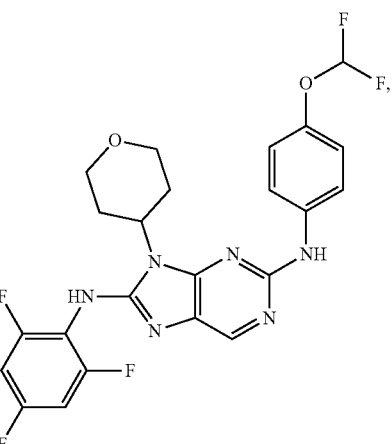
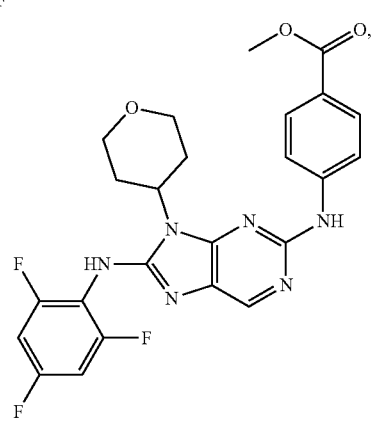
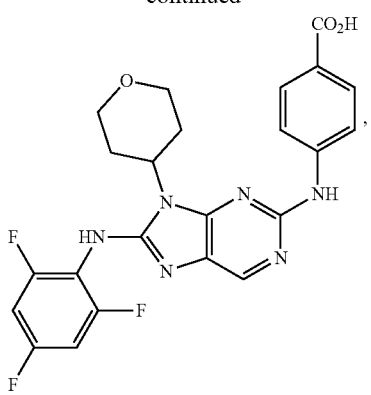
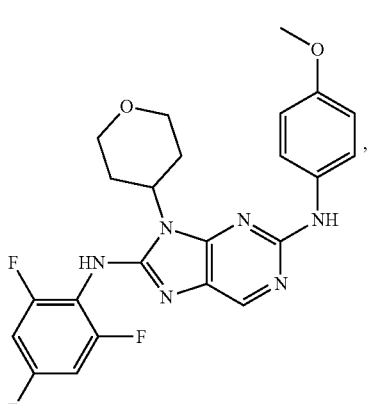
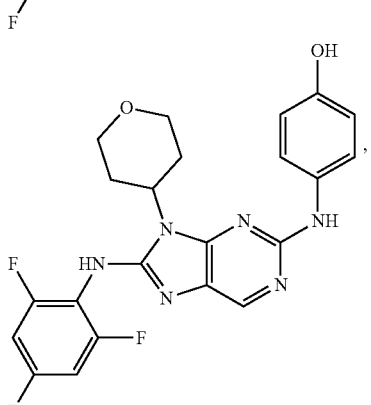
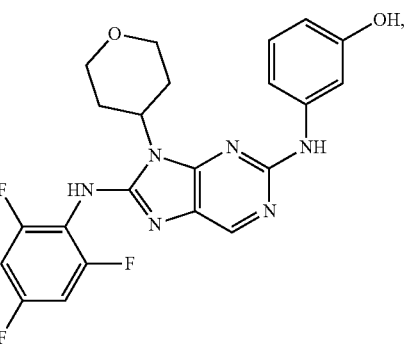

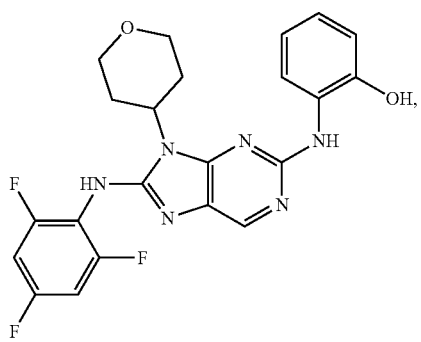
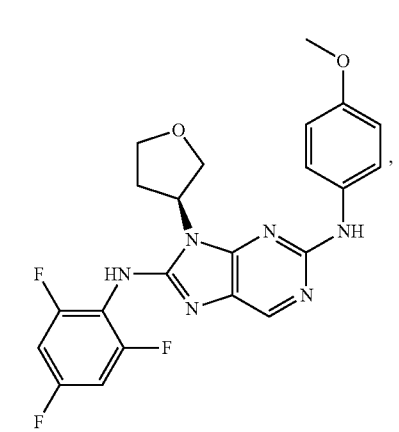
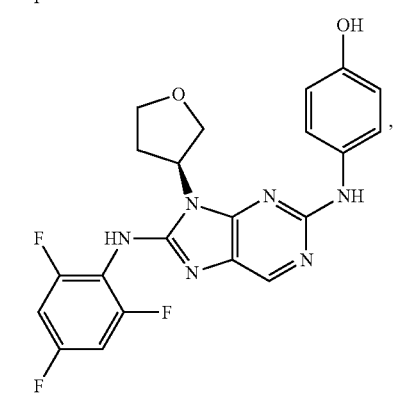
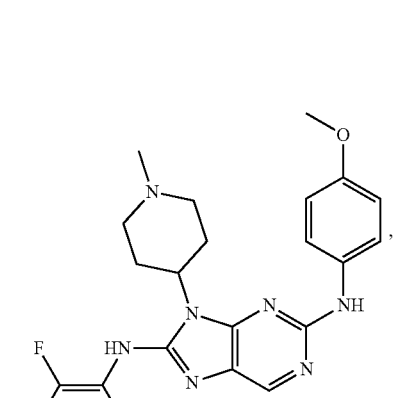
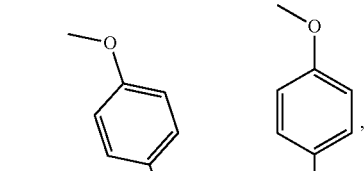
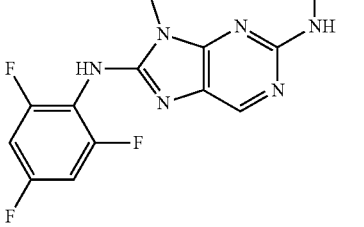
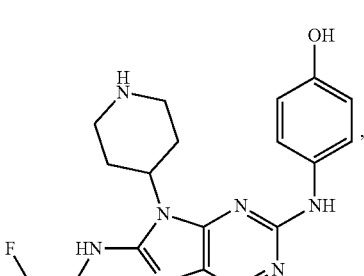
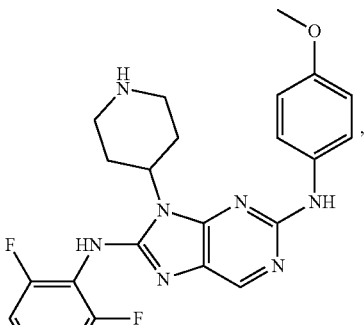
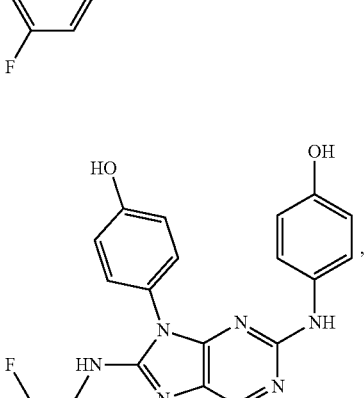

93
-continued
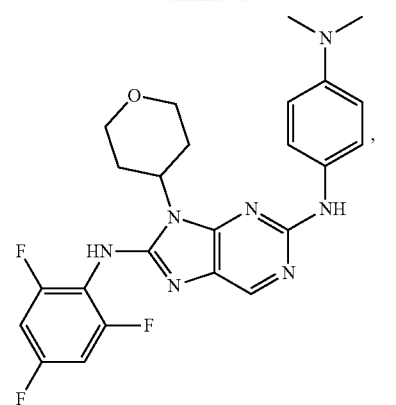
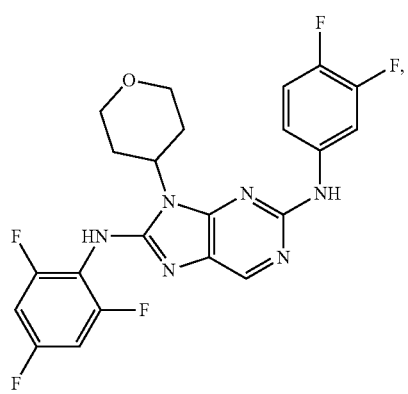
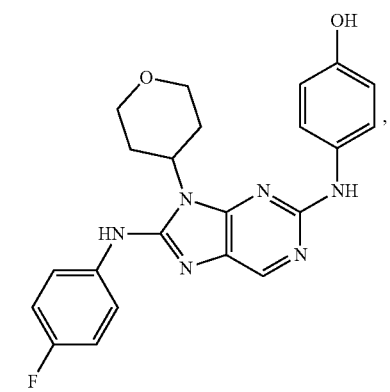
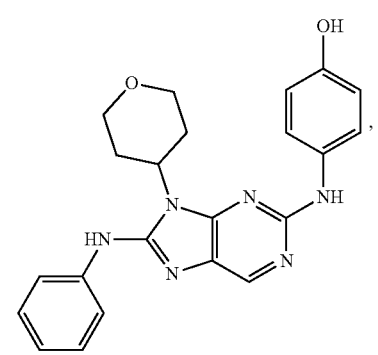
94
-continued
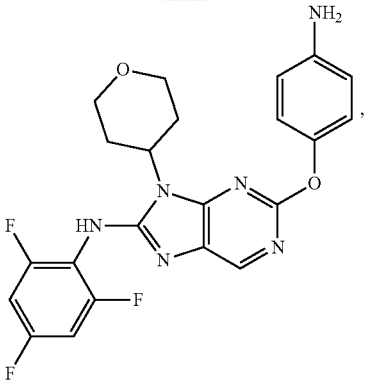
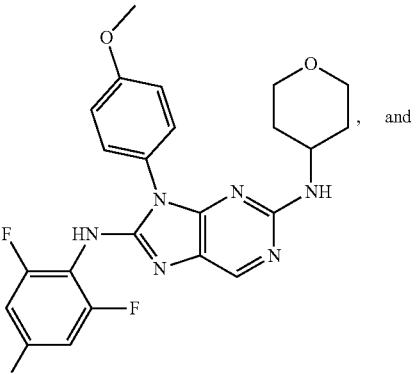
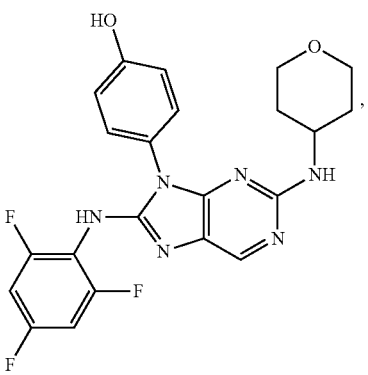
or a pharmaceutically acceptable salt thereof, and a pharmaceutically acceptable carrier.
In various aspects, the compound has a structure represented by a formula:
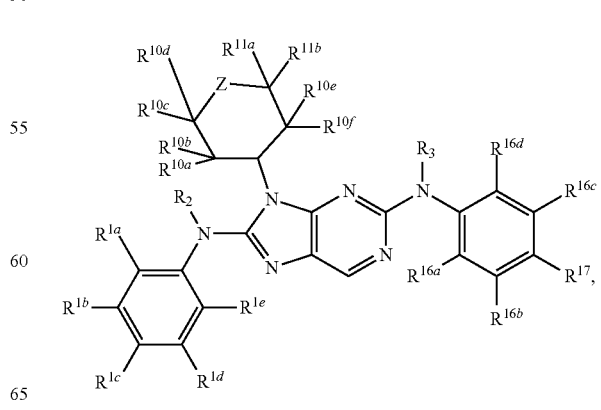
wherein each of $R^{1a}$, $R^{1c}$, and $R^{1e}$ is halogen.

In various aspects, the compound has a structure represented by a formula:

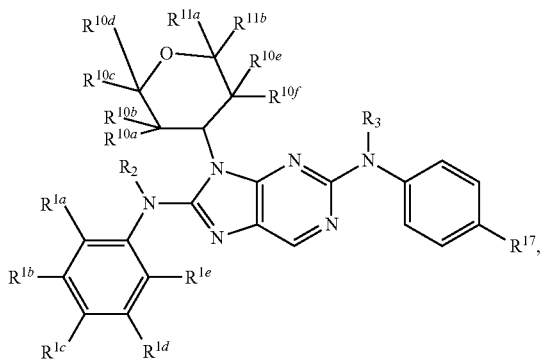

wherein $R^{17}$ is selected from —OH, —NH$_2$, C1-C4 alkoxy, C1-C4 alkylamino, and (C1-C4)(C1-C4) dialkylamino.

In various aspects, the compound has a structure represented by a formula:

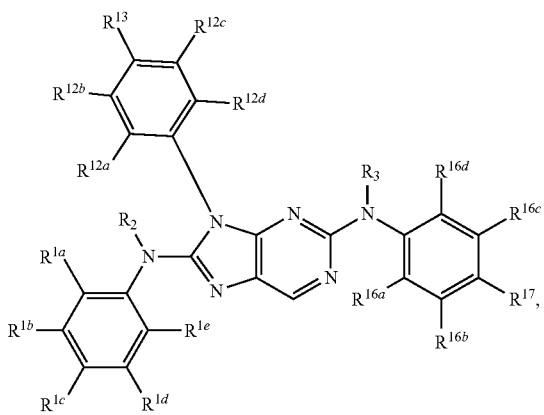

wherein $R^{17}$, when present, is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl).

In various aspects, the compound has a structure represented by a formula:

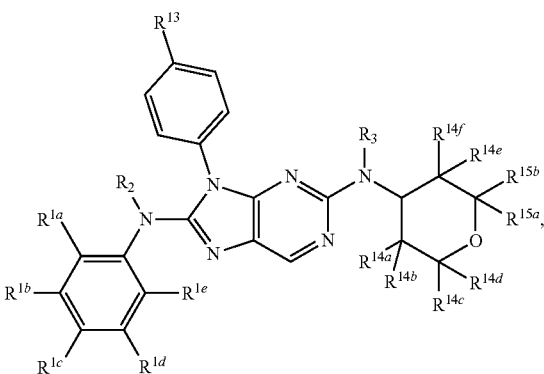

wherein one of $R^{14a}$, $R^{14b}$, $R^{14c}$, $R^{14d}$, $R^{14e}$, $R^{14f}$, $R^{15a}$, and $R^{15b}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein the remaining $R^{14a}$, $R^{14b}$, $R^{14c}$, $R^{14d}$, $R^{14e}$, $R^{14f}$, $R^{15a}$, and $R^{15b}$ groups are hydrogen.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a condition associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters.

It is understood that the disclosed compositions can be prepared from the disclosed compounds. It is also understood that the disclosed compositions can be employed in the disclosed methods of using.

D. Methods of Making Purine Diamines

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-II, as described and exemplified below. The following examples are provided so that the invention might be more fully understood, are illustrative only, and should not be construed as limiting.

1. Route I

In one aspect, substituted purine diamines can be prepared as shown below.

SCHEME 1A.

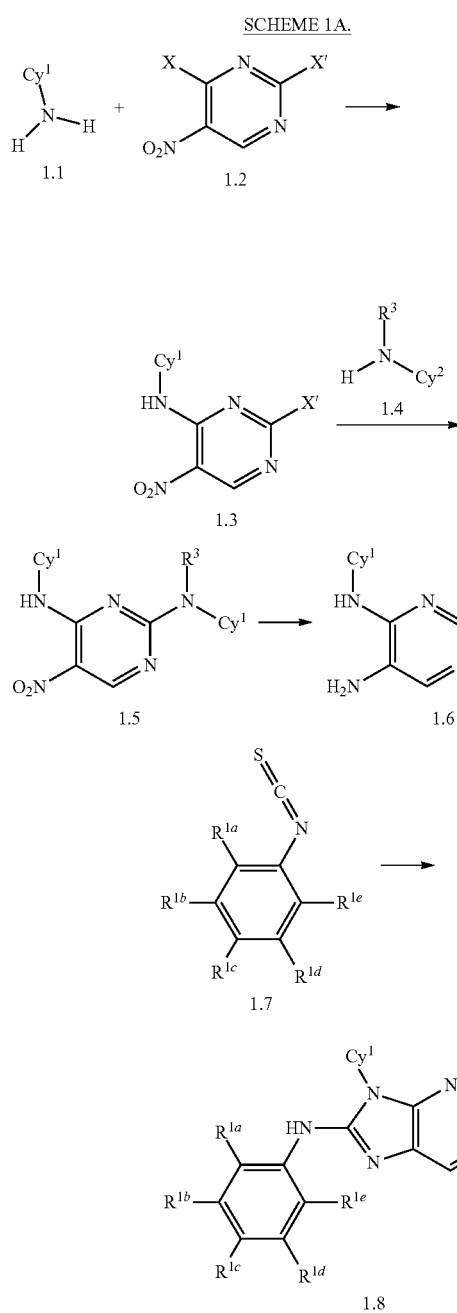

Compounds are represented in generic form, where X and X' are independently halogen, and with other substituents as noted in compound descriptions elsewhere herein. A more specific example is set forth below.

SCHEME 1B.

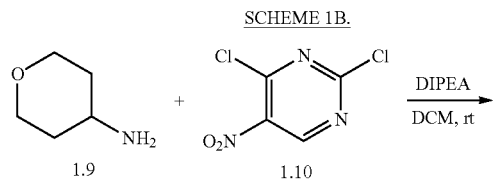

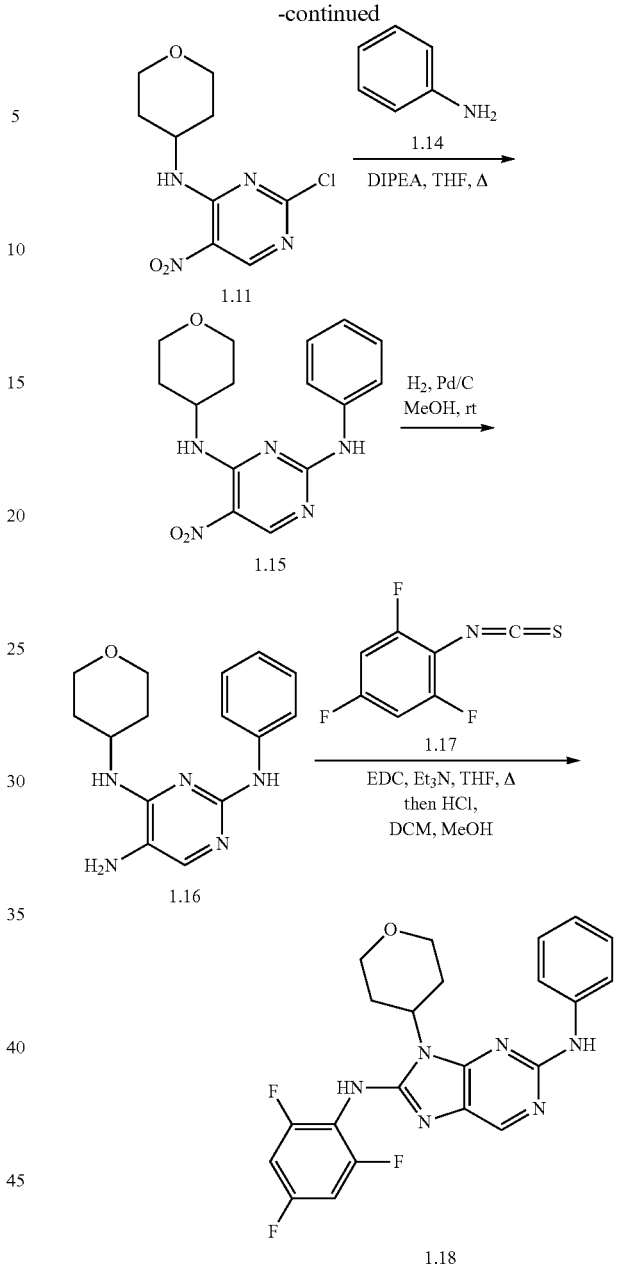

In one aspect, compounds of type 1.18, and similar compounds, can be prepared according to reaction Scheme 1B above. Thus, compounds of type 1.11 can be prepared by a coupling reaction between an appropriate amine, e.g., 1.9 as shown above, and an appropriate halopyrimidine, e.g., 1.10 as shown above. Appropriate amines and appropriate pyrimidines are commercially available or prepared by methods known to one skilled in the art. The coupling reaction is carried out in the presence of an appropriate base, e.g., N,N-diisopropylethylamine (DIPEA), in an appropriate solvent, e.g., dichloromethane. Compounds of type 1.15 can be prepared by a coupling reaction between an appropriate halopyrimidine, e.g., 1.11 as shown above, and an appropriate amine, e.g., 1.14 as shown above. Appropriate amines are commercially available or prepared by methods known to one skilled in the art. The coupling reaction is carried out in the presence of an appropriate base, e.g., DIPEA, in an appropriate solvent, e.g., tetrahydrofuran. Compounds of type 1.16 can be prepared by reduction of an appropriate nitro analog, e.g., 1.15 as shown above. The reduction is carried out in the presence of an appropriate hydide source, e.g., hydrogen gas, and an appropriate catalyst, e.g., palladium on carbon, in an appropriate solvent, e.g., methanol. Compounds of type 1.18 can be prepared by cyclization of an appropriate diamine, e.g., 1.16 as shown above. The cyclization is carred out in the presence of an appropriate thiocyanate, e.g., 1.17 as shown above, an appropriate activating agent, e.g., 1-ethyl-3-(3-dimethylaminopropyl) carbodiimide (EDC), and an appropriate base, e.g., triethylamine, in an appropriate solvent, e.g., tetrahydrofuran, followed by addition of an appropriate acid, e.g. hydrochloric acid, in an appropriate solvent, e.g., dichloromethane and methanol. Appropriate thiocyanates are commercially available or prepared by methods known to one skilled in the art. As can be appreciated by one skilled in the art, the above reaction provides an example of a generalized approach wherein compounds similar in structure to the specific reactants above (compounds similar to compounds of type 1.1, 1.2, 1.3, 1.4, 1.5, 1.6, and 1.7), can be substituted in the reaction to provide substituted purine diamine derivatives similar to Formula 1.8.

2. Route II

In one aspect, substituted purine diamines can be prepared as shown below.

SCHEME 2A.

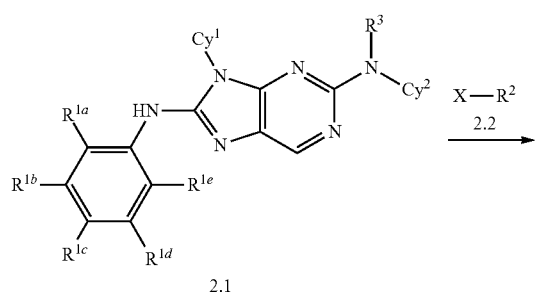

2.1

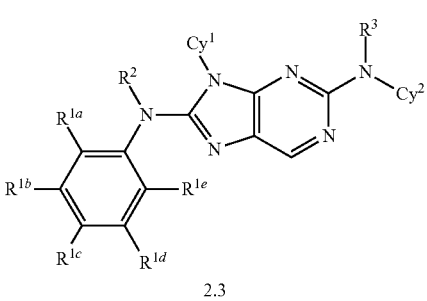

2.3

Compounds are represented in generic form, where X is a halogen, and with other substituents as noted in compound descriptions elsewhere herein. A more specific example is set forth below.

SCHEME 2B.

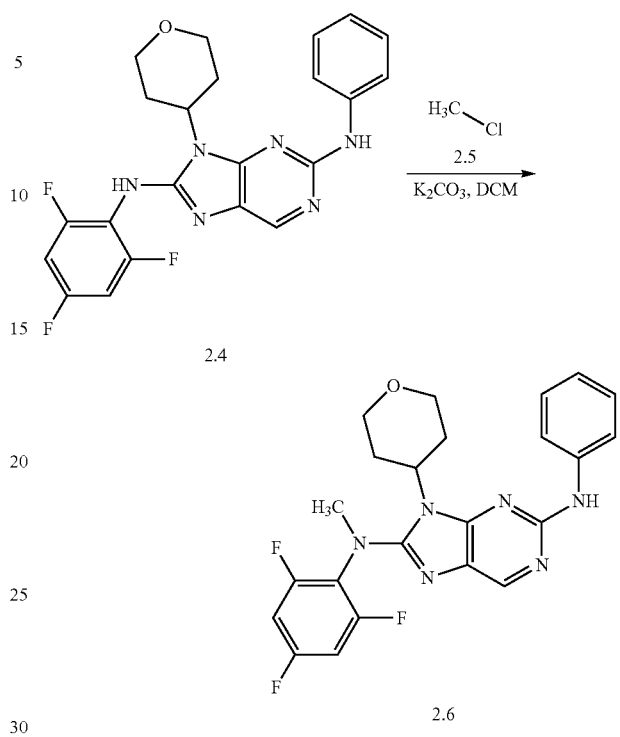

In one aspect, compounds of type 2.6, and similar compounds, can be prepared according to reaction Scheme 2B above. Thus, compounds of type 2.6 can be prepared by alkylation of an appropriate amine, e.g., 2.5 as shown above. The alkylation is carried out in the presence of an appropriate alkyl halide, e.g., 2.5 as shown above, and an appropriate base, e.g., potassium carbonate, in an appropriate solvent, e.g., dichloromethane. Appropriate alkyl halides are commercially available or prepared by methods known to one skilled in the art. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted purine diamine derivatives similar to Formula 2.3.

E. Treating a Condition Associated with BRD4, RIP3K, and/or IL6 Signaling

In one aspect, disclosed are methods of treating a condition associated with signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a disclosed compound, thereby treating the condition.

Thus, in one aspect, disclosed are methods of treating a condition associated with signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure represented by a formula:

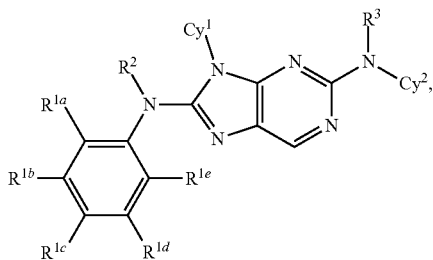

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

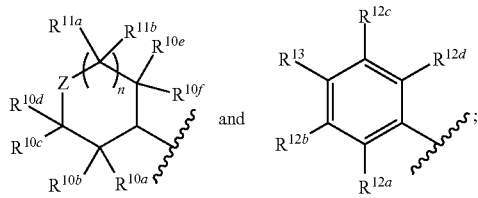

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

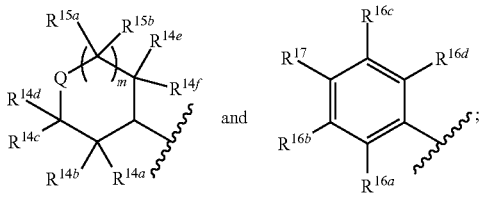

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), or a pharmaceutically acceptable salt thereof, thereby treating the condition.

Also disclosed are methods of treating a condition associated with signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure represented by a formula:

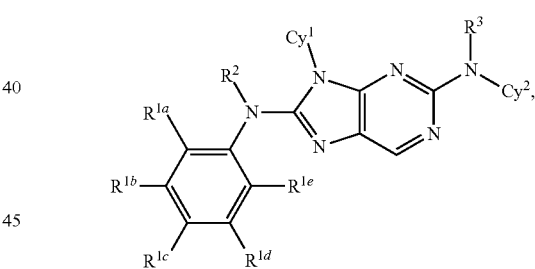

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

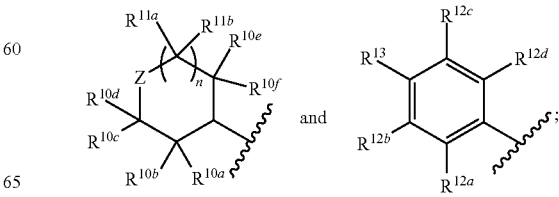

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of R$^{10a}$, R$^{10b}$, R$^{10c}$, R$^{10d}$, R$^{10e}$, and R$^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{11a}$ and R$^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{12a}$, R$^{12b}$, R$^{12c}$, and R$^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

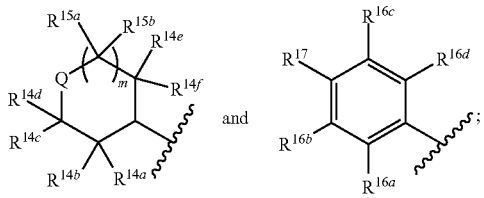

and wherein m, when present, is 0 or 1; wherein Q, when present, is selected from —O—, —S—, and —NR$^{21}$—; wherein R$^{21}$, when present, is selected from hydrogen and C1-C4 alkyl; wherein each of R$^{14a}$, R$^{14b}$, R$^{14c}$, R$^{14d}$, R$^{14e}$, and R$^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{15a}$ and R$^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$, R$^{16b}$, R$^{16c}$, and R$^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), provided that when Cy$^1$ is

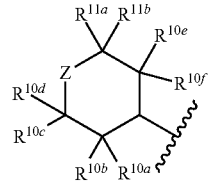

and at least seven of R$^{10a}$, R$^{10b}$, R$^{10c}$, R$^{10d}$, R$^{10e}$, R$^{10f}$, R$^{11a}$, and R$^{11b}$ are hydrogen, and when Cy$^2$ is

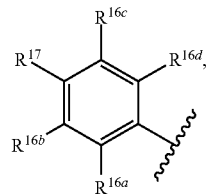

then either: (a) each of R$^{1a}$, R$^{1c}$, and R$^e$ is halogen; or (b) Z is —O—, each of R$^{16a}$, R$^{16b}$, R$^{16c}$, and R$^{16d}$ is hydrogen, and R$^{17}$ is —OH, —NH$_2$, C1-C4 alkoxy, C1-C4 alkylamino, or (C1-C4)(C1-C4) dialkylamino, provided that when Cy$^1$ is

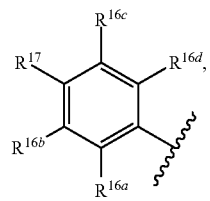

then Cy$^2$ is

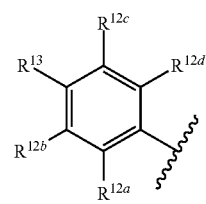

provided that when Cy$^1$ is

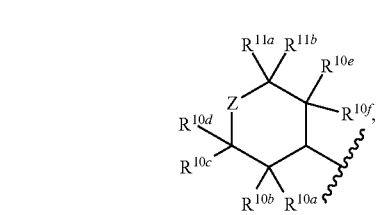

and Cy² is

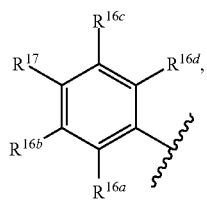

then R¹⁷ is a non-hydrogen group, and provided that when Cy¹ is

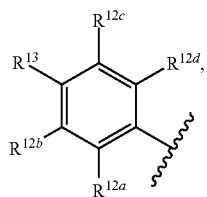

Cy² is

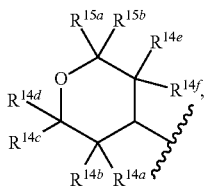

R¹⁴ᵃ, and at least seven of R¹⁴ᵃ, R¹⁴ᵇ, R¹⁴ᶜ, R¹⁴ᵈ, R¹⁴ᵉ, R¹⁴ᶠ, R¹⁵ᵃ, and R¹⁵ᵇ are hydrogen, then each of R¹²ᵃ, R¹²ᵇ, R¹²ᶜ and R¹²ᵈ is hydrogen, or a pharmaceutically acceptable salt thereof, thereby treating the condition.

Also disclosed are methods of treating a condition associated with signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure selected from:

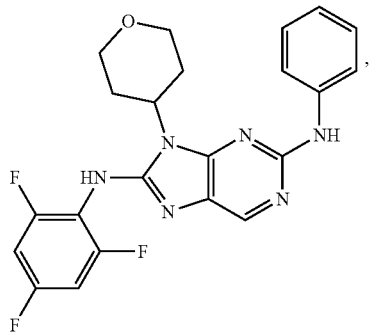

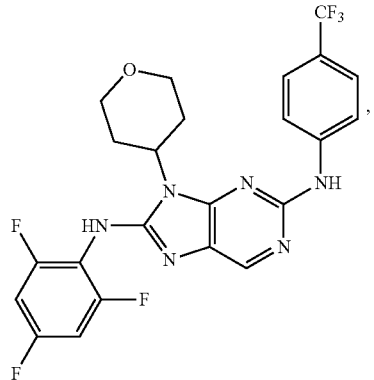

109
-continued
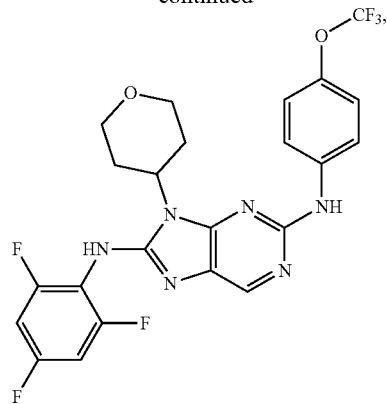
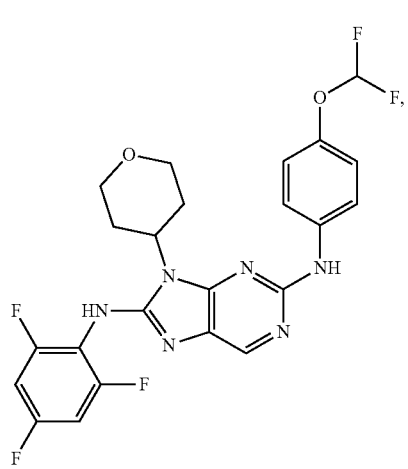
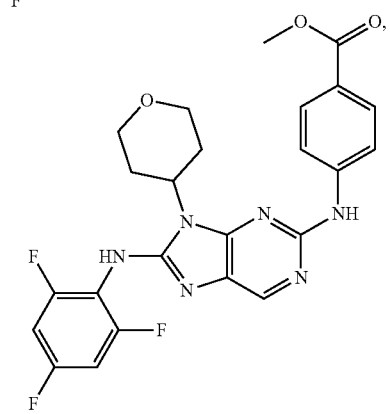
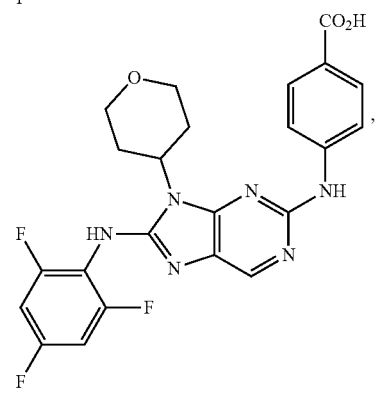
110
-continued
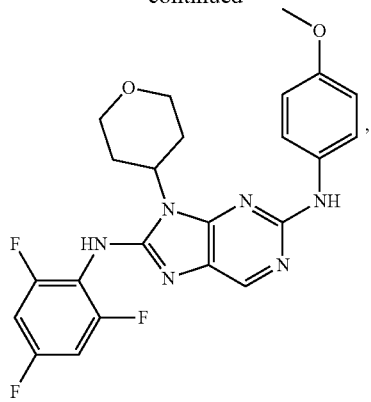
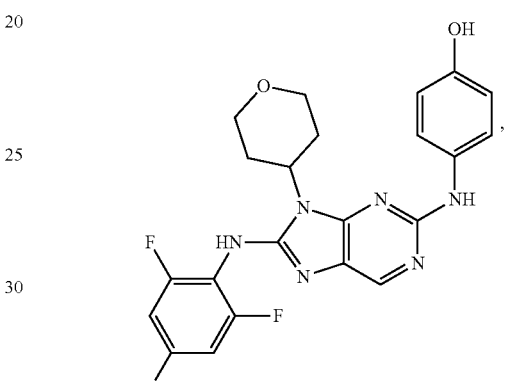
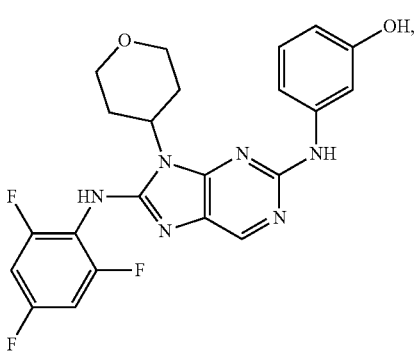
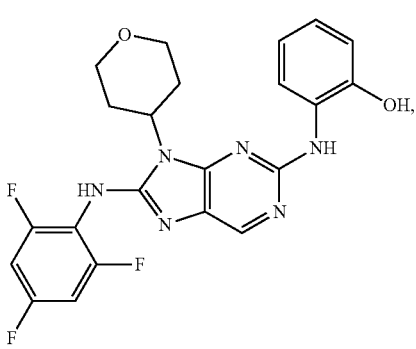

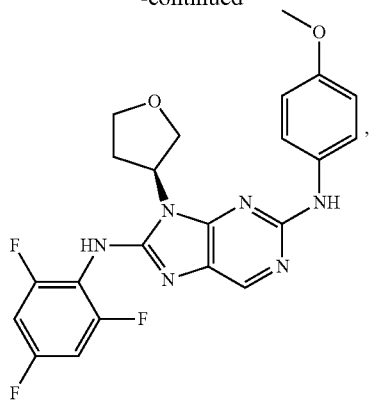
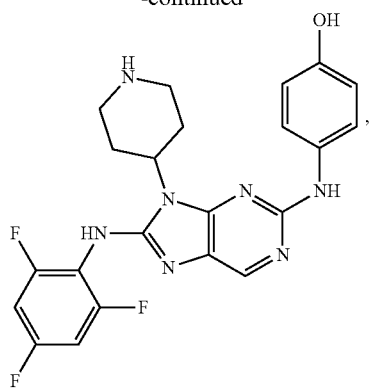
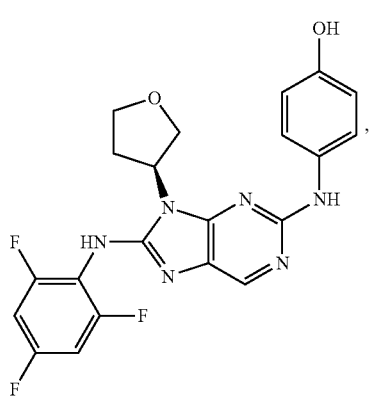
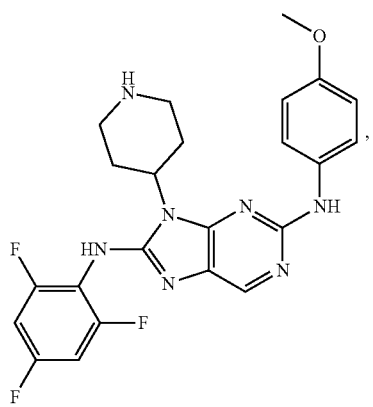
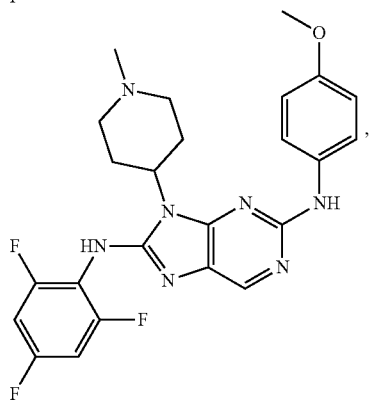
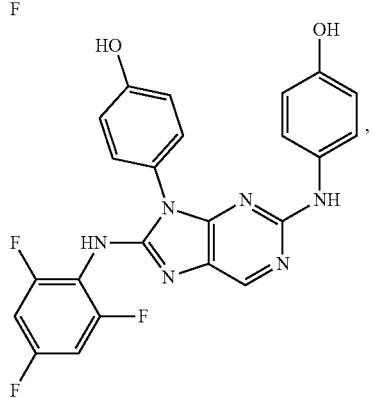
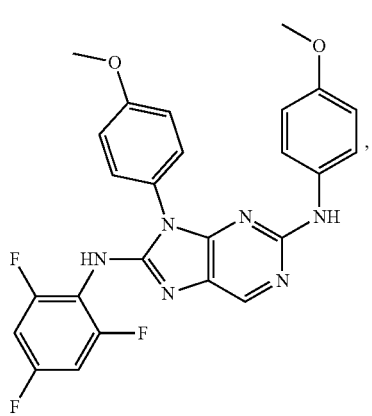
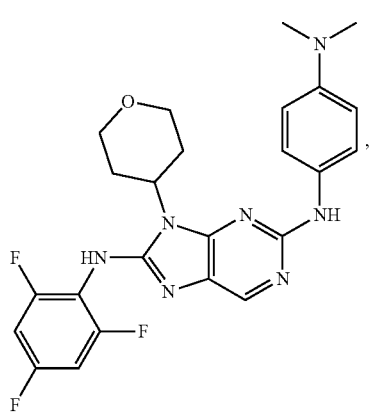

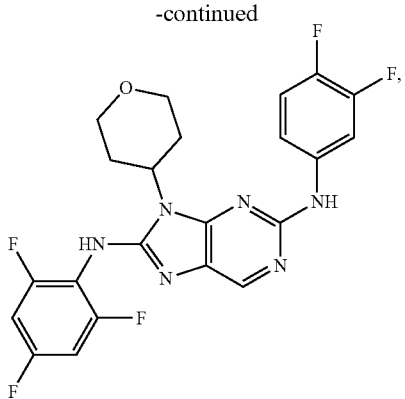
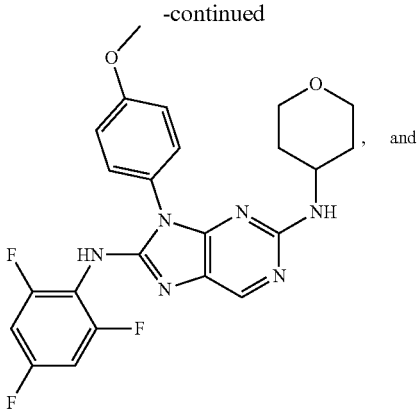
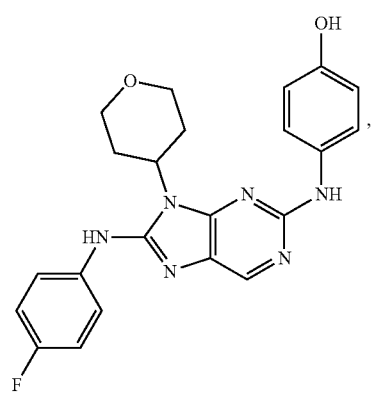
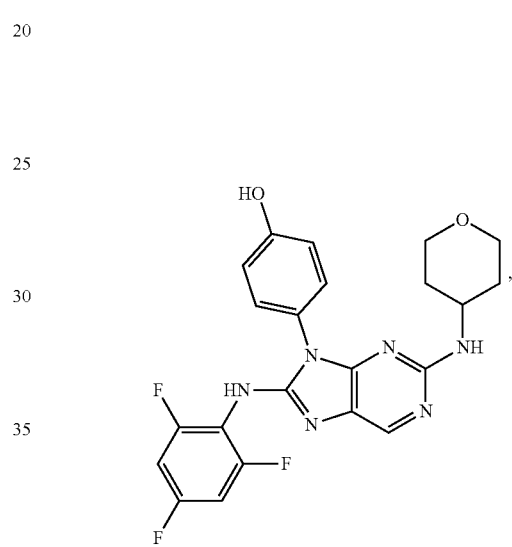
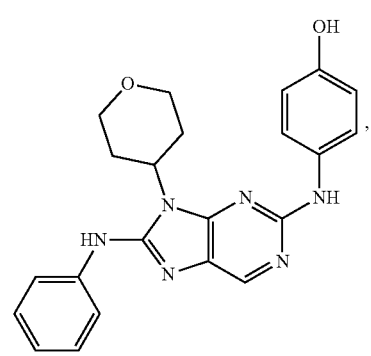
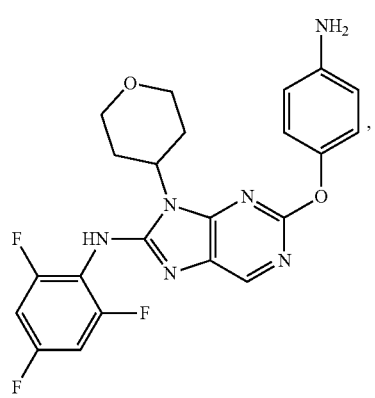
or a pharmaceutically acceptable salt thereof, thereby treating the condition.
In various aspects, the compound has a structure represented by a formula:
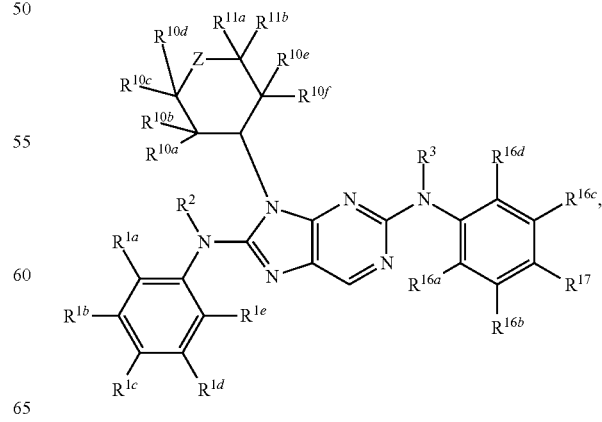
wherein each of $R^{1a}$, $R^{1c}$, and $R^{1e}$ is halogen.

In various aspects, the compound has a structure represented by a formula:

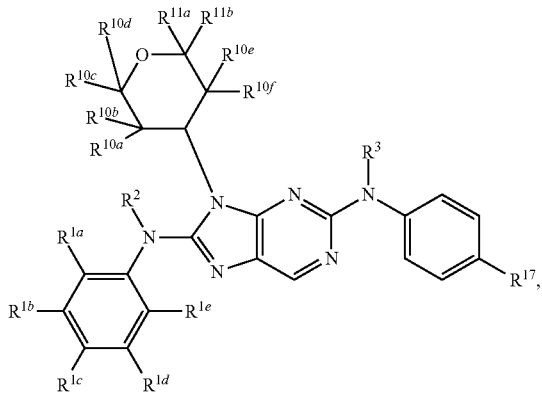

wherein $R^{17}$ is selected from —OH, —NH$_2$, C1-C4 alkoxy, C1-C4 alkylamino, and (C1-C4)(C1-C4) dialkylamino.

In various aspects, the compound has a structure represented by a formula:

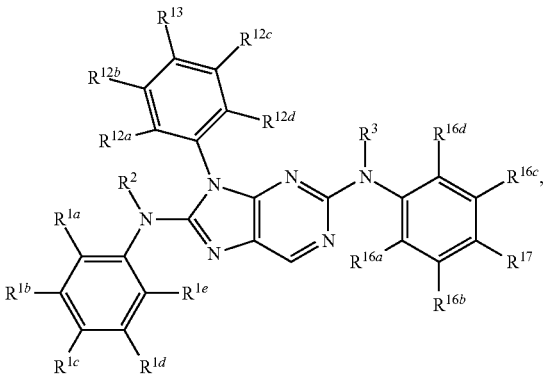

wherein $R^{17}$, when present, is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl).

In various aspects, the compound has a structure represented by a formula:

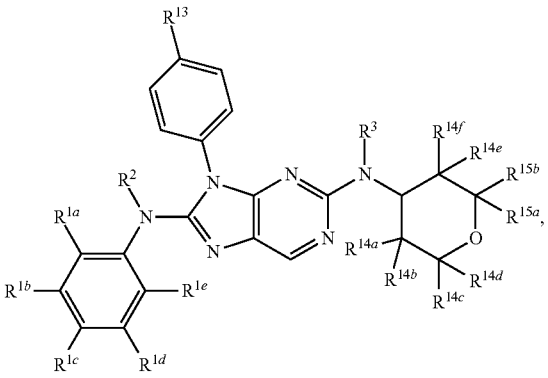

wherein one of $R^{14a}$, $R^{14b}$, $R^{14c}$, $R^{14d}$, $R^{14e}$, $R^{14f}$, $R^{15a}$, and $R^{15b}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein the remaining $R^{14a}$, $R^{14b}$, $R^{14c}$, $R^{14d}$, $R^{14e}$, $R^{14f}$, $R^{15a}$, and $R^{15b}$ groups are hydrogen.

In a further aspect, the condition associated with BRD4, RIP3K, and/or IL6 signaling dysfunction is due to exposure to an arsenical. Examples of arsenicals include, but are not limited to, arsanilic acid, arsenic, arsenic (V) pentoxide, arsenic (III) sulfide, arsenic (III) trichloride, arsenobetaine, arsine, calcium arsenate, dimethylarsinic acid, lead arsenate, methanearsonic acid, potassium arsenate, potassium arsenite, sodium arsenate, sodium arsenite, sodium cacodylate, arsenic trioxide, methylarsonic acid, dimethylarsinic acid, lewisite, diphenylchlorarsine, diphenylcyanoarsine, diethylchloroarsine, phenylarsine oxide, and arsenobetaine.

In various aspects, exposure is via ingestion, inhalation, and/or absorption through a mucosal membrane (e.g., eyes, lips). In various further aspects, exposure is dermal exposure.

In a further aspect, the condition associated with BRD4, RIP3K, and/or IL6 signaling dysfunction is inflammation, skin lesions, dysfunction of systemic organs, and/or skin blisters.

In a further aspect, the condition associated with BRD4, RIP3K, and/or IL6 signaling dysfunction is arsenicosis or arsenic poisoning.

In a further aspect, the condition associated with BRD4, RIP3K, and/or IL6 signaling dysfunction is cancer. Examples of cancers include, but are not limited to, lung cancer, skin cancer, bladder cancer, kidney cancer, or liver cancer. In a still further aspect, the cancer is induced by arsenicals and/or other environmental agents.

In a further aspect, the condition associated with BRD4, RIP3K, and/or IL6 signaling dysfunction is acute lung injury (ALI), acute kidney injury (AKI), chronic kidney disease (CKD), liver damage, neurological alterations, immune dysregulation, or ocular damages including blindness.

In a further aspect, the subject has been diagnosed with a need for treatment of the condition prior to the administering step. In a still further aspect, the subject is at risk for developing the condition prior to the administering step.

In a further aspect, the subject is a mammal. In a still further aspect, the mammal is a human.

In a further aspect, the method further comprises the step of identifying a subject in need of treatment of the condition.

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a condition associated with BRD4, RIP3K, and/or IL6 signaling dysfunction. In a still further aspect, the agent is a chelating agent, a retinoid, vitamin E, selenium, N-acetylcysteine, or 4-phenylbutyric acid.

In a further aspect, administering is via topical or systemic administration.

In a further aspect, the compound and the agent are administered sequentially. In a still further aspect, the compound and the agent are administered simultaneously.

In a further aspect, the compound and the agent are co-formulated. In a still further aspect, the compound and the agent are co-packaged.

In a further aspect, the compound is administered as a single active agent.

F. Modifying BRD4, RIP3K, and/or IL6 Signaling in a Subject

In one aspect, disclosed are methods of modifying signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a disclosed compound, thereby modifying one or more of BRD4, RIP3K, and IL6 signaling in the subject.

Thus, in one aspect, disclosed are methods of modifying signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure represented by a formula:

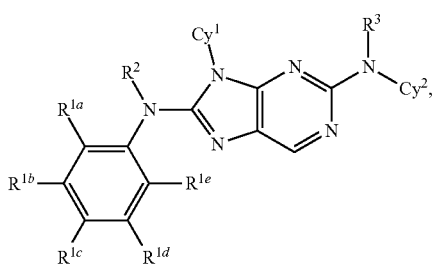

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

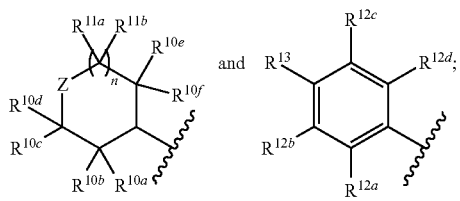

wherein n, when present, is 0 or 1; wherein Z, when present, is selected from —O—, —S—, and —NR$^{20}$—; wherein $R^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

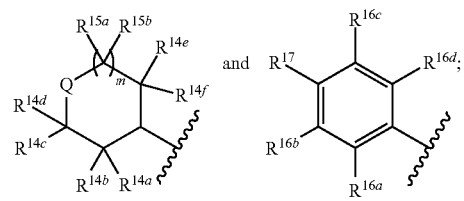

wherein m, when present, is 0 or 1; wherein Q, when present, is selected from —O—, —S—, and —NR$^{21}$—; wherein $R^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), or a pharmaceutically acceptable salt thereof, thereby modifying signaling of one or more of BRD4, RIP3K, and IL6.

Also disclosed are methods of modifying signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure represented by a formula:

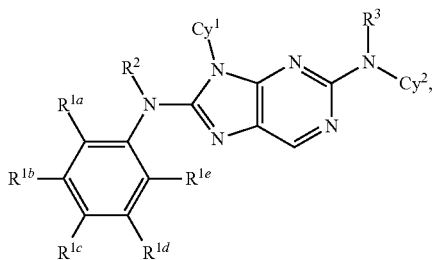

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein Cy$^1$ is a structure having a formula selected from:

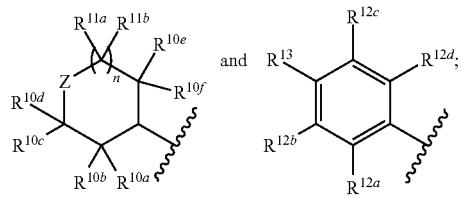

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12a}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

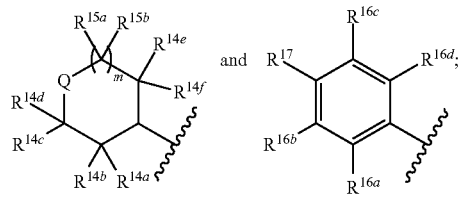

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), provided that when Cy$^1$ is

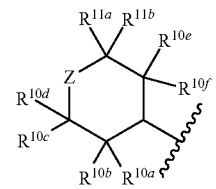

and at least seven of $R^{10a}$, $R^{10b}$, $R^{10c}$, $R^{10d}$, $R^{10e}$, $R^{10f}$, $R^{11a}$, and $R^{11b}$ are hydrogen, and when Cy$^2$ is

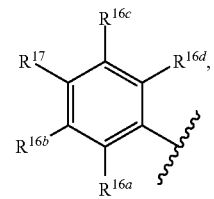

then either: (a) each of $R^{1a}$, $R^{1c}$, and $R^{1e}$ is halogen; or (b) Z is —O—, each of $R^{16a}$, $R^{16b}$, $R^{16c}$, and $R^{16d}$ is hydrogen, and R$^{17}$ is —OH, —NH$_2$, C1-C4 alkoxy, C1-C4 alkylamino, or (C1-C4)(C1-C4) dialkylamino, provided that when Cy$^1$ is

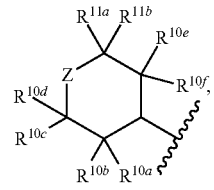

then Cy² is

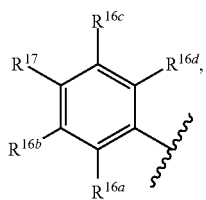

provided that when Cy¹ is

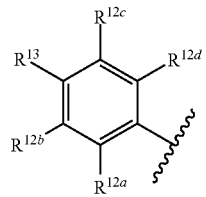

and Cy² is

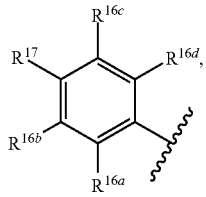

then $R^{17}$ is a non-hydrogen group, and provided that when Cy¹ is

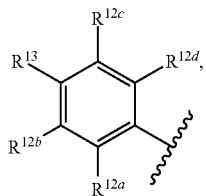

Cy² is

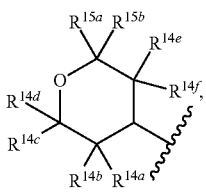

and at least seven of $R^{14a}$, $R^{14b}$, $R^{14c}$, $R^{14d}$, $R^{14e}$, $R^{14f}$, $R^{15a}$, and $R^{15b}$ are hydrogen, then each of $R^{12a}$, $R^{12b}$, $R^{12c}$ and $R^{12d}$ is hydrogen, or a pharmaceutically acceptable salt thereof, thereby modifying signaling of one or more of BRD4, RIP3K, and IL6.

Also disclosed are methods of modifying signaling of one or more of bromodomain-containing protein 4 (BRD4), receptor-interacting serine/threonine-protein kinase 3 (RIP3K), and interleukin 6 (IL6) in a subject in need thereof, the method comprising administering to the subject an effective amount of a compound having a structure selected from:

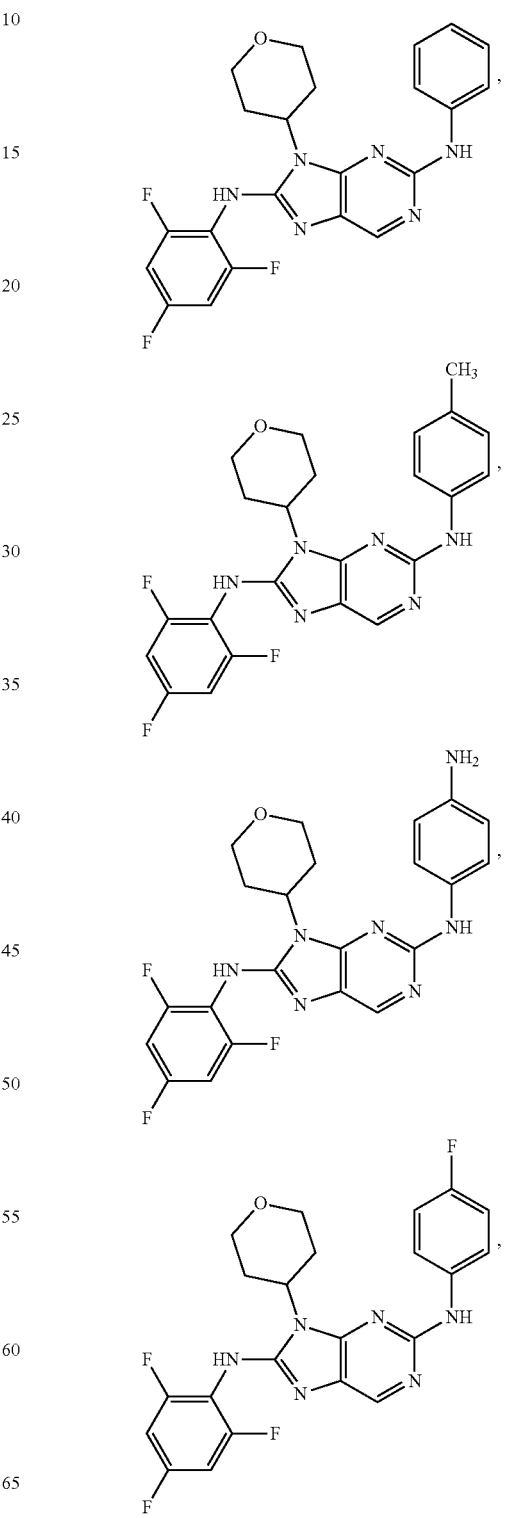

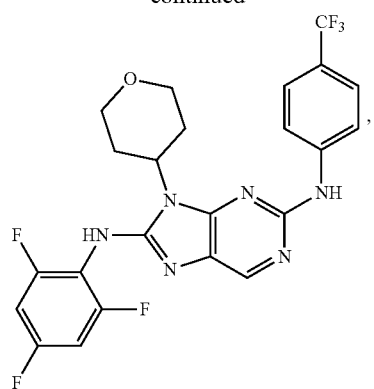
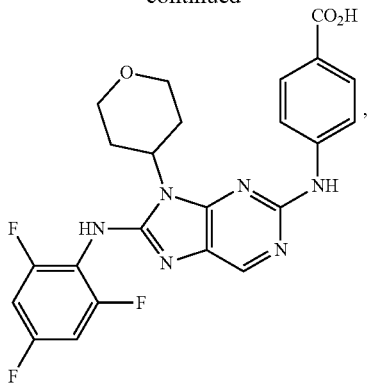

125

-continued

126

-continued

127
-continued
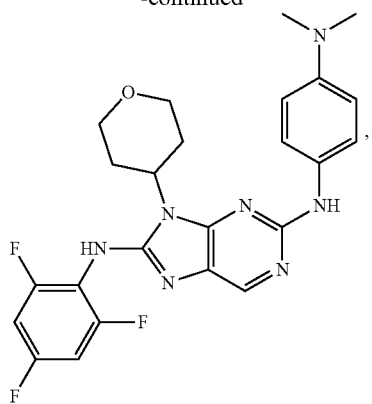
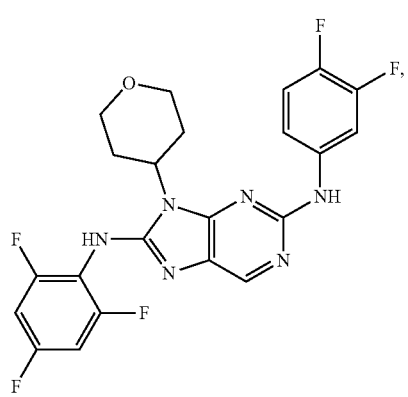
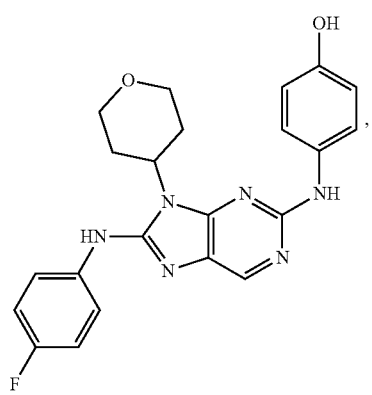
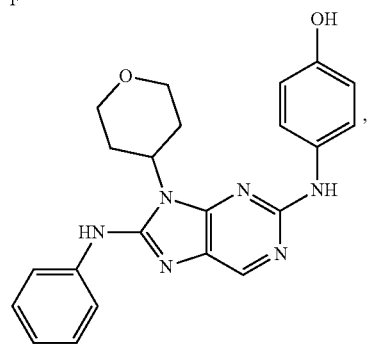
128
-continued
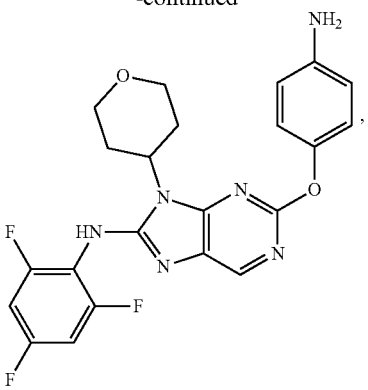
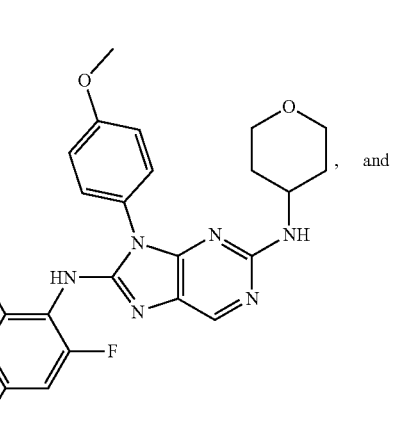
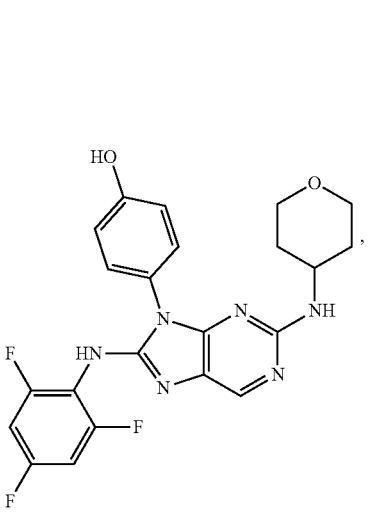
or a pharmaceutically acceptable salt thereof, thereby modifying signaling of one or more of BRD4, RIP3K, and IL6.

In various aspects, the compound has a structure represented by a formula:

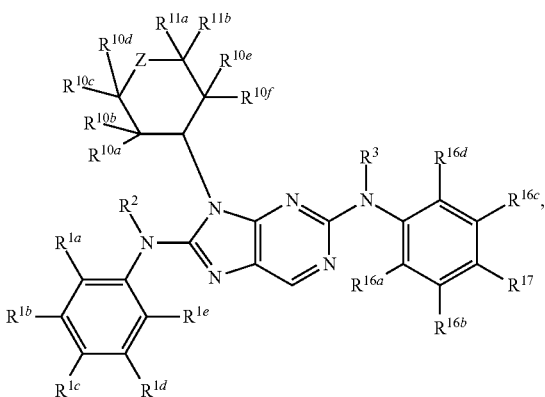

wherein each of $R^{1a}$, $R^{1c}$, and $R^{1e}$ is halogen.

In various aspects, the compound has a structure represented by a formula:

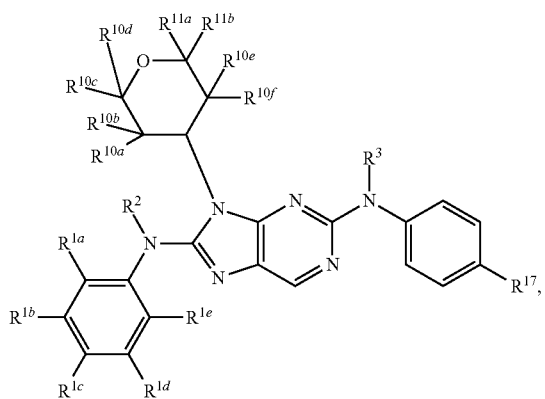

wherein $R^{17}$ is selected from —OH, —NH$_2$, C1-C4 alkoxy, C1-C4 alkylamino, and (C1-C4)(C1-C4) dialkylamino.

In various aspects, the compound has a structure represented by a formula:

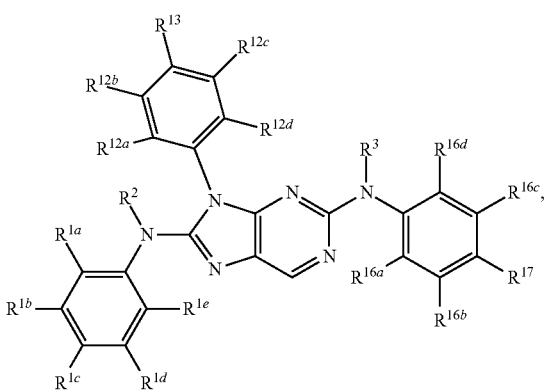

wherein $R^{17}$, when present, is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl).

In various aspects, the compound has a structure represented by a formula:

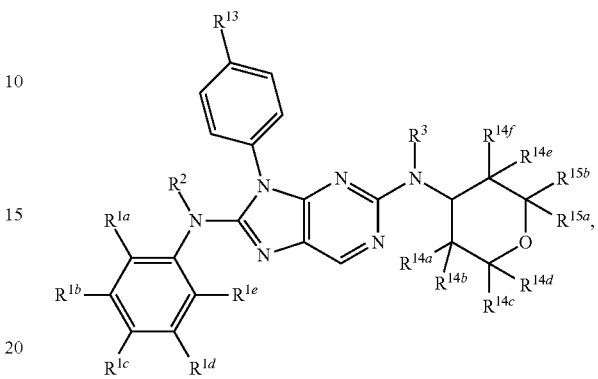

wherein one of $R^{14a}$, $R^{14b}$, $R^{14c}$, $R^{14d}$, $R^{14e}$, $R^{14f}$, $R^{15a}$, and $R^{15b}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein the remaining $R^{14a}$, $R^{14b}$, $R^{14c}$, $R^{14d}$, $R^{14e}$, $R^{14f}$, $R^{15a}$, and $R^{15b}$ groups are hydrogen.

In a further aspect, modifying is decreasing. In a still further aspect, modifying is inhibiting.

In a further aspect, BRD4 signaling is modified. In a still further aspect, RIP3K signaling is modified. In yet a further aspect, IL6 signaling is modified. In an even further aspect, each of BRD4, RIP3K, and IL6 signaling is modified.

In a further aspect, the subject has been diagnosed with a condition associated with signaling of one or more of BRD4, RIP3K, and IL6.

In a further aspect, the subject has been diagnosed with a condition associated with signaling of one or more of BRD4, RIP3K, and IL6 prior to the administering step. In still a further aspect, the subject has been diagnosed with a need for modifying signaling of one or more of BRD4, RIP3K, and IL6 prior to the administering step. In yet a further aspect, the subject has been diagnosed with a need for treatment of a condition associated with BRD4, RIP3K, and/or IL6 signaling dysfunction prior to the administering step.

In a further aspect, the method further comprises the step of identifying a subject in need of treatment of a condition associated with BRD4, RIP3K, and/or IL6 signaling dysfunction.

In a further aspect, the condition associated with BRD4, RIP3K, and/or IL6 signaling dysfunction is due to exposure to an arsenical. Examples of arsenicals include, but are not limited to, arsanilic acid, arsenic, arsenic (V) pentoxide, arsenic (III) sulfide, arsenic (III) trichloride, arsenobetaine, arsine, calcium arsenate, dimethylarsinic acid, lead arsenate, methanearsonic acid, potassium arsenate, potassium arsenite, sodium arsenate, sodium arsenite, sodium cacodylate, arsenic trioxide, methylarsonic acid, dimethylarsinic acid, lewisite, diphenylchlorarsine, diphenylcyanoarsine, diethylchloroarsine, phenylarsine oxide, and arsenobetaine.

In various aspects, exposure is via ingestion, inhalation, and/or absorption through a mucosal membrane (e.g., eyes, lips). In various further aspects, exposure is dermal exposure.

In a further aspect, the condition associated with BRD4, RIP3K, and/or IL6 signaling dysfunction is inflammation, skin lesions, dysfunction of systemic organs, and/or skin blisters.

In a further aspect, the condition associated with BRD4, RIP3K, and/or IL6 signaling dysfunction is arsenicosis or arsenic poisoning.

In a further aspect, the condition associated with BRD4, RIP3K, and/or IL6 signaling dysfunction is cancer. Examples of cancers include, but are not limited to, lung cancer, skin cancer, bladder cancer, kidney cancer, or liver cancer. In a still further aspect, the cancer is induced by arsenicals and/or other environmental agents.

In a further aspect, the condition associated with BRD4, RIP3K, and/or IL6 signaling dysfunction is acute lung injury (ALI), acute kidney injury (AKI), chronic kidney disease (CKD), liver damage, neurological alterations, immune dysregulation, or ocular damages including blindness.

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a condition associated with BRD4, RIP3K, and/or IL6 signaling dysfunction. In a still further aspect, the agent is a chelating agent, a retinoid, vitamin E, vitamin E, selenium, N-acetylcysteine, or 4-phenylbutyric acid.

In a further aspect, the compound and the agent are administered sequentially. In a still further aspect, the compound and the agent are administered simultaneously.

In a further aspect, the compound and the agent are co-formulated. In a still further aspect, the compound and the agent are co-packaged.

In a further aspect, the compound is administered as a single active agent.

G. Modifying BRD4, RIP3K, and/or IL6 Signaling in at Least One Cell

In one aspect, disclosed are methods of modifying signaling of one or more of bromodomain-containing protein 4 (BRD4), receptor-interacting serine/threonine-protein kinase 3 (RIP3K), and interleukin 6 (IL6) in a cell, the method comprising contacting the cell with an effective amount of a disclosed compound, thereby modifying one or more of BRD4, RIP3K, and IL6 signaling in the cell.

Thus, in one aspect, disclosed are methods of modifying signaling of one or more of bromodomain-containing protein 4 (BRD4), receptor-interacting serine/threonine-protein kinase 3 (RIP3K), and interleukin 6 (IL6) in a cell, the method comprising administering to the subject an effective amount of a compound having a structure represented by a formula:

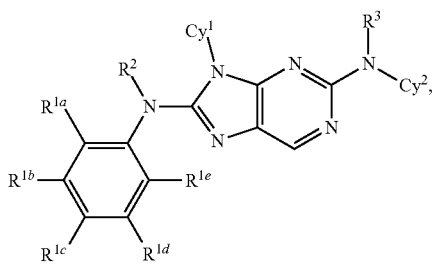

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein $Cy^1$ is a structure having a formula selected from:

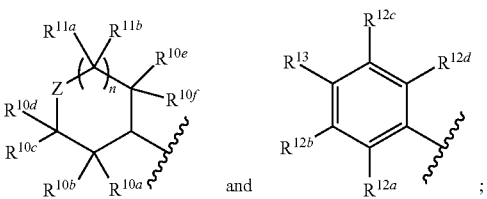

wherein n, when present, is 0 or 1; wherein Z, when present, is selected from —O—, —S—, and —NR$^{20}$—; wherein $R^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein $Cy^2$ is a structure having a formula selected from:

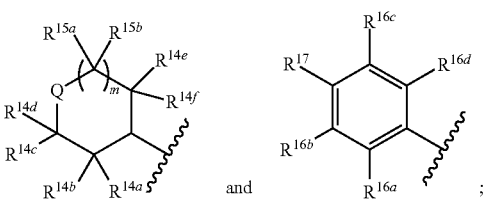

wherein m, when present, is 0 or 1; wherein Q, when present, is selected from —O—, —S—, and —NR$^{21}$—; wherein $R^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), or a pharmaceutically acceptable salt thereof, thereby modifying signaling of one or more of BRD4, RIP3K, and IL6 in the cell.

Also disclosed are methods of modifying signaling of one or more of bromodomain-containing protein 4 (BRD4), receptor-interacting serine/threonine-protein kinase 3 (RIP3K), and interleukin 6 (IL6) in a cell, the method comprising contacting the cell with an effective amount of a compound having a structure represented by a formula:

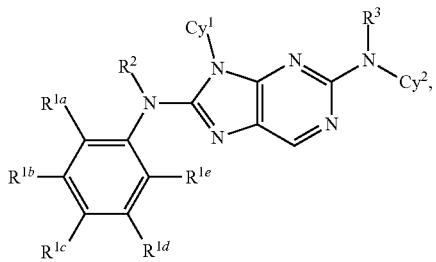

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein $Cy^1$ is a structure having a formula selected from:

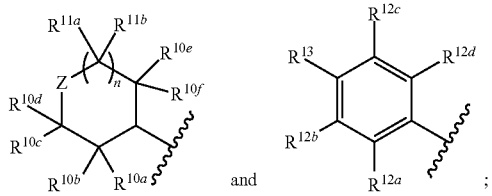

wherein n, when present, is 0 or 1; wherein Z, when present, is selected from —O—, —S—, and —NR$^{20}$—; wherein $R^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein $Cy^2$ is a structure having a formula selected from:

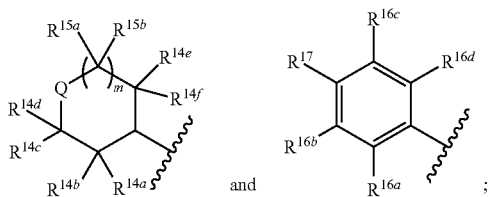

wherein m, when present, is 0 or 1; wherein Q, when present, is selected from —O—, —S—, and —NR$^{21}$—; wherein $R^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), provided that when $Cy^1$ is

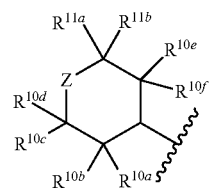

and at least seven of $R^{10a}$, $R^{10b}$, $R^{10c}$, $R^{10d}$, $R^{10e}$, $R^{10f}$, $R^{11a}$, and $R^{11b}$ are hydrogen, and when $Cy^2$ is

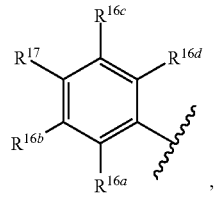

then either: (a) each of $R^{1a}$, $R^{1c}$, and $R^{1e}$ is halogen; or (b) Z is —O—, each of $R^{16a}$, $R^{16b}$, $R^{16c}$, and $R^{16d}$ is hydrogen, and $R^{17}$ is —OH, —NH$_2$, C1-C4 alkoxy, C1-C4 alkylamino, or (C1-C4)(C1-C4) dialkylamino, provided that when $Cy^1$ is

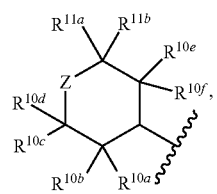

then $Cy^2$ is

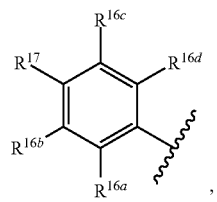

provided that when $Cy^1$ is

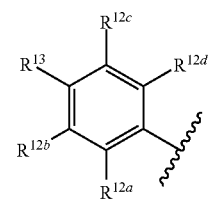

and $Cy^2$ is

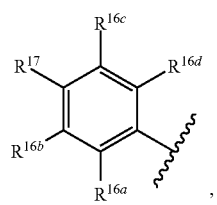

then $R^{17}$ is a non-hydrogen group, and provided that when $Cy^1$ is

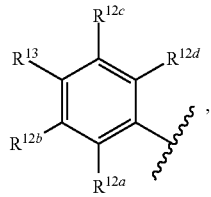

$Cy^2$ is

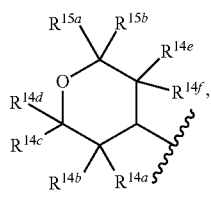

and at least seven of $R^{14a}$, $R^{14b}$, $R^{14c}$, $R^{14d}$, $R^{14e}$, $R^{14f}$, $R^{15a}$, and $R^{15b}$ are hydrogen, then each of $R^{12a}$, $R^{12b}$, $R^{12c}$ and $R^{12d}$ is hydrogen, or a pharmaceutically acceptable salt thereof, thereby modifying signaling of one or more of BRD4, RIP3K, and IL6 in the cell.

Also disclosed are methods of modifying signaling of one or more of bromodomain-containing protein 4 (BRD4), receptor-interacting serine/threonine-protein kinase 3 (RIP3K), and interleukin 6 (IL6) in a cell, the method comprising administering to the subject an effective amount of a compound having a structure selected from:

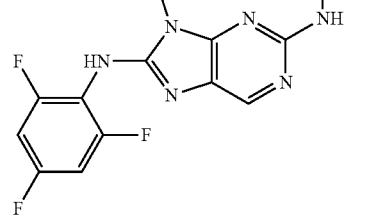

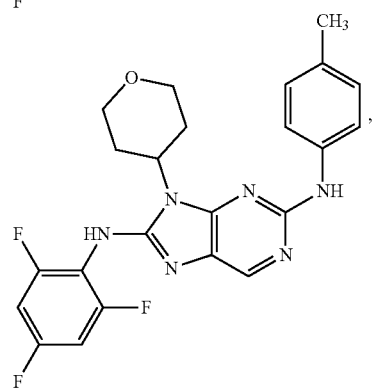

137
-continued
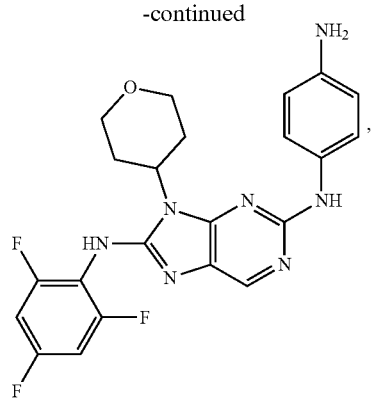
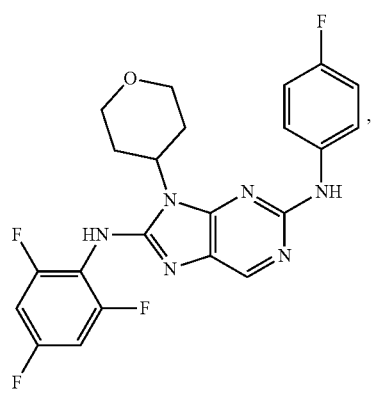
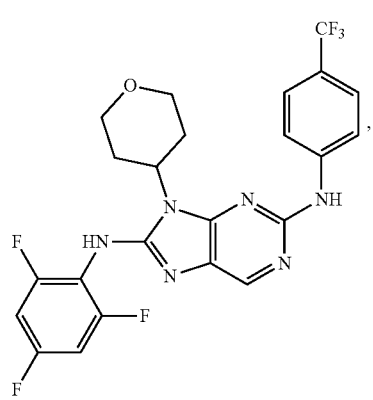
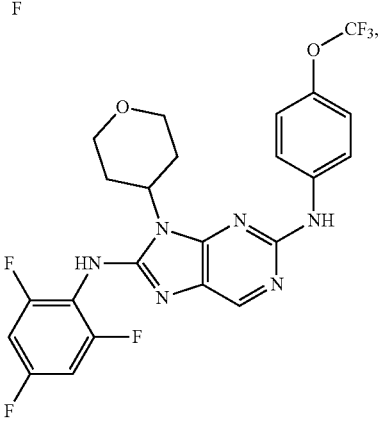
138
-continued
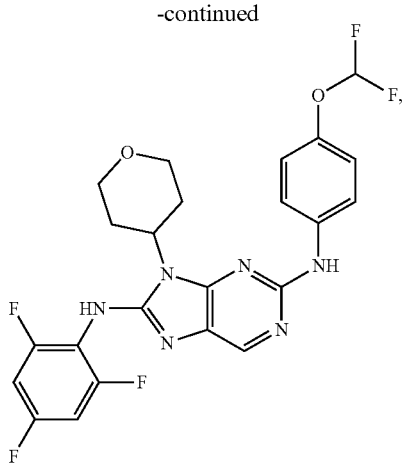
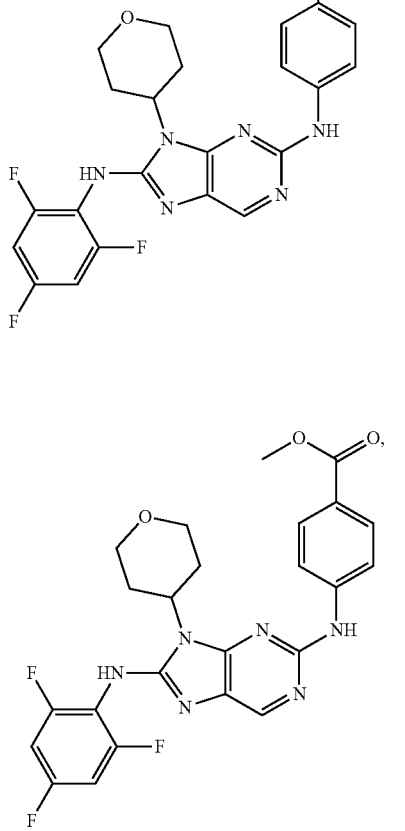
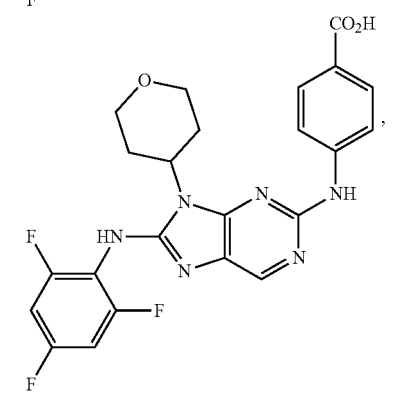
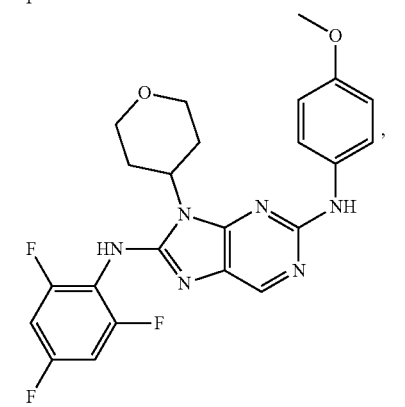

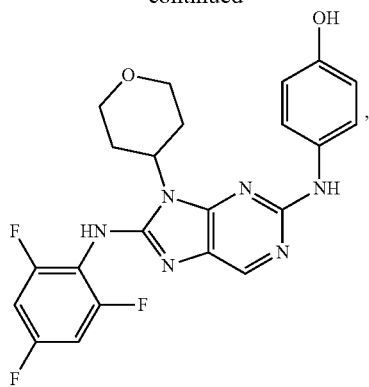
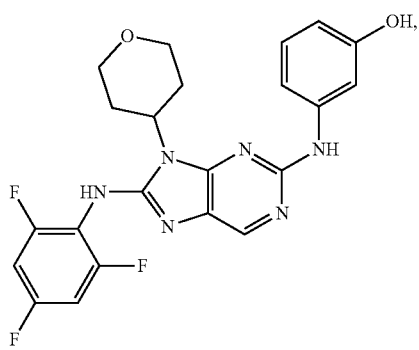
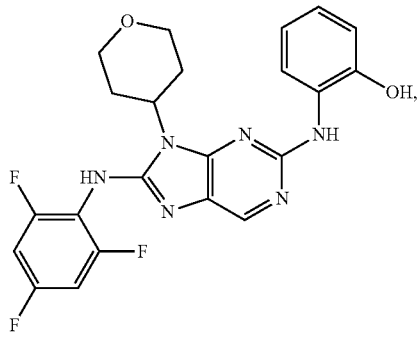
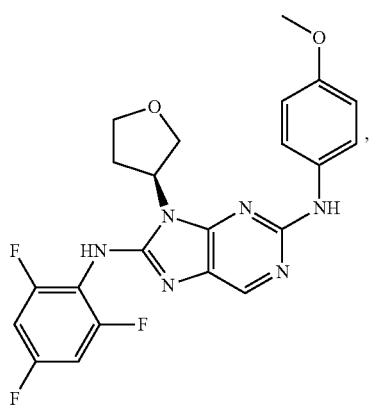
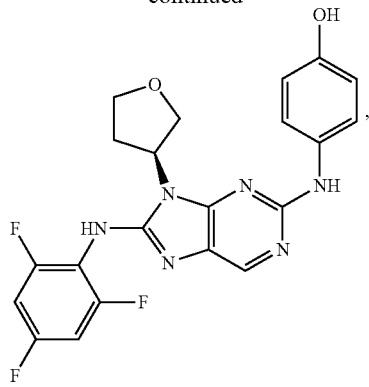
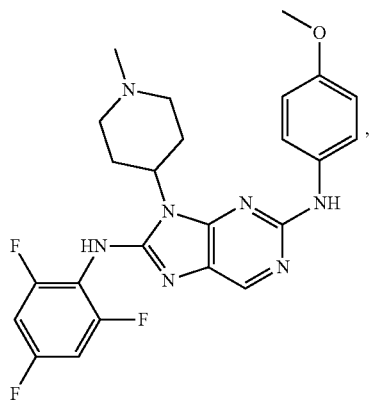
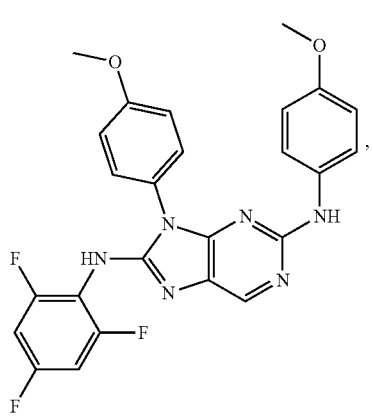
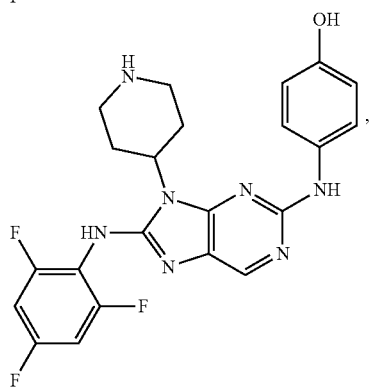

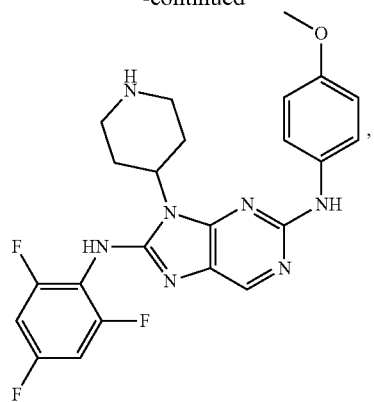
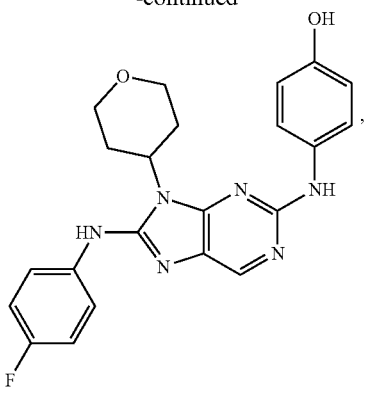
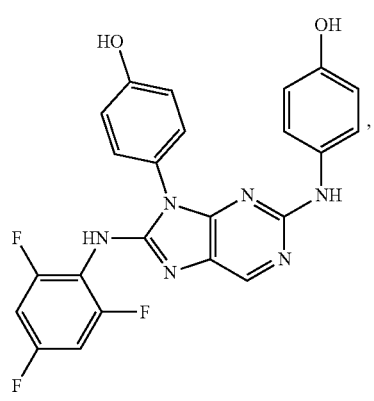
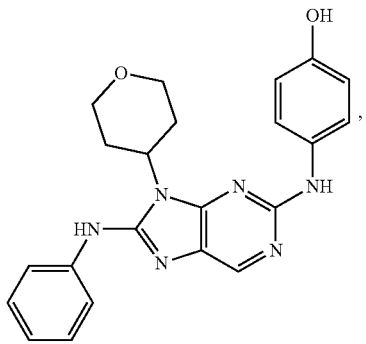
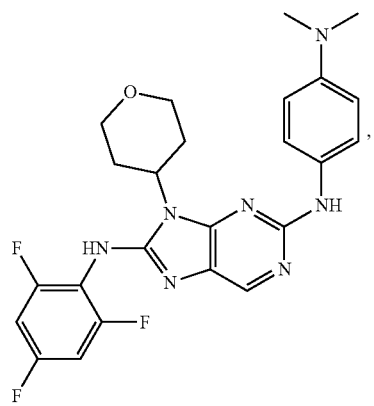
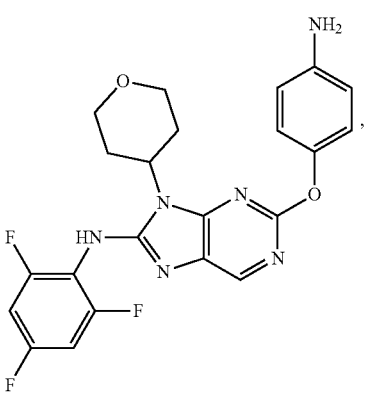
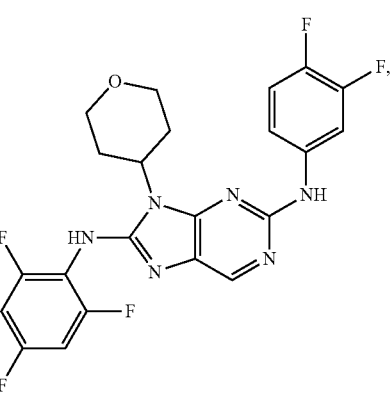
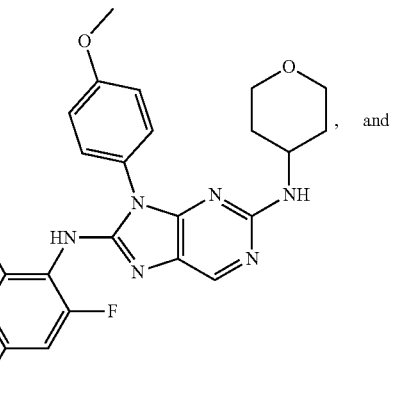

-continued

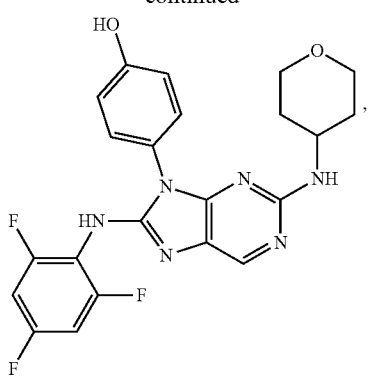

or a pharmaceutically acceptable salt thereof, thereby modifying signaling of one or more of BRD4, RIP3K, and IL6 in the cell.

In various aspects, the compound has a structure represented by a formula:

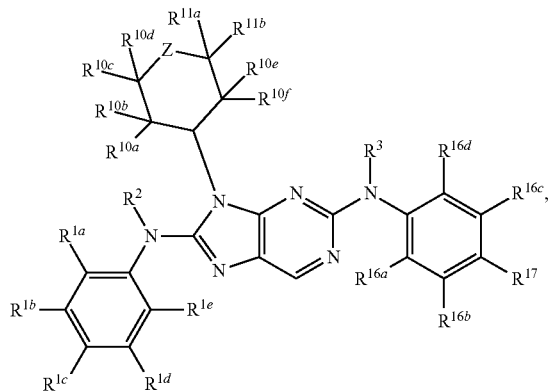

wherein each of $R^{1a}$, $R^{1c}$, and $R^{1e}$ is halogen.

In various aspects, the compound has a structure represented by a formula:

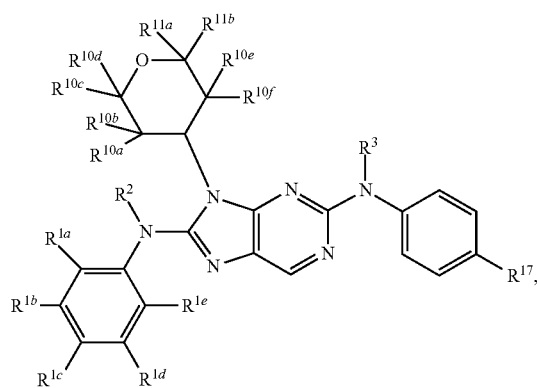

wherein $R^{17}$ is selected from —OH, —NH$_2$, C1-C4 alkyl, C1-C4 alkylamino, and (C1-C4)(C1-C4) dialkylamino.

In various aspects, the compound has a structure represented by a formula:

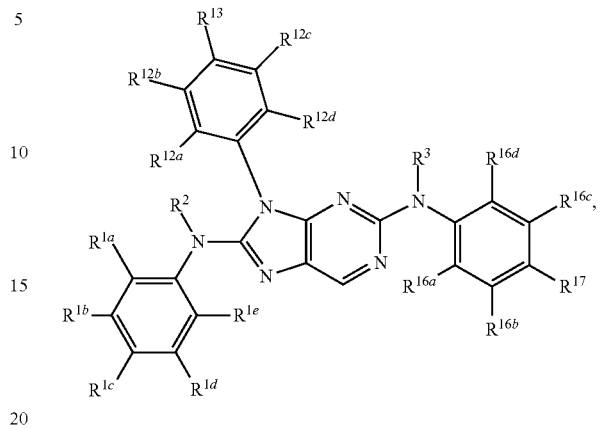

wherein $R^{17}$, when present, is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl).

In various aspects, the compound has a structure represented by a formula:

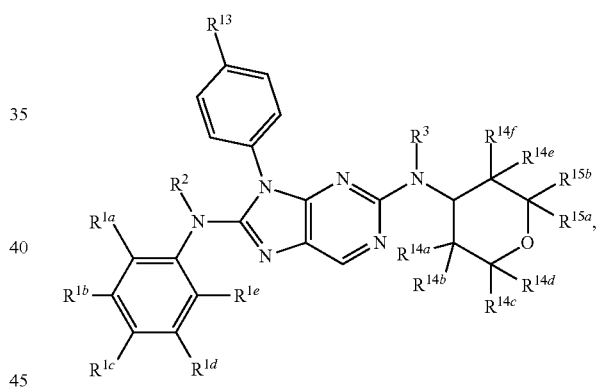

wherein one of $R^{14a}$, $R^{14b}$, $R^{14c}$, $R^{14d}$, $R^{14e}$, $R^{14f}$, $R^{15a}$, and $R^{15b}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein the remaining $R^{14a}$, $R^{14b}$, $R^{14c}$, $R^{14d}$, $R^{14e}$, $R^{14f}$, $R^{15a}$, and $R^{15b}$ groups are hydrogen.

In a further aspect, modifying is decreasing. In a still further aspect, modifying is inhibiting.

In a further aspect, the cell is mammalian. In a still further aspect, the cell is human.

In a further aspect, the cell has been isolated from a human prior to the administering step.

In a further aspect, contacting is via administration to a subject. In a still further aspect, the subject has been diagnosed with a need for modification of one or more of BRD4, RIP3K, and/or IL6 signaling prior to the administering step.

In yet a further aspect, the subject has been diagnosed with a need for treatment of a condition associated with BRD4, RIP3K, and/or IL6 signaling dysfunction.

In a further aspect, the condition associated with BRD4, RIP3K, and/or IL6 signaling dysfunction is due to exposure to an arsenical. Examples of arsenicals include, but are not limited to, arsanilic acid, arsenic, arsenic (V) pentoxide, arsenic (III) sulfide, arsenic (III) trichloride, arsenobetaine, arsine, calcium arsenate, dimethylarsinic acid, lead arsenate, methanearsonic acid, potassium arsenate, potassium arsenite, sodium arsenate, sodium arsenite, sodium cacodylate, arsenic trioxide, methylarsonic acid, dimethylarsinic acid, lewisite, diphenylchlorarsine, diphenylcyanoarsine, diethylchloroarsine, phenylarsine oxide, and arsenobetaine.

In various aspects, exposure is via ingestion, inhalation, and/or absorption through a mucosal membrane (e.g., eyes, lips). In various further aspects, exposure is dermal exposure.

In a further aspect, the condition associated with BRD4, RIP3K, and/or IL6 signaling dysfunction is inflammation, skin lesions, dysfunction of systemic organs, and/or skin blisters.

In a further aspect, the condition associated with BRD4, RIP3K, and/or IL6 signaling dysfunction is arsenicosis or arsenic poisoning.

In a further aspect, the condition associated with BRD4, RIP3K, and/or IL6 signaling dysfunction is cancer. Examples of cancers include, but are not limited to, lung cancer, skin cancer, bladder cancer, kidney cancer, or liver cancer. In a still further aspect, the cancer is induced by arsenicals and/or other environmental agents.

In a further aspect, the condition associated with BRD4, RIP3K, and/or IL6 signaling dysfunction is acute lung injury (ALI), acute kidney injury (AKI), chronic kidney disease (CKD), liver damage, neurological alterations, immune dysregulation, or ocular damages including blindness.

H. Additional Methods of Using the Compounds

The compounds and pharmaceutical compositions of the invention are useful in treating or controlling conditions associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, and skin blisters.

Examples of conditions associated with BRD4, RIP3K, and/or IL6 signaling dysfunction for which the compounds and compositions can be useful in treating, include, but are not limited to, kidney diseases such as, for example, cancer (e.g., lung cancer, skin cancer, bladder cancer, kidney cancer, liver cancer), arsenicosis, arsenic poisoning, inflammation, skin lesions, and skin blisters.

To treat or control the condition, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a condition associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a condition associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days. 1. USE OF COMPOUNDS In one aspect, the invention relates to the use of a disclosed compound or a product of a disclosed method. In a further aspect, a use relates to the manufacture of a medicament for the treatment of a condition associated with BRD4, RIP3K, and/or IL6 signaling dysfunction such as, for example, cancer (e.g., lung cancer, skin cancer, bladder cancer, kidney cancer, liver cancer), arsenicosis, arsenic poisoning, inflammation, skin lesions, dysfunction of systemic organs, and skin blisters.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a condition associated with BRD4, RIP3K, and/or IL6 signaling dysfunction in a subject. In one aspect, the use is characterized in that the subject is a human. In one aspect, the use is characterized in that the condition associated with BRD4, RIP3K, and/or IL6 signaling dysfunction is a kidney disease.

In a further aspect, the use relates to the manufacture of a medicament for the treatment of a condition associated with BRD4, RIP3K, and/or IL6 signaling dysfunction in a subject.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a condition associated with BRD4, RIP3K, and/or IL6 signaling dysfunction in a mammal. In a further aspect, the condition associated with BRD4, RIP3K, and/or IL6 signaling dysfunction is a cancer (e.g., lung cancer, skin cancer, bladder cancer, kidney cancer, liver cancer), arsenicosis, arsenic poisoning, inflammation, skin lesions, dysfunction of systemic organs, and skin blisters.

2. Manufacture of a Medicament

In one aspect, the invention relates to a method for the manufacture of a medicament for treating a condition associated with BRD4, RIP3K, and/or IL6 signaling dysfunction in a subject having the condition, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the treatment of a condition associated with BRD4, RIP3K, and/or IL6 signaling dysfunction (e.g., cancer such as, for example, lung cancer, skin cancer, bladder cancer, kidney cancer, and liver cancer, arsenicosis, arsenic poisoning, inflammation, skin lesions, dysfunction of systemic organs, and skin blisters). The dose administered to an animal, particularly a human, in the context of the present invention should be sufficient to affect a therapeutic response in the animal over a reasonable timeframe. One skilled in the art will recognize that dosage will depend upon a variety of factors including the condition of the animal and the body weight of the animal.

The total amount of the compound of the present disclosure administered in a typical treatment is preferably between about 0.05 mg/kg and about 100 mg/kg of body weight for mice, and more preferably between 0.05 mg/kg and about 50 mg/kg of body weight for mice, and between about 100 mg/kg and about 500 mg/kg of body weight for humans, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

3. Kits

In one aspect, disclosed are kits comprising a disclosed compound, and one or more of: (a) an agent associated with the treatment of a condition associated with BRD4, RIP3K, and/or IL6 signaling dysfunction; (b) instructions for administering the compound in connection with treating a condition associated with BRD4, RIP3K, and/or IL6 signaling dysfunction; and (c) instructions for treating a condition associated with BRD4, RIP3K, and/or IL6 signaling dysfunction.

Thus, in one aspect, disclosed are kits comprising a compound having a structure represented by a formula:

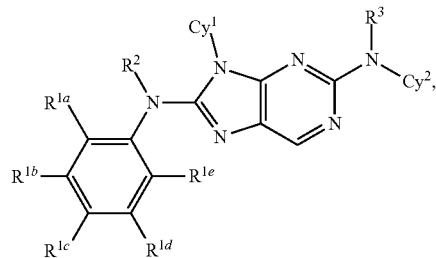

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^2$ and $R^3$ is independently selected from hydrogen and C1-C4 alkyl; wherein $Cy^1$ is a structure having a formula selected from:

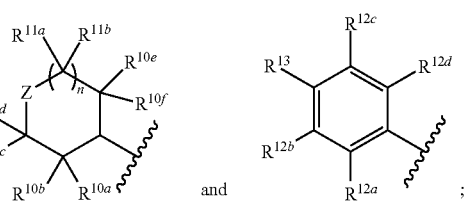

wherein n, when present, is 0 or 1; wherein Z, when present, is selected from —O—, —S—, and —NR$^{20}$—; wherein R$^{20}$, when present, is selected from hydrogen and C1-C4 alkyl; wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{11a}$ and $R^{11b}$ when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

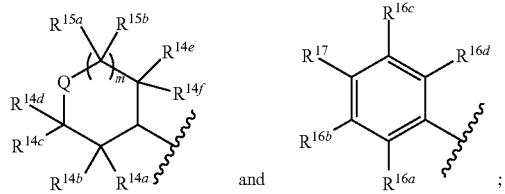

and ;

wherein m, when present, is 0 or 1; wherein Q, when present, is selected from —O—, —S—, and —NR$^{21}$—; wherein R$^{21}$, when present, is selected from hydrogen and C1-C4 alkyl; wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$(C1-C4 alkyl), or a pharmaceutically acceptable salt thereof, and one or more of: (a) an agent associated with the treatment of a condition associated with BRD4, RIP3K, and/or IL6 signaling dysfunction; (b) instructions for administering the compound in connection with treating a condition associated with BRD4, RIP3K, and/or IL6 signaling dysfunction; and (c) instructions for treating a condition associated with BRD4, RIP3K, and/or IL6 signaling dysfunction.

In a further aspect, the condition associated with BRD4, RIP3K, and/or IL6 signaling dysfunction is cancer. In a still further aspect, the cancer is lung cancer, skin cancer, bladder cancer, kidney cancer, or liver cancer. In yet a further aspect, the condition associated with BRD4, RIP3K, and/or IL6 signaling dysfunction is inflammation, skin lesions, dysfunction of systemic organs, or skin blisters. In an even further aspect, the condition associated with BRD4, RIP3K, and/or IL6 signaling dysfunction is arsenicosis or arsenic poisoning. In a still further aspect, the condition associated with BRD4, RIP3K, and/or IL6 signaling dysfunction is acute lung injury (ALI), acute kidney injury (AKI), chronic kidney disease (CKD), liver damage, neurological alterations, immune dysregulation, or ocular damages including blindness.

In a further aspect, the agent is a chelating agent, a retinoid, vitamin E, selenium, N-acetylcysteine, or 4-phenylbutyric acid. Examples of chelating agents include, but are not limited to, meso-2,3-dimercaptosuccinic acid (DMSA), sodium 2,3-dimercapto-1-propane sulfonic acid (DMPS), or d-penicillamin. Examples of retinoids include, but are not limited to, retinol, etretinate, and UAB30.

In a further aspect, the compound and the agent are co-formulated. In a further aspect, the compound and the agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

I. Examples

As the tissue damage and subsequent robust inflammation associated with arsenical exposure are driven by complex multiple pathways, herein a novel approach is described that will address the effective modulation of several critical pathways and associated organ damage simultaneously. Preliminary data indicate that epigenetic pathways that are BRD4-dependent are up-regulated in multiple organs following cutaneous exposure to arsenicals. In addition, UPR signaling is elevated under these conditions, which has been shown to be associated with inflammatory responses. If the stress becomes too severe, the UPR switches from being a pro-survival response to a pro-death one, and the molecular mechanisms underlying the endoplasmic reticulum (ER)

stress-mediated death have remained incompletely understood. Pretreatment with compounds such as 4-phenylbutyric acid (PBA) has been shown to attenuate the induced activation of UPR signaling and also the arsenic-mediated increase in reactive oxygen species (ROS) and afford protection against disruption of macrophage functions. These data demonstrate that UPR signaling and ROS generation are interdependent and are involved in the arsenic-induced pathobiology of the macrophage.

In addition, preliminary data have shown that necrosis-regulating RIP Kinase 3 and the antioxidant HO-1 could be additional potential targets. RIP Kinase 3, downstream of various receptors, is at the "crossroad between life and death" and has been reported to be a regulator of ER stress-induced death. RIP Kinase 3-deficiency in mouse embryonic fibroblasts (MEFS) has been shown to be protective against apoptosis induced by ER stressors, which is reflected by reduced caspase activation and poly ADP ribose polymerase (PARP) processing. Therefore, the major focus of these studies is on targeting pathways and finding novel modulatory compounds as potential antidotes of arsenicals and related chemical vesicants.

Without wishing to be bound by theory, the disclosed compounds alleviate cutaneous injury, pulmonary, and renal toxicity as countermeasures for mitigating the effects of exposure to chemical vesicants. The initial approach includes establishing in vitro assays for BRD4, RIP3K, and IL6. Next, a library of FDA approved and unapproved drug library (4,074 compounds) were evaluated in the BRD4 and RIP3 kinase assays. The goal was to find dual acting compounds with BRD4 and RIP3K activity. From the screen, several compounds were found with the desired dual activity. In addition, several novel inhibiters of BRD4 and RIP3K were identified. An IL-6 cell based was developed, and the compounds with activity agains BRD4, RIP3K and duel activity were evaluated in this assay as well, as further described herein, in order to identify dual inhibitors of BRD4 and RIP3K that also inhibit IL-6a.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals

All reactions were carried out in an oven-dried glassware under argon atmosphere using standard gas-tight syringe, cannula, and septa. The reaction temperatures were measured externally. Stirring was achieved with oven dried magnetic bars. All the reactions were done in anhydrous solvents ($CH_2Cl_2$, THF, MeOH) purchased from Sigma-Aldrich. All commercially purchased reagents were used without purification. The reactions were monitored by thin-layer chromatography (TLC) on a pre-coated silica gel (60 F254) glass plates from EMD Millipore and visualized using UV light (254 nm). Purification of the compounds was performed on Teledyne-ISCO Combiflash Rf 200 purification system using Redisep Rf® normal phase silica gel columns 230-400 mesh. ESI-MS spectra were recorded on a BioTof-2 time-of-flight mass spectrometer. Proton NMR spectra were recorded on a Varian Unity 400 NMR spectrometer operating at 400 MHz calibrated to the solvent peak and TMS peak. The chemical formula and Exact Mass for target compounds were determined from the $(M+H)^+$ by high resolution mass spectroscopy using an Agilent 6210 Electrospray Time of Flight.

a. Synthesis of Representative Example Compound No. 1

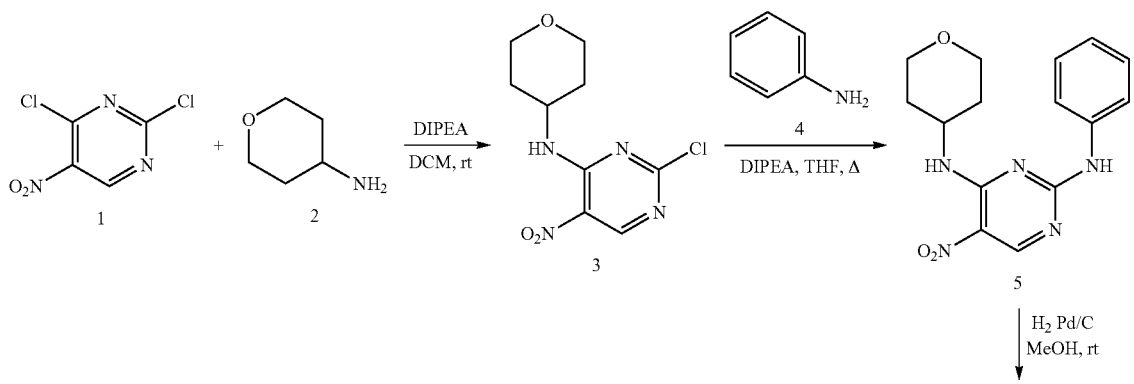

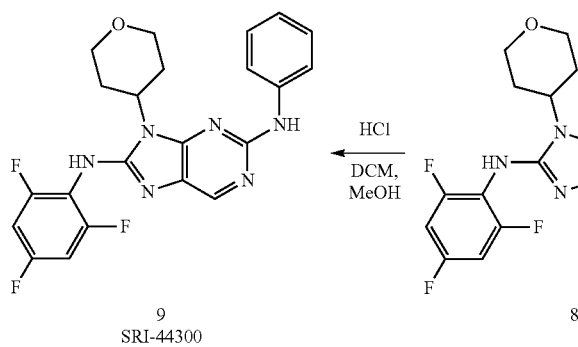 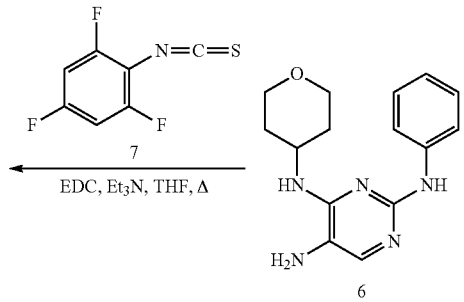

9
SRI-44300 i. 2-chloro-5-nitro-N-tetrahydropyran-4-yl-pyrimidin-4-amine (3)

A solution of 2,4-dichloro-5-nitro-pyrimidine, 1 (1.0 g, 5.16 mmol) in dry DCM (10 mL) was cooled down to −20° C. in a salt-ice bath. N,N-Diisopropylethylamine (0.99 mL, 5.67 mmol) was added, followed by tetrahydro-pyran-4-ylamine, 2 (521 mg, 5.16 mmol). The resulting mixture was stirred for 2 hours until room temperature. The solvent was removed under vacuum and the resulting material was purified on Teledyne ISCO Combiflash® Rf purification system (0-25% EtOAc in hexanes). The desired fractions were collected and evaporated to give a yellow solid that was triturated with hexanes/$CH_2Cl_2$, and dried to afford 2-chloro-5-nitro-N-tetrahydropyran-4-yl-pyrimidin-4-amine, 3 (0.80 g, 60%) as a yellow solid.

ESI-MS m/z: 259 $(M+H)^+$; $^1$H NMR (400 MHz, Chloroform-d) δ 9.06 (s, 1H), 8.32 (d, J=7.7 Hz, 1H), 4.51-4.38 (m, 1H), 4.08-3.99 (m, 2H), 3.59 (ddd, J=11.9, 11.2, 2.3 Hz, 2H), 2.11-2.00 (m, 2H), 1.74-1.61 (m, 2H).

ii. 5-nitro-N2-phenyl-N4-tetrahydropyran-4-yl-pyrimidine-2,4-diamine (5)

A solution of 2-chloro-5-nitro-N-tetrahydropyran-4-yl-pyrimidin-4-amine, 3 (600 mg, 2.32 mmol) in dry THF (10 mL) was treated with N,N-Diisopropylethylamine (0.45 mL, 2.55 mmol), followed by aniline, 4 (216 mg, 2.32 mmol). The resulting mixture was stirred under reflux overnight. The solvent was removed under vacuum and the resulting material was purified on Teledyne ISCO Combiflash® Rf purification system (0-100% EtOAc in hexanes). The desired fractions were collected and evaporated to give a yellow solid that was triturated with hexanes/$CH_2Cl_2$, and dried to afford 5-nitro-N2-phenyl-N4-tetrahydropyran-4-yl-pyrimidine-2,4-diamine, 5 (639 mg, 87%) as a yellow solid.

ESI-MS m/z: 316.1 $(M+H)^+$; $^1$H NMR (400 MHz, Chloroform-d) δ 9.06 (s, 1H), 8.45 (s, 1H), 7.67-7.57 (m, 2H), 7.41-7.33 (m, 2H), 7.17 (m, 1H), 4.34 (m, 1H), 4.05 (dt, J=11.9, 3.6 Hz, 2H), 3.56 (td, J=11.6, 2.3 Hz, 2H), 2.13-2.02 (m, 2H), 1.70 (m, 2H).

iii. N2-phenyl-N4-tetrahydropyran-4-yl-pyrimidine-2,4,5-triamine (6)

To a mixture of 5-nitro-N2-phenyl-N4-tetrahydropyran-4-yl-pyrimidine-2,4-diamine, 5 (400 mg, 1.27 mmol) in dry MeOH (15 mL) was added a catalytic amount of 10% Pd/C under argon. The mixture was stirred in a Parr hydrogenator at 35 psi overnight. The reaction mixture was filtered through Celite®, eluting with methanol and acetone. The filtrate was concentrated and dried under vacuum to give N2-phenyl-N4-tetrahydropyran-4-yl-pyrimidine-2,4,5-triamine, 6 (255 mg, 70%) as a black solid, which was used in the next step without further purification.

ESI-MS m/z: 286.2 $(M+H)^+$; $^1$H NMR (400 MHz, DMSO-$d_6$) δ 8.58 (s, 1H), 7.71-7.64 (m, 2H), 7.38 (s, 1H), 7.21-7.13 (m, 2H), 6.82-6.74 (m, 1H), 6.34 (d, J=7.2 Hz, 1H), 4.20-4.06 (m, 1H), 3.93 (ddd, J=11.8, 4.3, 2.2 Hz, 2H), 3.43 (td, J=11.7, 2.1 Hz, 2H), 1.99-1.91 (m, 2H), 1.60-1.44 (m, 2H).

iv. N2-phenyl-9-tetrahydropyran-4-yl-N8-(2,4,6-trifluorophenyl)purine-2,8-diamine (8)

A mixture of N2-phenyl-N4-tetrahydropyran-4-yl-pyrimidine-2,4,5-triamine, 6 (250 mg, 0.88 mmol), 1,3,5-trifluoro-2-isothiocyanato-benzene (165 mg, 0.88 mmol) EDC·HCl (202 mg, 1.05 mmol), and Et$_3$N (0.18 mL, 1.31 mmol) in dry THF (10 mL) was stirred under reflux overnight. The solvent was removed under vacuum and the resulting material was purified on Teledyne ISCO Combiflash® Rf purification system (0-50% EtOAc in hexanes). The desired fractions were collected and dried to afford N2-phenyl-9-tetrahydropyran-4-yl-N8-(2,4,6-trifluorophenyl)purine-2,8-diamine, 8 (230 mg, 60%) as a brown solid.

ESI-MS m/z: 441.2 $(M+H)^+$; $^1$H NMR (400 MHz, DMSO-$d_6$) δ 9.29 (s, 1H), 8.92 (br. s, 1H), 8.29 (br. s, 1H), 7.78 (d, J=8.1 Hz, 2H), 7.42-7.09 (m, 4H), 6.88 (tt, J=7.4, 1.2 Hz, 1H), 4.71 (m, 1H), 4.03 (m, 2H), 3.55-3.41 (m, 2H), 2.80 (m, 2H), 1.79 (m, 2H).

v. N2-phenyl-9-tetrahydropyran-4-yl-N8-(2,4,6-trifluorophenyl)purine-2,8-diamine; hydrochloride (9, SRI-44300)

A solution of N2-phenyl-9-tetrahydropyran-4-yl-N8-(2,4,6-trifluorophenyl)purine-2,8-diamine, 8 (101 mg, 0.23 mmol), in MeOH (0.5 mL) and $CH_2Cl_2$ (1.5 mL) was cooled down to 0° C. in an ice-water bath and treated with 2M HCl in Et$_2$O (0.57 mL, 1.15 mmol). The mixture was stirred at room temperature for 2 hours. The solid that had formed was filtered under argon, washed with Et$_2$O, and dried under vacuum to give N2-phenyl-9-tetrahydropyran-4-yl-N8-(2,4,6-trifluorophenyl)purine-2,8-diamine; hydrochloride (68 mg, 62%) as a white solid.

ESI-MS m/z: 441.2 $(M+H)^+$; $^1$H NMR (400 MHz, Methanol-$d_4$) δ 7.87 (s, TH), 7.56-7.44 (m, 4H), 7.32-7.25 (in, 1H), 7.10-7.02 (m, 2H), 4.76 (tt, J=12.1, 4.2 Hz, TH), 4.12 (dd, J=11.7, 4.5 Hz, 2H), 3.58 (td, J=12.2, 1.9 Hz, 2H), 2.86 (m, 2H), 1.93 m, 2H). HRMS calcd for $[C_{22}H_{19}F_3N_6O+H]^+$: 441.16452, Found: 441.16519. Anal. calcd for $[C_{22}H_{20}ClF_3N_6O]$: C, 55.41; H, 4.23; Cl, 7.43; N, 17.62. Found: C, 55.22; H, 4.21; Cl, 7.31; N, 17.54.

All other analogs shown in Table 1 below were also synthesized by following the above synthetic procedures.

TABLE 1
| No. | Structure | HRMS | $^1$H NMR (400 MHz, D$_2$O or MeOH-d$_4$) | HPLC Purity (%) |
|---|---|---|---|---|
| 1 | 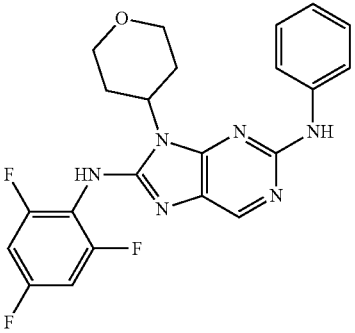 [SMILES: Fc1cc(F)c(Nc2nc3cnc(Nc4ccccc4)nc3n2C2CCOCC2)c(F)c1] | Calculated: 441.16452, Found: 441.16519 | δ 7.87 (s, 1H), 7.56-7.44 (m, 4H), 7.32-7.25 (m, 1H), 7.10-7.02 (m, 2H), 4.76 (tt, J = 12.1, 4.2 Hz, 1H), 4.12 (dd, J = 11.7, 4.5 Hz, 2H), 3.58 (td, J = 12.2, 1.9 Hz, 2H), 2.86 (m, 2H), 1.93 m, 2H). | 99.2 |
| 2 | 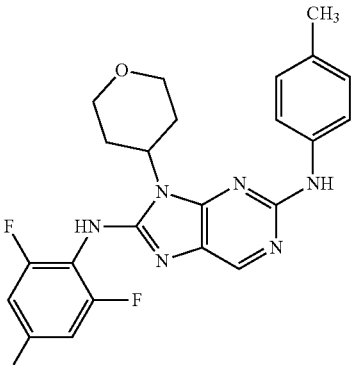 | Calculated: 455.18017, Found: 455.18035 | δ 7.84 (s, 1H), 7.39 (d, J = 8.4 Hz, 2H), 7.30 (d, J =7.9 Hz, 2H), 7.07 (dd, J = 8.9, 7.8 Hz, 2H), 4.77 (tt, J = 12.1, 4.1 Hz, 1H), 4.12 (dd, J = 11.8, 4.5 Hz, 2H), 3.59 (td, J = 12.2, 1.8 Hz, 2H), 2.85 (m, 2H), 2.38 (s, 3H), 1.98-1.88 (m, 2H). | 99.6 |
| 3 | 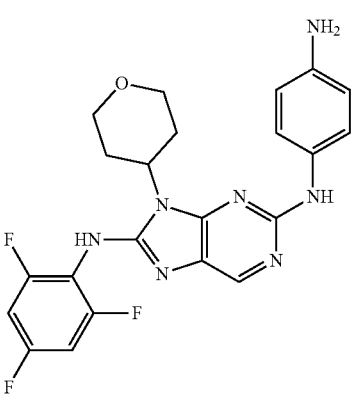 | Calculated: 456.17542, Found: 456.17539 | δ 8.12 (s, 1H), 7.82-7.76 (m, 2H), 7.51-7.46 (m, 2H), 7.16-7.07 (m, 2H), 4.80 (m, 1H), 4.12 (dd, J = 11.8, 4.5 Hz, 2H), 3.60 (td, J = 12.2, 1.9 Hz, 2H), 2.83 (m, 2H), 2.00-1.92 (m, 2H). | 98.0 |
| 4 | 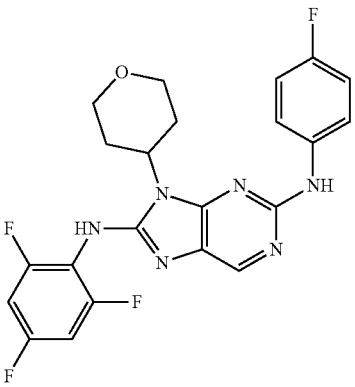 | Calculated: 459.15510, Found: 459.15535 | δ 7.91 (s, 1H), 7.57-7.51 (m, 2H), 7.26-7.18 (m, 2H), 7.12-7.03 (m, 2H), 4.77 (tt, J = 12.0, 4.1 Hz, 1H), 4.12 (dd, J = 11.8, 4.5 Hz, 2H), 3.58 (td, J = 12.2, 1.9 Hz, 2H), 2.81 (m, 2H), 1.93 (m, 2H). | 99.4 |

TABLE 1-continued

| No. | Structure | HRMS | ¹H NMR (400 MHz, D₂O or MeOH-d₄) | HPLC Purity (%) |
|---|---|---|---|---|
| 5 | 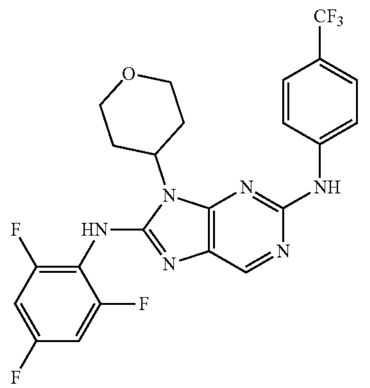 [SMILES: Fc1cc(F)c(Nc2nc3cnc(Nc4ccc(C(F)(F)F)cc4)nc3n2C2CCOCC2)c(F)c1] | Calculated: 509.15190, Found: 509.15234 | δ 8.17 (s, 1H), 7.83 (d, J = 8.4 Hz, 2H), 7.72 (d, J = 8.5 Hz, 2H), 7.18-7.09 (m, 2H), 4.82 (tt, J = 12.0, 4.2 Hz, 1H), 4.16 (dd, J = 11.8, 4.6 Hz, 2H), 3.61 (td, J = 12.1, 1.8 Hz, 2H), 2.89 (m, 2H), 2.02-1.94 (m, 2H). | 99.7 |
| 6 | 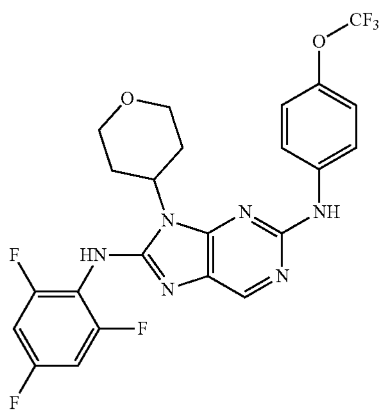 [SMILES: Fc1cc(F)c(Nc2nc3cnc(Nc4ccc(OC(F)(F)F)cc4)nc3n2C2CCOCC2)c(F)c1] | Calculated: 525.14682, Found: 525.14652 | δ 7.99 (s, 1H), 7.70-7.64 (m, 2H), 7.37 (m, 2H), 7.13-7.03 (m, 2H), 4.76 (tt, J = 12.1, 4.2 Hz, 1H), 4.13 (dd, J = 11.8, 4.6 Hz, 2H), 3.59 (td, J = 12.2, 2.0 Hz, 2H), 2.85 (m, 2H), 1.99-1.89 (m, 2H). | 99.4 |
| 7 | 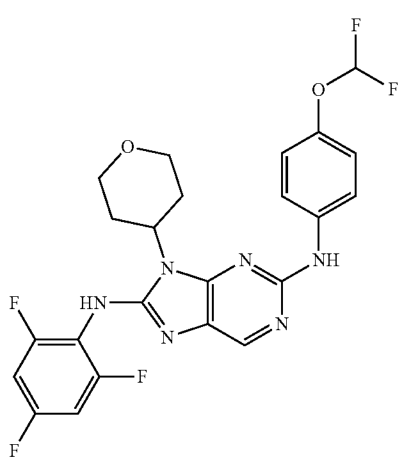 [SMILES: Fc1cc(F)c(Nc2nc3cnc(Nc4ccc(OC(F)F)cc4)nc3n2C2CCOCC2)c(F)c1] | Calculated: 507.15624, Found: 507.15658 | δ 7.91 (s, 1H), 7.61-7.54 (m, 2H), 7.28-7.22 (m, 2H), 7.07 (m, 2H), 6.85 (t, J = 74.0 Hz, 1H), 4.75 (tt, J = 12.1, 4.2 Hz, 1H), 4.13 (dd, J = 11.7, 4.5 Hz, 2H), 3.58 (td, J = 12.2, 1.9 Hz, 2H), 2.92-2.76 (m, 2H), 1.97-1.87 (m, 2H). | 96.8 |

TABLE 1-continued

| No. | Structure | HRMS | ¹H NMR (400 MHz, D₂O or MeOH-d₄) | HPLC Purity (%) |
|---|---|---|---|---|
| 8 | 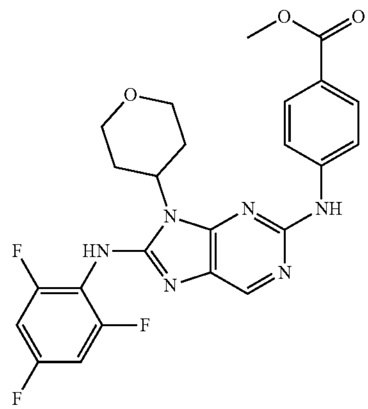 [SMILES: COC(=O)c1ccc(Nc2ncc3nc(Nc4c(F)cc(F)cc4F)n(C4CCOCC4)c3n2)cc1] | Calculated: 499.17000, Found: 498.17013 | δ 8.16 (s, 1H), 8.07-8.03 (m, 2H), 7.79-7.75 (m, 2H), 7.15-7.07 (m, 2H), 4.78 (tt, J = 12.0, 4.2 Hz, 1H), 4.17 (dd, J = 11.7, 4.6 Hz, 2H), 3.90 (s, 3H), 3.61 (td, J = 12.2, 1.8 Hz, 2H), 2.92 (m, 2H), 2.02-1.91 (m, 2H). | 98.6 |
| 9 | 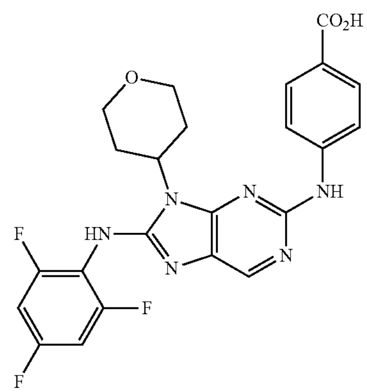 [SMILES: O=C(O)c1ccc(Nc2ncc3nc(Nc4c(F)cc(F)cc4F)n(C4CCOCC4)c3n2)cc1] | Calculated: 485.15435, Found: 485.15474 | δ 8.14 (s, 1H), 8.11-8.06 (m, 2H), 7.77-7.71 (m, 2H), 7.17-7.08 (m, 2H), 4.81 (tt, J = 12.0, 4.2 Hz, 1H), 4.17 (dd, J = 12.0, 4.3 Hz, 2H), 3.61 (td, J = 12.2, 1.8 Hz, 2H), 2.90 (m, 2H), 2.03-1.94 (m, 2H). | 96.0 |
| 10 | 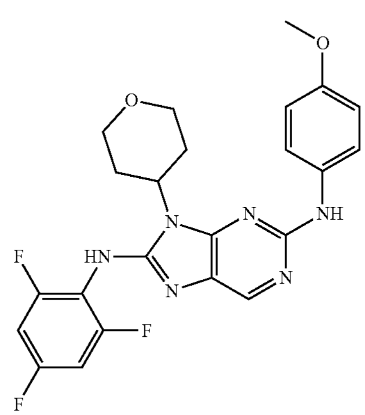 [SMILES: COc1ccc(Nc2ncc3nc(Nc4c(F)cc(F)cc4F)n(C4CCOCC4)c3n2)cc1] | Calculated: 471.17509, Found: 471.17530 | δ 7.73 (s, 1H), 7.43-7.35 (m, 2H), 7.11-6.99 (m, 4H), 4.74 (tt, J = 12.1, 4.2 Hz, 1H), 4.12 (dd, J = 11.4, 4.8 Hz, 2H), 3.84 (s, 3H), 3.58 (td, J = 12.2, 1.8 Hz, 2H), 2.85 (m, 2H), 1.92 (m, 2H). | 98.7 |

TABLE 1-continued

| No. | Structure | HRMS | ¹H NMR (400 MHz, D$_2$O or MeOH-d$_4$) | HPLC Purity (%) |
|---|---|---|---|---|
| 11 | 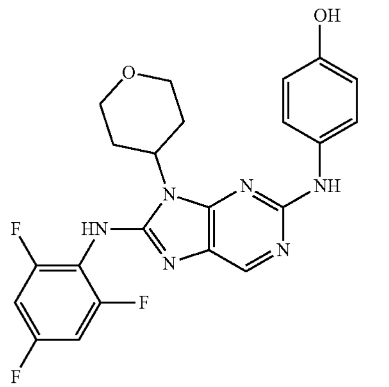 | Calculated: 457.15943, Found: 457.15993 | δ 7.71 (s, 1H), 7.31-7.25 (m, 2H), 7.04 (t, J = 8.5 Hz, 2H), 6.92-6.86 (m, 2H), 4.81-4.67 (m, 1H), 4.12 (dd, J = 11.7, 4.5 Hz, 2H), 3.58 (td, J = 12.1, 1.9 Hz, 2H), 2.87 (m, 2H), 1.91 (m, 2H). | 96.4 |
| 12 | 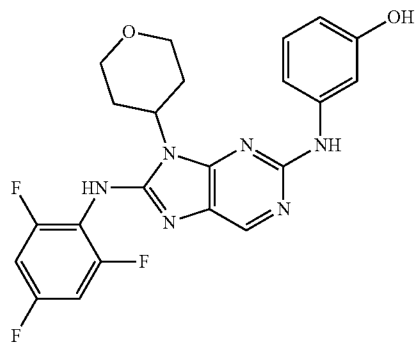 [SMILES: Oc1cccc(Nc2ncc3nc(Nc4c(F)cc(F)cc4F)n(C4CCOCC4)c3n2)c1] | Calculated: 457.15943, Found: 457.16025 | δ 7.82 (s, 1H), 7.28 (t, J = 7.9 Hz, 1H), 7.11-7.03 (m, 2H), 6.97 (ddd, J = 8.0, 2.1, 0.9 Hz, 1H), 6.91 (t, J = 2.2 Hz, 1H), 6.74 (ddd, J = 8.2, 2.4, 0.9 Hz, 1H), 4.76 (tt, J = 12.1, 4.2 Hz, 1H), 4.13 (dd, J = 11.7, 4.6 Hz, 2H), 3.59 (td, J = 12.2, 1.9 Hz, 2H), 2.88 (m, 2H), 1.94 (m, 2H). | 98.5 |
| 13 | 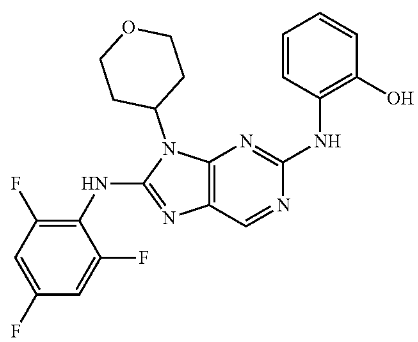 [SMILES: Oc1ccccc1Nc1ncc2nc(Nc3c(F)cc(F)cc3F)n(C3CCOCC3)c2n1] | Calculated: 457.15943, Found: 457.16008 | δ 7.83 (s, 1H), 7.69-7.60 (m, 1H), 7.14 (ddd, J = 8.1, 7.3, 1.6 Hz, 1H), 7.09-6.99 (m, 2H), 6.99-6.90 (m, 2H), 4.75 (m, 1H), 4.14 (dd, J = 11.7, 4.5 Hz, 2H), 3.59 (td, J = 12.2, 1.9 Hz, 2H), 2.91 (m, 2H), 1.97-1.86 (m, 2H). | 99.2 |
| 14 | 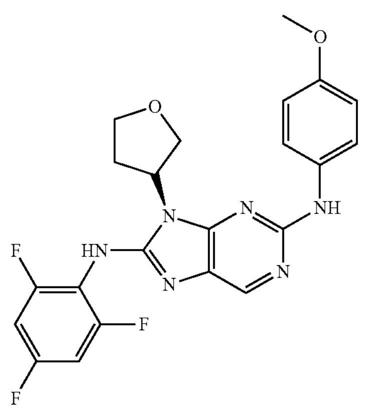 | Calculated: 457.15943, Found: 457.15980 | δ 7.81 (s, 1H), 7.44-7.36 (m, 2H), 7.10-6.98 (m, 4H), 5.40-5.30 (m, 1H), 4.31 (dd, J = 9.9, 4.1 Hz, 1H), 4.25 (m, 1H), 4.08 (dd, J = 10.0, 6.9 Hz, 1H), 3.92-3.85 (m, 1H), 3.84 (s, 3H), 2.58 (m, 2H). | 99.0 |

TABLE 1-continued

| No. | Structure | HRMS | ¹H NMR (400 MHz, D$_2$O or MeOH-d$_4$) | HPLC Purity (%) |
|---|---|---|---|---|
| 15 | 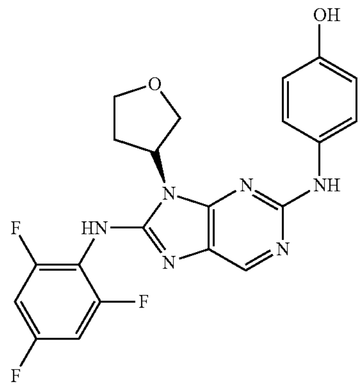 | Calculated: 443.14378, Found: 443.14369 | δ 7.78 (s, 1H), 7.32-7.24 (m, 2H), 7.09-6.98 (m, 2H), 6.91-6.83 (m, 2H), 5.34 (m, 1H), 4.33-4.21 (m, 2H), 4.07 (dd, J = 9.9, 6.9 Hz, 1H), 3.94-3.82 (m, 1H), 2.57 (m, 2H). | 97.1 |
| 16 | 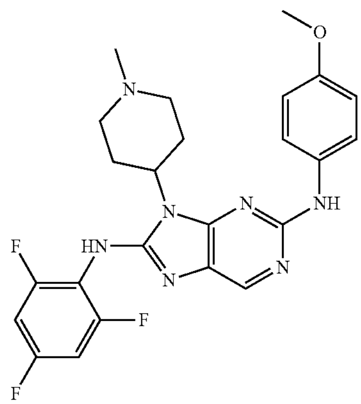 [SMILES: COc1ccc(Nc2ncc3nc(Nc4c(F)cc(F)cc4F)n(C4CCN(C)CC4)c3n2)cc1] | Calculated: 484.20672, Found: 484.20712 | δ 7.68-7.46 (broad s, 1H), 7.40-7.35 (m, 2H), 7.10-7.04 (m, 2H), 7.04-6.95 (m, 2H), 3.85 (s, 3H), 3.78-3.68 (m, 2H), 3.55-3.42 (m, 1H), 3.30-3.23 (m, 2H), 3.22-3.07 (m, 2H), 2.94 (s, 3H), 2.29 (m, 2H). | 95.6 |
| 17 | 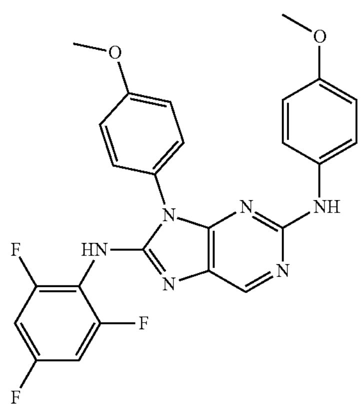 [SMILES: COc1ccc(Nc2ncc3nc(Nc4c(F)cc(F)cc4F)n(-c4ccc(OC)cc4)c3n2)cc1] | Calculated: 493.15943, Found: 493.15979 | δ 7.90 (s, 1H), 7.58-7.52 (m, 2H), 7.35-7.29 (m, 2H), 7.24-7.17 (m, 2H), 7.08-7.00 (m, 2H), 7.00-6.93 (m, 2H), 3.91 (s, 3H), 3.80 (s, 3H). | 98.9 |
| 18 | 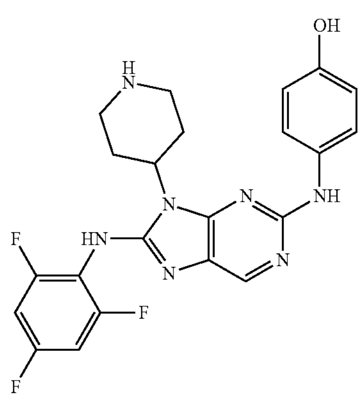 [SMILES: Oc1ccc(Nc2ncc3nc(Nc4c(F)cc(F)cc4F)n(C4CCNCC4)c3n2)cc1] | Calculated: 456.17542, Found: 456.17475 | δ 7.56 (broad s, 1H), 7.29-7.23 (m, 2H), 7.01 (m, 2H), 6.95-6.87 (m, 2H), 4.90 (broad m, 1H), 3.68-3.58 (m, 2H), 3.23 (td, J = 13.2, 2.7 Hz, 2H), 3.04 (m, 2H), 2.26 (m, 2H). | 98.3 |

TABLE 1-continued

| No. | Structure | HRMS | $^1$H NMR (400 MHz, D$_2$O or MeOH-d$_4$) | HPLC Purity (%) |
|---|---|---|---|---|
| 19 | 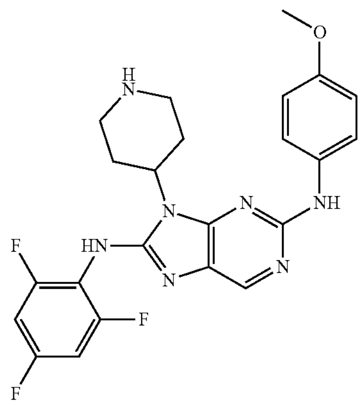 [SMILES: COc1ccc(Nc2ncc3nc(Nc4c(F)cc(F)cc4F)n(C4CCNCC4)c3n2)cc1] | Calculated: 470.19107, Found: 470.19091 | δ 7.82 (s, 1H), 7.39 (d, J = 9.0 Hz, 2H), 7.12 (d, J = 8.6 Hz, 2H), 7.03 (t, J = 8.7 Hz, 2H), 4.75-4.66 (m, 1H), 3.88 (s, 3H), 3.67 (d, J = 13.0 Hz, 2H), 3.23 (t, J = 13.1 Hz, 2H), 2.99-2.83 (m, 2H), 2.35 (d, J = 13.9 Hz, 2H). | 97.9 |
| 20 | 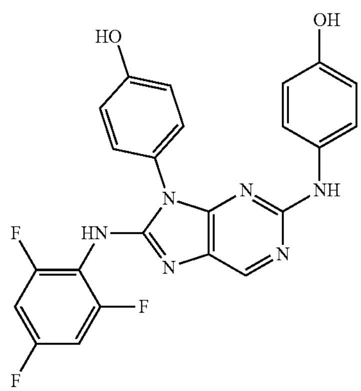 [SMILES: Oc1ccc(Nc2ncc3nc(Nc4c(F)cc(F)cc4F)n(-c4ccc(O)cc4)c3n2)cc1] | Calculated: 465.12813, Found: 465.12762 | δ 7.86 (s, 1H), 7.46-7.40 (m, 2H), 7.25-7.18 (m, 2H), 7.08-6.98 (m, 4H), 6.86-6.79 (m, 2H). | 99.7 |
| 21 | 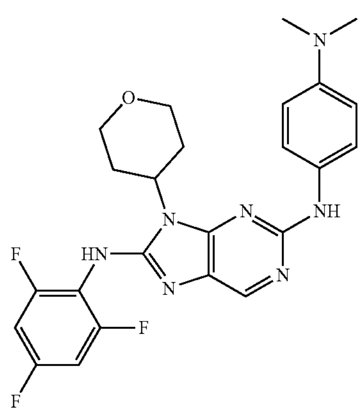 [SMILES: CN(C)c1ccc(Nc2ncc3nc(Nc4c(F)cc(F)cc4F)n(C4CCOCC4)c3n2)cc1] | Calculated: 484.20672, Found: 484.20606 | δ 8.33 (s, 1H), 7.57-7.50 (m, 2H), 7.50-7.44 (m, 2H), 7.16-7.07 (m, 2H), 4.72 m, 1H), 4.03 (dd, J = 11.7, 4.6 Hz, 2H), 3.54 (td, J = 12.1, 1.8 Hz, 2H), 3.30 (s, 6H), 2.62 (m, 2H), 1.93-1.84 (m, 2H). | 97.4 |

TABLE 1-continued

| No. | Structure | HRMS | $^1$H NMR (400 MHz, D$_2$O or MeOH-d$_4$) | HPLC Purity (%) |
|---|---|---|---|---|
| 22 | 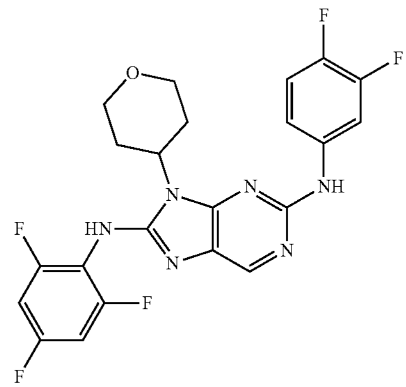 [SMILES: Fc1cc(F)c(Nc2nc3cnc(Nc4ccc(F)c(F)c4)nc3n2C2CCOCC2)c(F)c1] | Calculated: 477.14568, Found: 477.14621 | δ 8.03 (s, 1H), 7.68-7.60 (m, 1H), 7.38-7.28 (m, 2H), 7.14-7.04 (m, 2H), 4.76 (m, 1H), 4.13 (dd, J = 11.8, 4.6 Hz, 2H), 3.59 (td, J = 12.2, 1.9 Hz, 2H), 2.84 (m, 2H), 1.95 (m, 2H). | 99.8 |
| 23 | 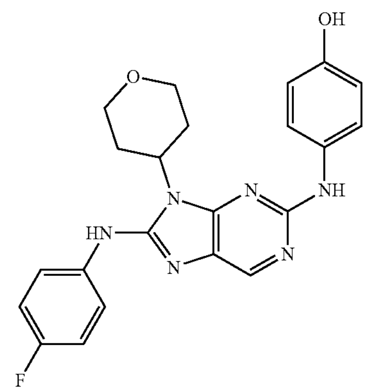 [SMILES: Oc1ccc(Nc2ncc3nc(Nc4ccc(F)cc4)n(C4CCOCC4)c3n2)cc1] | Calculated: 421.17828, Found: 421.17836 | δ 7.95 (s, 1H), 7.71-7.64 (m, 2H), 7.33-7.19 (m, 4H), 6.94-6.87 (m, 2H), 4.77 (m, 1H), 4.12 (dd, J = 11.8, 4.5 Hz, 2H), 3.60 (td, J = 12.2, 1.9 Hz, 2H), 2.87 (m, 2H), 1.96 (m, 2H). | 99.2 |
| 24 | 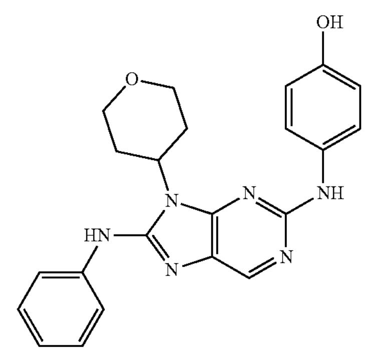 [SMILES: Oc1ccc(Nc2ncc3nc(Nc4ccccc4)n(C4CCOCC4)c3n2)cc1] | Calculated: 403.18770, Found: 403.18766 | δ 7.95 (s, 1H), 7.68-7.61 (m, 2H), 7.54-7.46 (m, 2H), 7.38-7.32 (m, 1H), 7.32-7.26 (m, 2H), 6.94-6.88 (m, 2H), 4.78 (m, 1H), 4.12 (dd, J = 11.8, 4.5 Hz, 2H), 3.60 (td, J = 12.0, 1.8 Hz, 2H), 2.88 (m, 2H), 2.02-1.92 (m, 2H). | 99.3 |
| 25 | 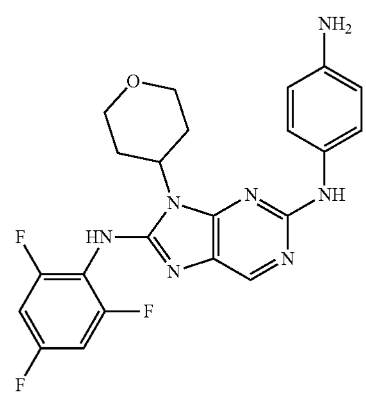 [SMILES: Nc1ccc(Nc2ncc3nc(Nc4c(F)cc(F)cc4F)n(C4CCOCC4)c3n2)cc1] | Calculated: 457.15943, Found: 457.15943 | δ 8.14 (s, 1H), 7.85 (d, J = 9.0 Hz, 2H), 7.65 (d, J = 8.9 Hz, 2H), 7.16-7.07 (m, 2H), 4.79 (m, 1H), 4.15 (dd, J = 11.8, 4.6 Hz, 2H), 3.61 (td, J = 12.4, 2.0 Hz, 2H), 2.96-2.80 (m, 2H), 2.01-1.92 (m, 2H). | 96.2 |

TABLE 1-continued

| No. | Structure | HRMS | ¹H NMR (400 MHz, D₂O or MeOH-d₄) | HPLC Purity (%) |
|---|---|---|---|---|
| 26 | 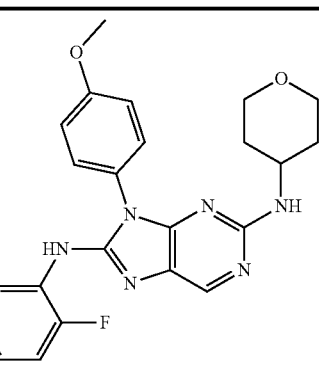 | Calculated: 471.17509, Found: 471.17468 | δ 7.95 (s, 1H), 7.56-7.49 (m, 2H), 7.23-7.17 (m, 2H), 7.08-6.99 (m, 2H), 3.91 (m, 6H), 3.44 (td, J = 11.7, 2.3 Hz, 2H), 1.97-1.87 (m, 2H), 1.60 (m, 2H). | 99.9 |
| 27 | 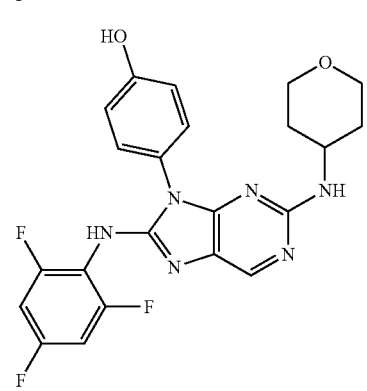 [SMILES: COc1ccc(-n2c(Nc3c(F)cc(F)cc3F)nc3cnc(NC4CCOCC4)nc32)cc1] | Calculated: 457.15943, Found: 457.15997 | δ 7.95 (s, 1H), 7.43-7.36 (m, 2H), 7.02 (m, 4H), 3.92 (m, 3H), 3.45 (td, J = 11.6, 2.2 Hz, 2H), 1.97-1.88 (m, 2H), 1.58 (m, 2H). | 99.0 |

2. Evaluation of Purine Diamines

The activity of exemplary compounds against BRD4, RIPK3, and IL6 is shown in Table 2 below.

TABLE 2

| | IC50 (μM) | | |
|---|---|---|---|
| No. | BRD4 | RIPK3 | IL6 |
| 1 | 15.04 | 0.16 | 0.34 |
| 2 | 29.62 | 0.88 | 0.88 |
| 3 | 5.64 | <0.08 | 0.26 |
| 4 | 3.17 | 0.59 | 0.50 |
| 5 | 24.64 | >40 | 1.17 |
| 6 | 13.48 | >40 | 0.88 |
| 7 | 4.50 | 0.61 | 0.31 |
| 8 | 16.26 | 17.54 | 1.60 |
| 9 | >40 | <0.08 | 19.12 |
| 10 | 6.26 | 0.54 | 0.64 |
| 11 | 0.52 | 0.09 | 0.61 |
| 12 | 11.83 | 0.09 | 0.28 |
| 13 | 39.80 | >40 | N.T. |
| 14 | 9.41 | 1.33 | 2.19 |
| 15 | 1.21 | 0.31 | 1.07 |
| 16 | 23.70 | 2.43 | <0.098 |
| 17 | 11.58 | 5.81 | 7.80 |
| 18 | 6.87 | 0.01 | 0.05 |
| 19 | 15.88 | 0.11 | 0.01 |
| 20 | 1.71 | 1.45 | <0.2 |
| 21 | 3.76 | 0.22 | <0.1 |
| 22 | 2.02 | 6.48 | 1.51 |
| 23 | 0.69 | 0.77 | 0.45 |
| 24 | 0.77 | 0.43 | 0.53 |
| 25 | >40 | 36.66 | <0.1 |
| 26 | 39.54 | >40 | N.T. |
| 27 | 21.43 | 27.99 | 0.28 |

3. In Vivo Efficacy of BRD4-RIPK3 Dual Inhibitor, Compound No. 11, in Pre-Clinical Models of Arsenicals-Induced Cutaneous Vesicants Injury BRD4 is an epigenetic regulatory protein involved in various pro-inflammatory, hyper-proliferative, and tissue remodeling diseases. RIP kinase are involved in tissue damage and remodeling. BRD4 regulates RIPK3 but it is also independently regulated. Arsenicals are highly toxic and induce severe tissue damge. This led to their selection as chemical weapons. It was found that arsenicals induce moleculer pathogensis of inflammation and tissue damage involves activation of chromating modifier, BRD4, and kinases involved in tissue necrosis including RIP kinases. Here, SRI43387 was tested in two models of arsenicals-induced skin injury as described below.

a. BRD4-RIPK3 Inhibition-Dependent Protection of SRI43387 Against PAO-Induced Cutaneous Injury Phenylarsine Oxide (PAO) is a surrogate arsenical developed in the laboratory of Dr. Mohammad Athar to investigate the effects of highly toxic warfare grade arsenicals such as lewisite. PAO manifests similar vesicant skin injury as observed by lewisite. However, the dose regimen for the two chemicals are different. First, it was discovered that PAO-induced cutaneous injury is mediated by the activation of BRD4-RIPK3 signaling. Three distinct doses of compound no. 11 were topically administered in PAO-challenged animals. Compound no. 11 was administered 10 minutes after PAO treatment. The animals were observed for injury progression upto 24 hrs. However, the animals were sacrificed at 6 and 24 hrs after PAO challenge. In each group, 6 animals were recruited. This protocol is summarized in FIG. 1A.

Figure 1B:
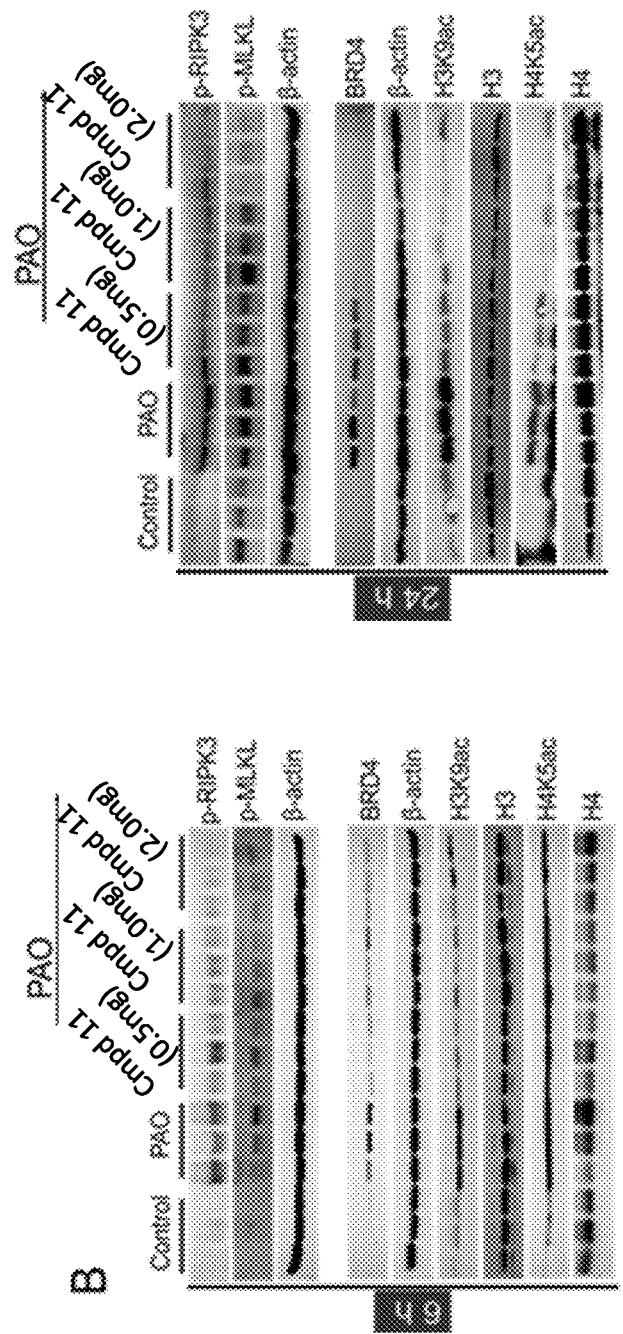

In FIG. 1B the western blot analysis of BRD4 and RIPK3 signaling in PAO-challenged skin is shown, and the effects of administration of various doses of SRI433387 on these signaling pathways was evaluated. The RIPK3 signaling activation is represented by the enhancement in the phosphorylation of RIPK3 and its downstream pseudo-kinase MLKL. Accordingly, it was found that PAO challenge induces phosphorylation of RIPK3 and MLKL and treatment with compound no. 11 significantly reduces this signaling in a dose-dependent manner.

Figure 1C:
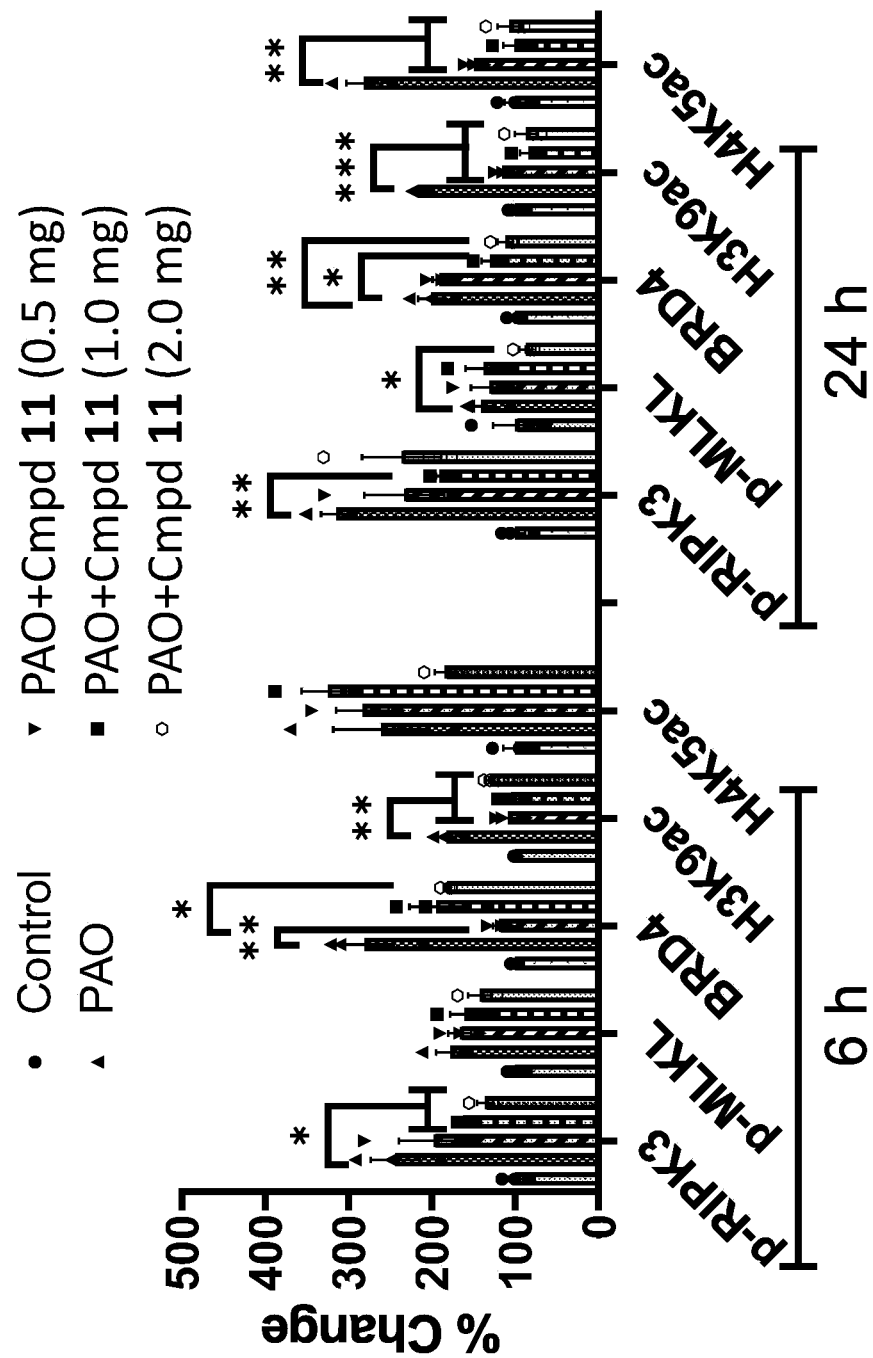

Densitometry analysis of western blots demonstrate that BRD4-dependent chromatin remodeling is characterized by the high expression of BRD4 and downstream histone H3 and H4 acetylation marks. Here, in FIG. 1C, H3K9ac and H4K5ac histone mark were assessed. PAO-induced the expression of BRD4 and histone marks H3K9ac and H4K5ac significantly. Treatment with compound no. 11 significantly reduced BRD4 expression and BRD4-dependent H3 and H4 histone marks in a dose-dependent manner. Identical responses of efficacy of compound no. 11 were found at 6 h and 24 hrs post PAO exposure.

Figure 1D:
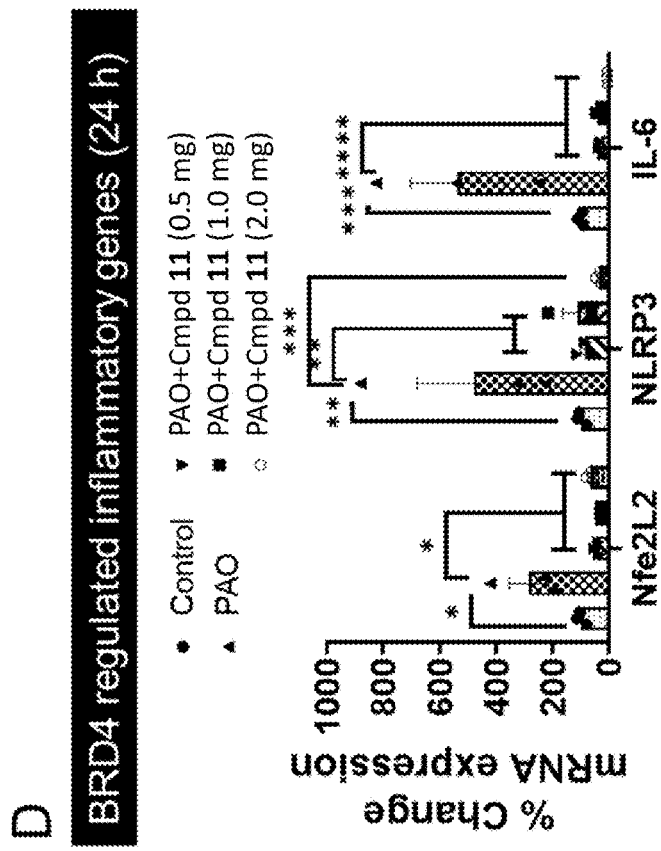

After demonstration that compound no. 11 is able to inhibit both BRD4 and RIPK3, its impact on inflammatory signaling was further validated (FIG. 1D). In this case, the mRNA expression of BRD4-regulated inflammatory genes was assessed at 24 hrs. These genes include Nfe2l2, NLRP3, and IL-6, which were induced by PAO significantly. However, treatment with compound no. 11 was highly effective and decreased their levels even below the vehicle-treated control level. BRD4 regulated genes involved in tissue damage were further assessed, and the expression of Foxo3, Cxcl13, and Pel1 were evaluated. A diminution in the expression of mRNA of these genes was found by compound no. 11 treatment. Moreover, as compared to inflammation related genes, the effect of compound no. 11 was less significant on tissue damage related genes at 24 hrs.

Figure 2A:
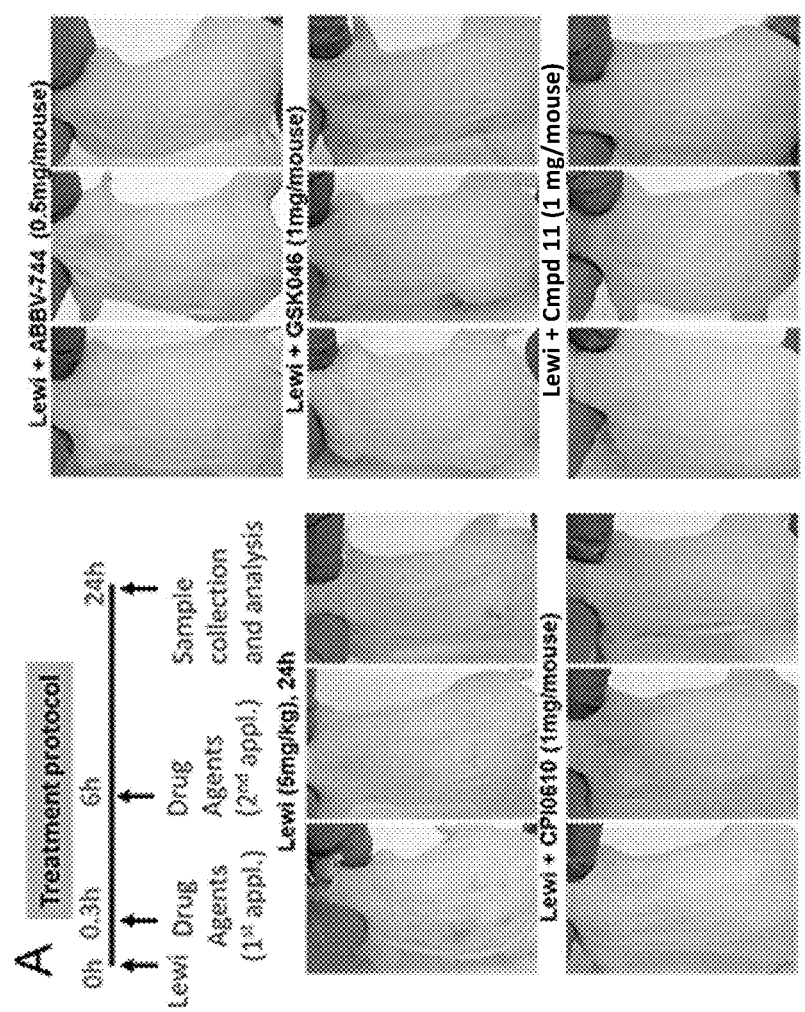
FIG. 2A-J show the effects of compound no. 11 and other BRD4 inhibitors on Lewisite-induced skin injury. Specifically.
Figure 2B:
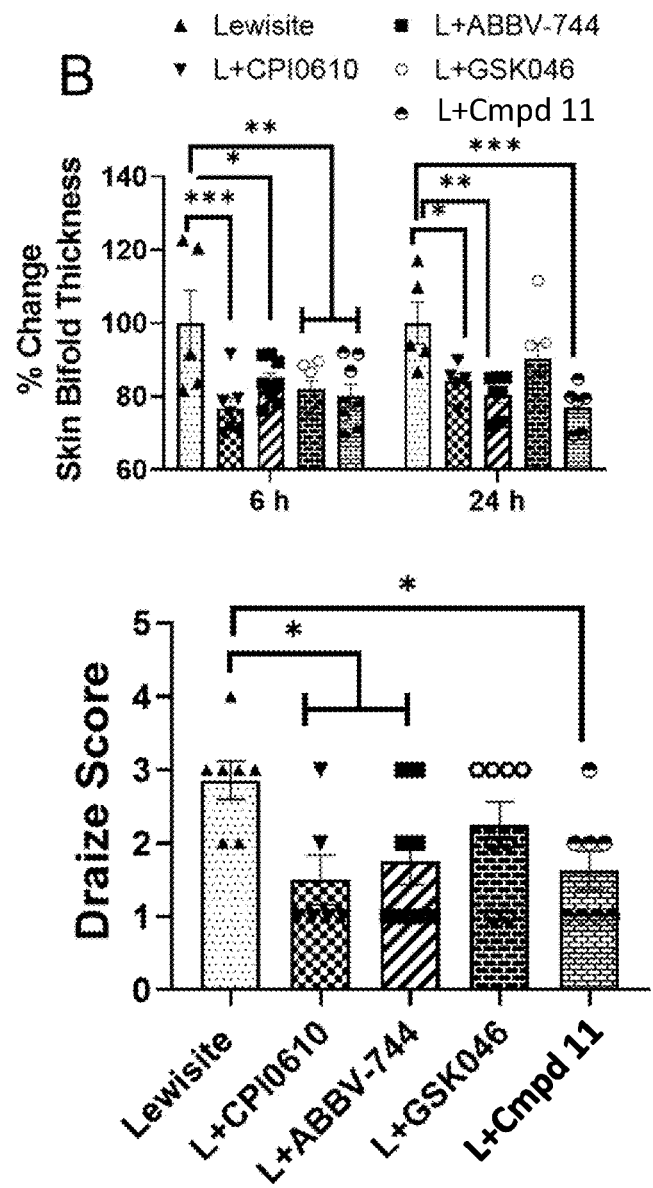
Figure 2C:
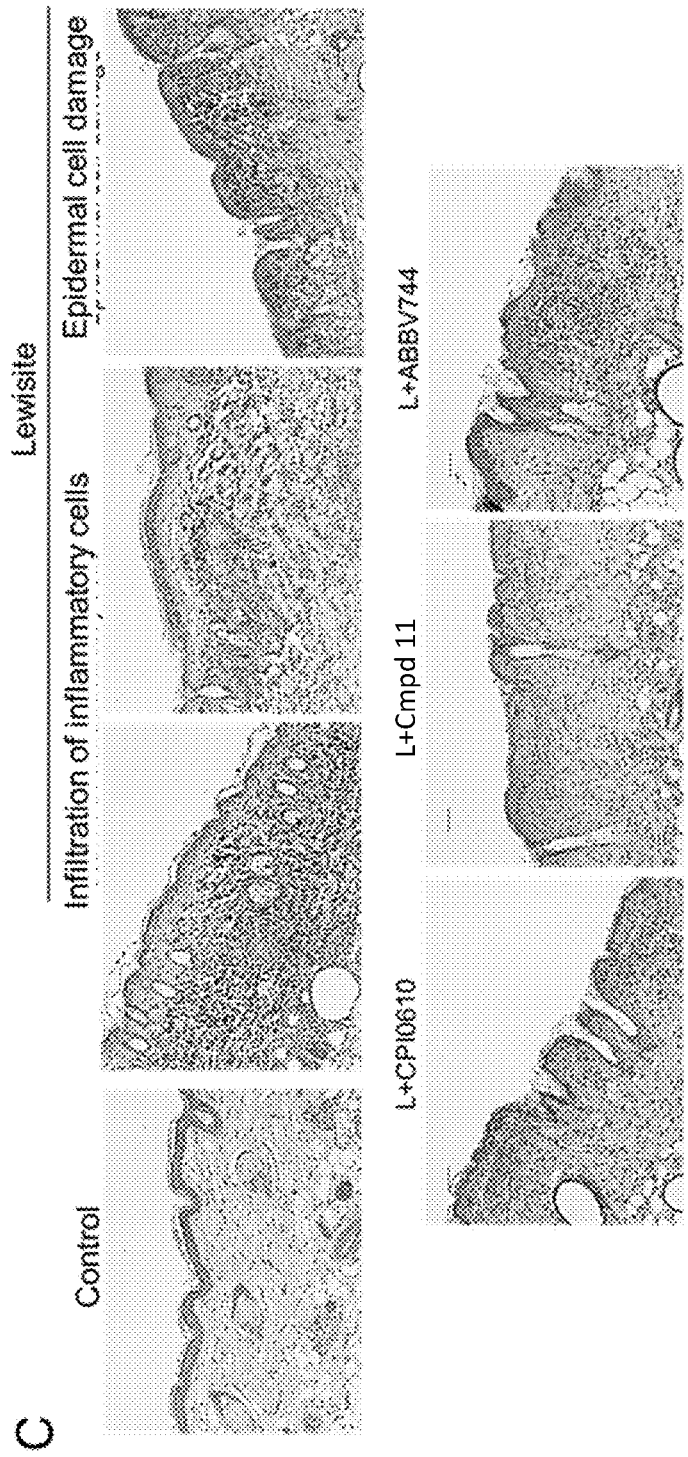

In summary, it is herein described that compound no. 11 acts by inhibiting both BRD4 and RIPK3 signaling in the skin of PAO-challenged animals, and it reduces molecular target associated inflammatory response dose-dependently.
b. Comparative Evaluation of the Efficacy of Compound No. 11 and Other Known BRD4 Inhibitors in a Preclinical Murine Model of Lewisite-Induced Vesicant Injury From the studies described above, a dose of 1 mg/mouse of compound no. 11 was selected for investigations evaluating its efficacy against lewisite-induced skin injury. The lewisite challenge and drug treatment protocol is described in FIG. 2A-J. In this study, the effects of compound no. 11 were evaluated in a molecular target-specific manner. Additionally, its efficacy was also compared with other known BRD4 inhibitors, which are under clinical trails by various pharmaceutical companies for different diseases conditions. These BRD4 inhibitors include CPI0610 (Constellation Pharmaceuticals), ABBV-744 (AbbVie), and GSK046 (GlaxoSmithKline). As shown in FIG. 2A, compound no. 11 protected against lewisite-induced skin damage very significantly as assessed by the gross appearance of the skin conditions. In addition, skin bi-fold thickness measurement and Draize score calculation, which is based on the cumulative assessment of erythema, edema, and necrosis show a significant protection against lewisite-induced changes in these parameters. These changes are represented as comparative evaluation of these drugs using vehicle-treated skin of mice as control (FIG. 2B). Then, the histopathological changes were assessed in the skin of these animals as shown in FIG. 2C. Lewisite induced a very severe inflammatory response as could be seen by the huge infiltration of inflammatory cells and damage to epidermal cells. However, treatment of these mice with BRD4 inhibitors, CPI0610, ABBV-744, and compound no. 11 significantly reduced both infiltration of inflammatory cells into the dermis as well as it afforded protection against epidermal cell damage. The data for GSK046 is not shown here, as it afforded protection to the minimum level at a dose tested in these studies.

Figures 2D, 2E:
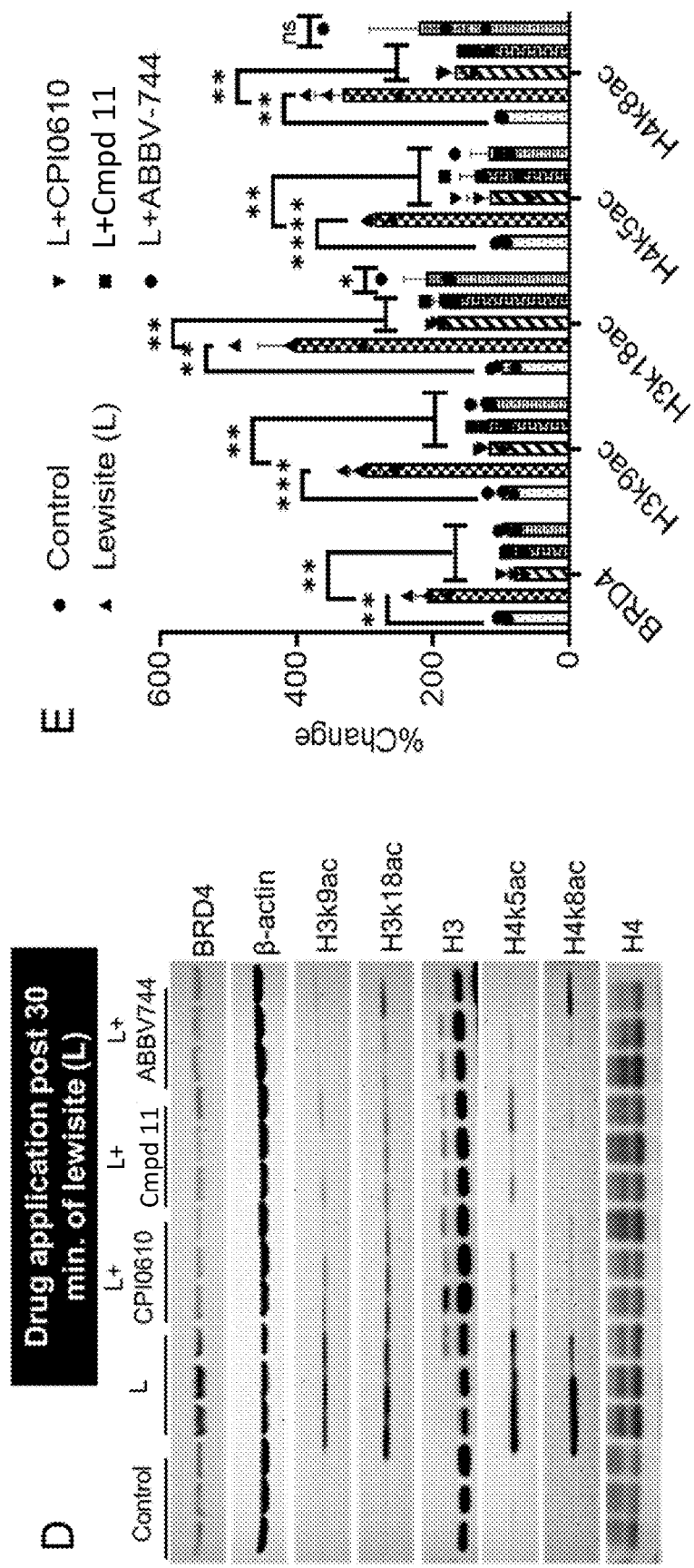
Figure 2F:
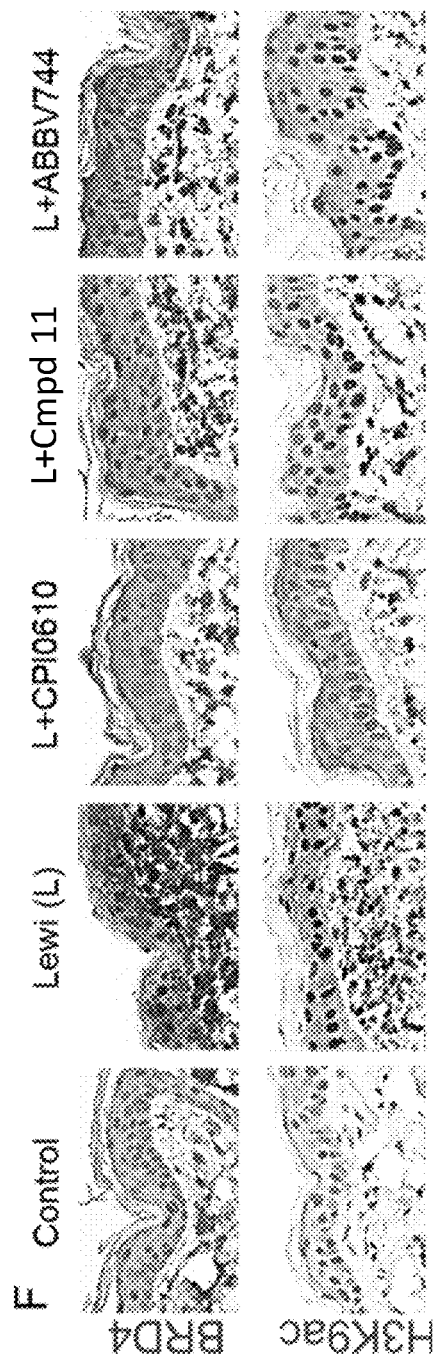
Figure 2H:
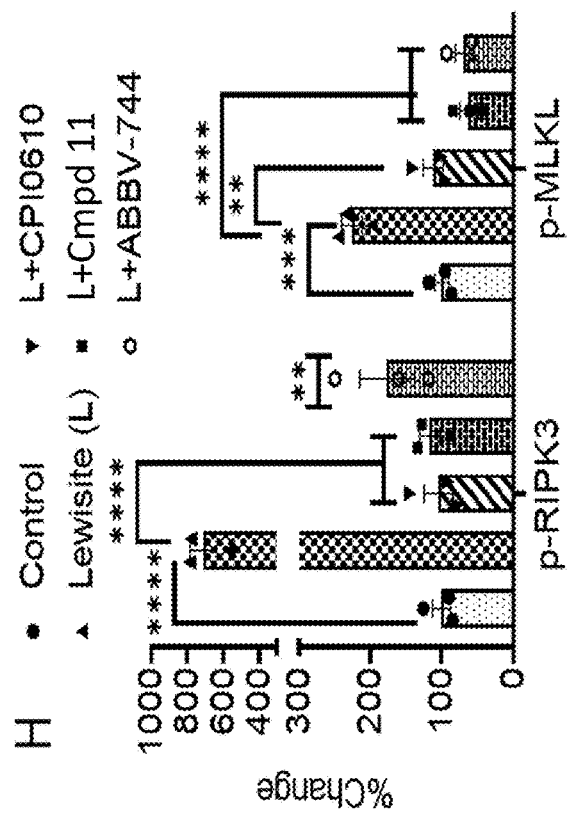
Figure 2G:
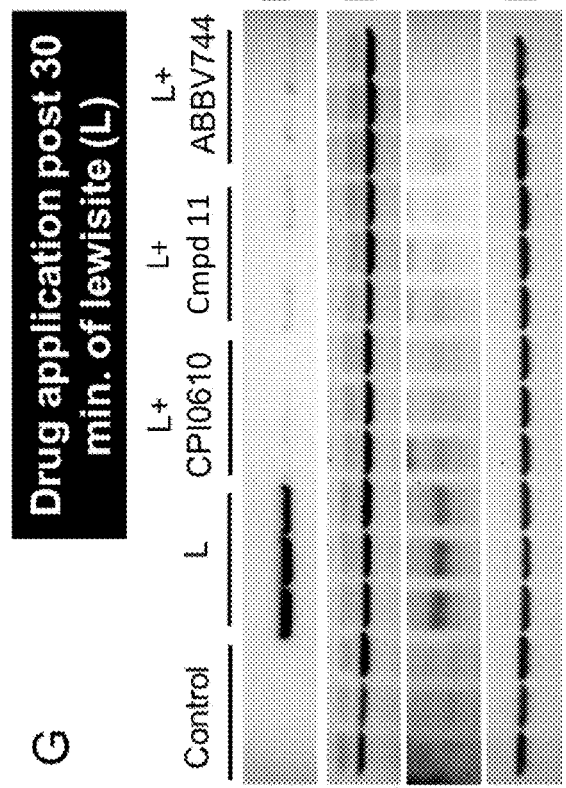

It was also confirmed that mechanistically compound no. 11 and other BRD4 inhibitors act similarly in response to lewisite-induced expression of BRD4 and its' signaling by enhancing H3 and H4 histone marks. In this study, two H3 histone marks, H3k9ac and H3k18ac, and two H4 histone marks, H4k5ac and H4K8ac, were ealuated. BRD4, as well as these H3 and H4 histone marks, show significant induction in their protein expression in lewisite-challenged animals (FIG. 2D). BRD4 inhibitors significantly reduced the expression of these proteins. Compound no. 11 was proved better or at least equally effective in attenuating the lewisite-induced expression of these histones as compared to CPI-0610 and ABBV-744. This is quantitatively assessed in FIG. 2E. Then, these data were confirmed in an immunohistochemical assay as shown in FIG. 2F. As compared to vehicle-treated control, the nuclear expression of these proteins was very high in lewisite-treated skin; however, as expected, compound no. 11 and other BRD4 inhibitors significantly reduced the nuclear expression of these proteins.

Figure 2J:
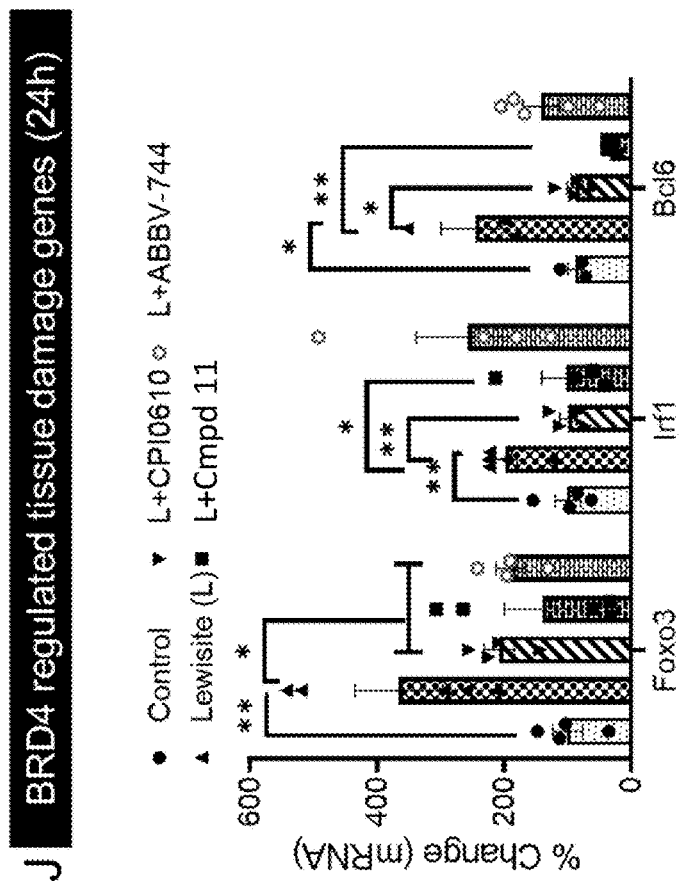
Figure 2I:
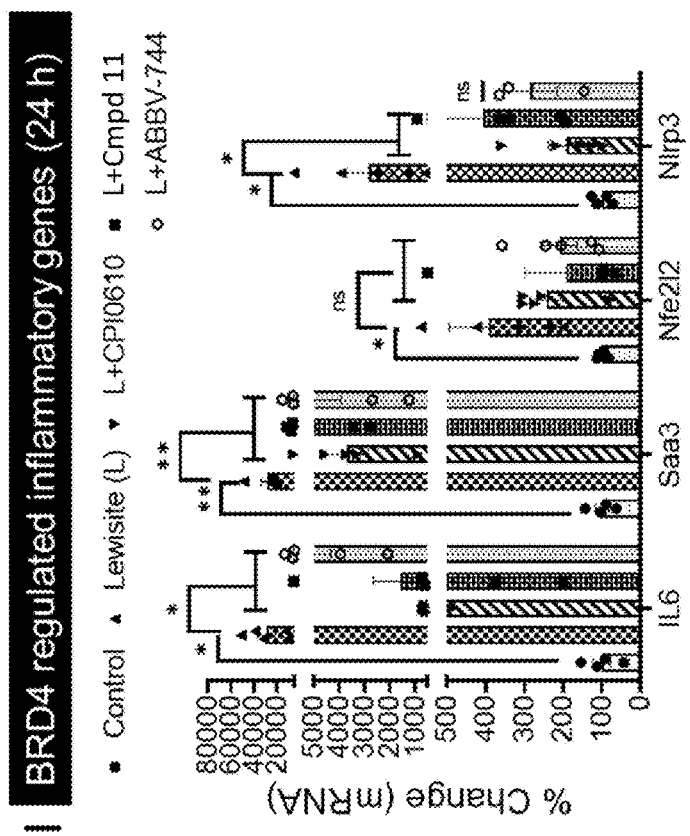

Then, whether RIPK3 signaling is also affected by treatment with these agents was tested. The data in FIG. 2G and FIG. 2H clearly demonstrate the attenuation of the lewisite-induced activation of RIPK signaling. Similar to the studies in the earlier described PAO model, it was found that compound no. 11 significantly reduced transcriptionally regulated BRD4-dependent inflammatory genes. Here, a panel of four genes, namely, IL-6, Saa3, Nfe2l2, and Nlrp3, was selected. The response of compound no. 11 was highly profound. It was effective in diminishing expression of all of these 4 genes (FIG. 2I). Similarly, the efficacy of these inhibitors was also tested against BRD4-regulated genes involved in skin tissue damage. A panel of 3 genes was selected; namely, Foxo3, Irf1, and Bcl6. Similar to the response of compound no. 11 in attenuating expression of inflammatory genes, it was also found that this agent was highly effective in attenuating the expression of genes associated with lewisite-induced skin tissue damage (FIG. 2J).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

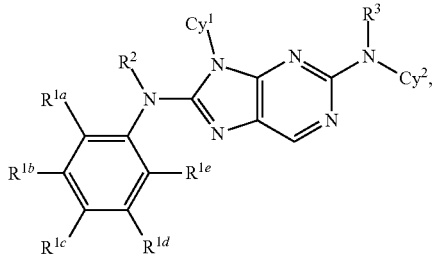

wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^2$ and $R^3$ is independently selected from hydrogen and C1-C4 alkyl;

wherein Cy$^1$ is a structure having a formula selected from:

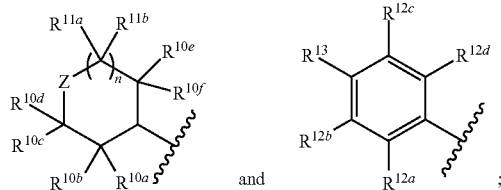

wherein n, when present, is 0 or 1;

wherein Z, when present, is selected from —O—, —S—, and —NR$^{20}$—;
  wherein R$^{20}$, when present, is selected from hydrogen and C1-C4 alkyl;

wherein each of $R^{10a}$, $R^{10b}$, $R^{10c}$, $R^{10d}$, $R^{10e}$, and $R^{10f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{11a}$ and $R^{11b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{12a}$, $R^{12b}$, $R^{12c}$, and $R^{12d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{13}$, when present, is selected from —OH, —NH$_2$, C1-C4 alkoxy, C1-C4 alkylamino, and (C1-C4)(C1-C4) dialkylamino; and wherein Cy$^2$ is a structure having a formula selected from:

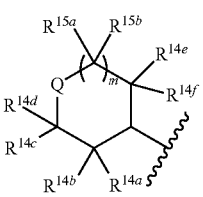 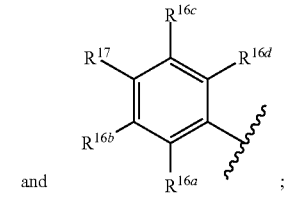

wherein m, when present, is 0 or 1;

wherein Q, when present, is selected from —O—, —S—, and —NR$^{21}$—;
  wherein R$^{21}$, when present, is selected from hydrogen and C1-C4 alkyl;

wherein each of $R^{14a}$, $R^{14b}$, $R^{14c}$, $R^{14d}$, $R^{14e}$, and $R^{14f}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{15a}$ and $R^{15b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{16a}$, $R^{16b}$, $R^{16c}$, and $R^{16d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^{17}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$_2$H, and —CO$_2$ (C1-C4 alkyl), provided that when Cy$^1$ is

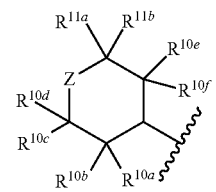

and at least seven of $R^{10a}$, $R^{10b}$, $R^{10c}$, $R^{10d}$, $R^{10e}$, $R^{10f}$, $R^{11a}$, and $R^{11b}$ are hydrogen, then each of $R^{1a}$, $R^{1c}$, and $R^{1e}$ is halogen, provided that when Cy$^1$ is

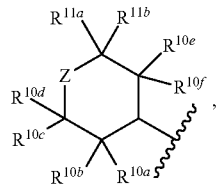

then Cy² is

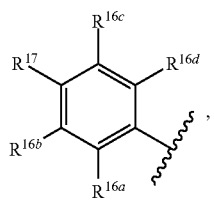

provided that when Cy¹ is

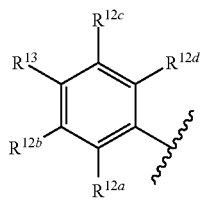

and Cy² is

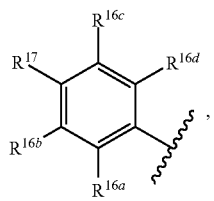

then $R^{17}$ is a non-hydrogen group, and provided that when Cy¹ is

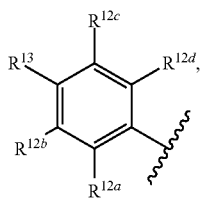

Cy² is

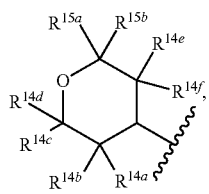

and at least seven of $R^{14a}$, $R^{14b}$, $R^{14c}$, $R^{14d}$, $R^{14e}$, $R^{14f}$, $R^{15a}$, and $R^{15b}$ are hydrogen, then each of $R^{12a}$, $R^{12b}$, $R^{12c}$, and $R^{12d}$ is hydrogen, or a pharmaceutically acceptable salt thereof.

2. The compound of claim 1, wherein each of $R^{1a}$, $R^{1b}$, $R^{1c}$, $R^{1d}$, and $R^{1e}$ is independently selected from hydrogen and halogen.

3. The compound of claim 1, wherein each of $R^{1a}$, $R^{1b}$, $R^{1c}$, $R^{1d}$, and $R^{1e}$ is hydrogen.

4. The compound of claim 1, wherein Cy¹ is a structure represented by a formula:

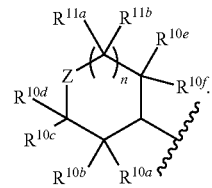

5. The compound of claim 1, wherein Cy¹ is a structure represented by a formula selected from:

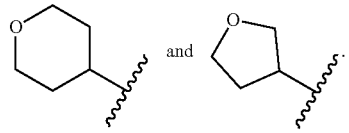

6. The compound of claim 1, wherein Cy¹ is a structure represented by a formula:

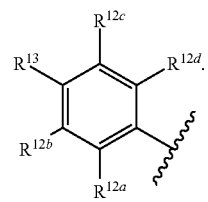

7. The compound of claim 1, wherein Cy² is a structure represented by a formula:

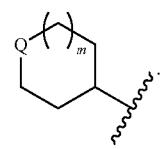

8. The compound of claim 1, wherein Cy² is a structure represented by a formula:

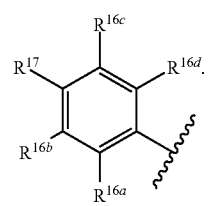

9. The compound of claim 1, wherein the compound has a structure represented by a formula:

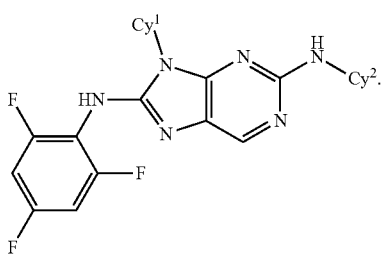

10. The compound of claim 1, wherein the compound has a structure represented by a formula:

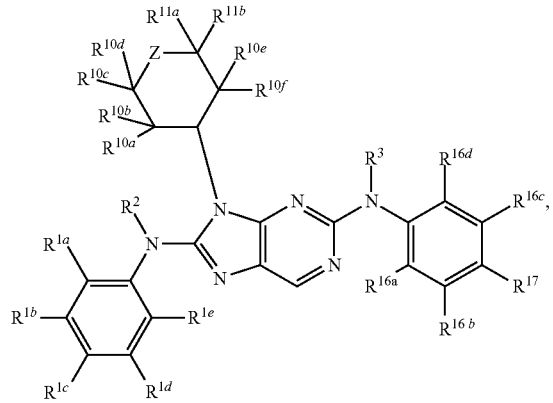

wherein each of $R^{1a}$, $R^{1c}$, and $R^{1e}$ is halogen.

11. The compound of claim 1, wherein the compound has a structure represented by a formula:

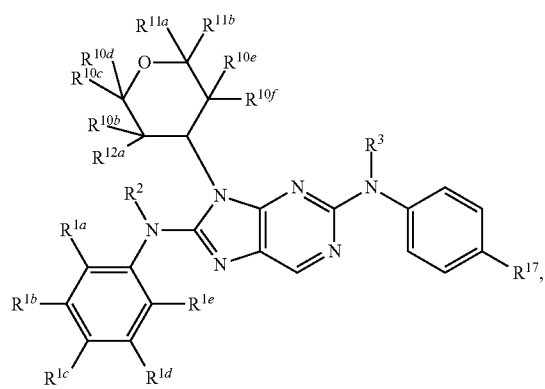

wherein $R^{17}$ is selected from —OH, —NH$_2$, C1-C4 alkoxy, C1-C4 alkylamino, and (C1-C4)(C1-C4) dialkylamino.

12. The compound of claim 1, wherein the compound has a structure represented by a formula:

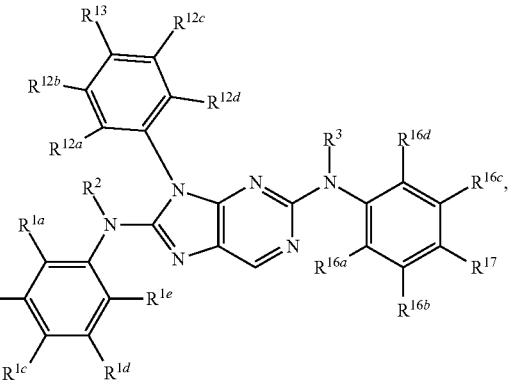

wherein $R^{17}$, when present, is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —CO$^2$H, and —CO$_2$(C1-C4 alkyl).

13. The compound of claim 1, wherein the compound has a structure represented by a formula:

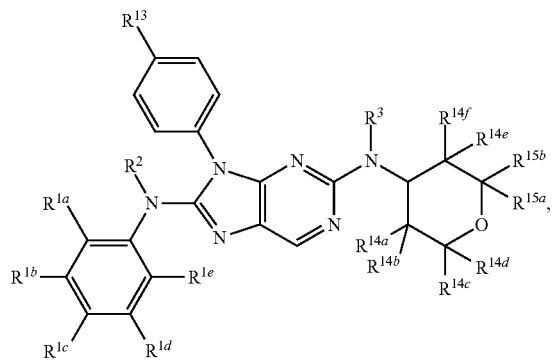

wherein one of $R^{14a}$, $R^{14b}$, $R^{14c}$, $R^{14d}$, $R^{14e}$, $R^{14f}$, $R^{15a}$, and $R^{15b}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein the remaining $R^{14a}$, $R^{14b}$, $R^{14c}$, $R^{14d}$, $R^{14e}$, $R^{14f}$, $R^{15a}$, and $R^{15b}$ groups are hydrogen.

14. The compound of claim 1, wherein the compound is selected from:
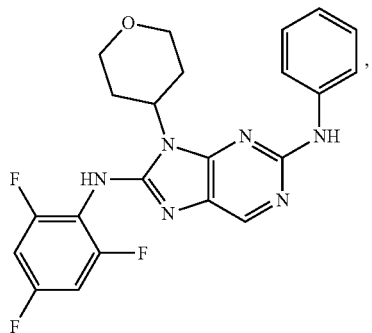
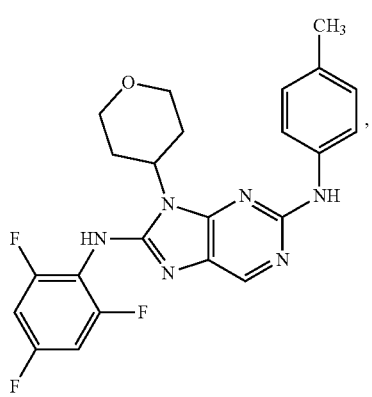
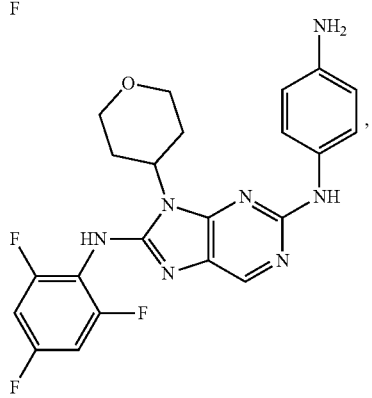
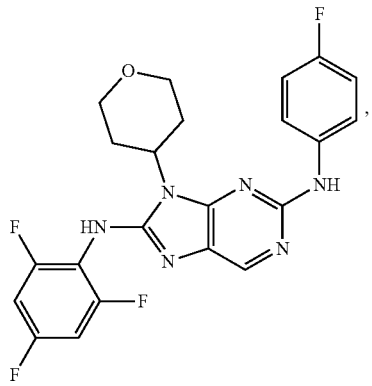
-continued
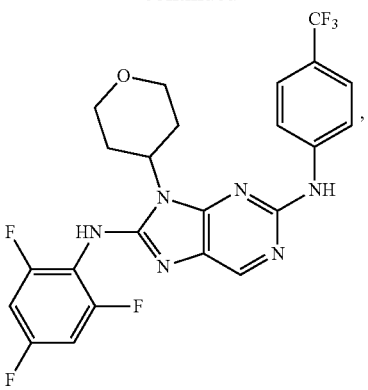
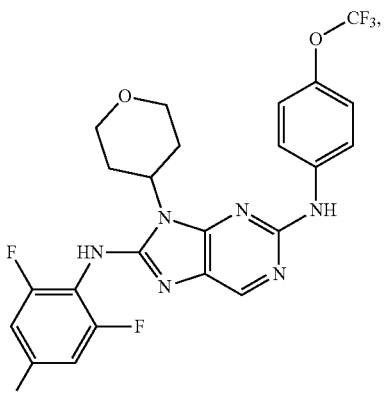
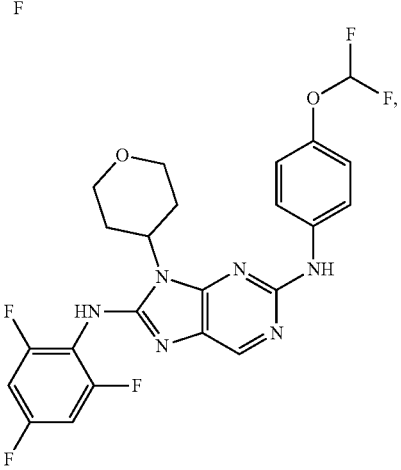
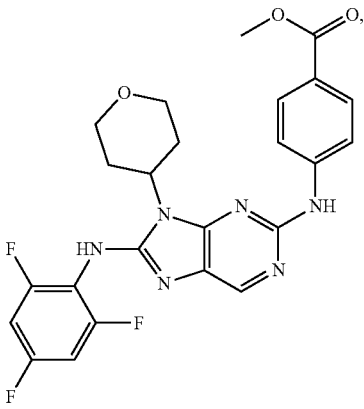

181
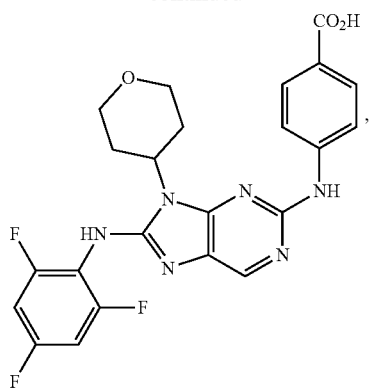
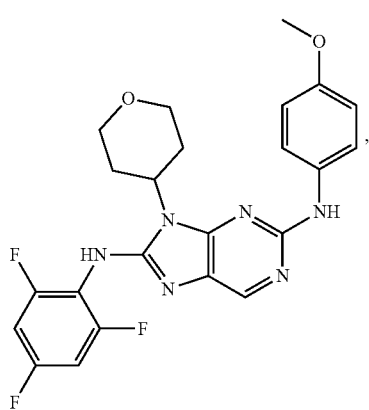
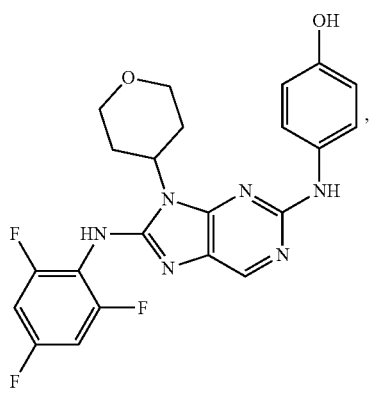
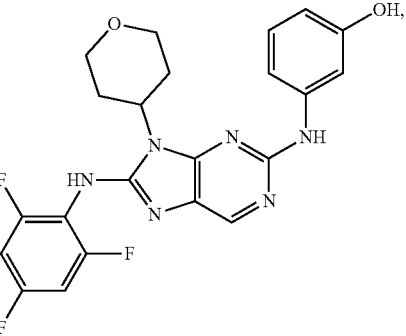
182
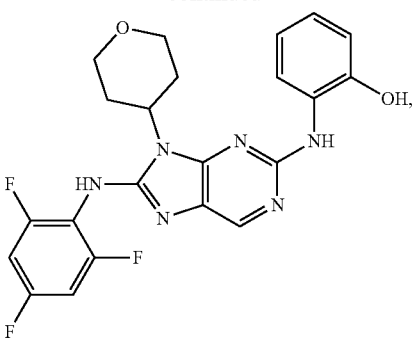
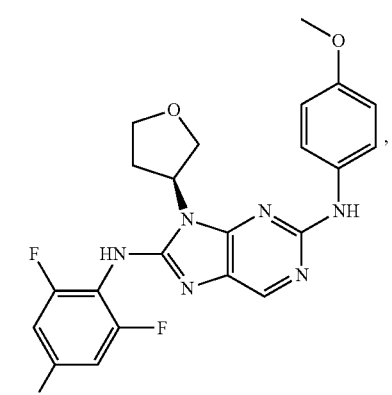
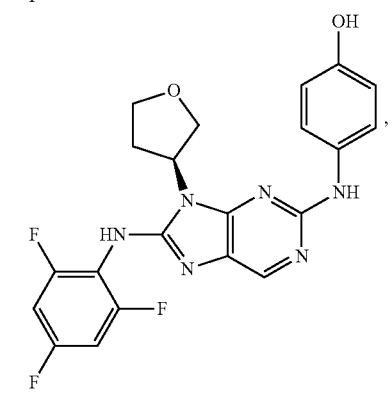
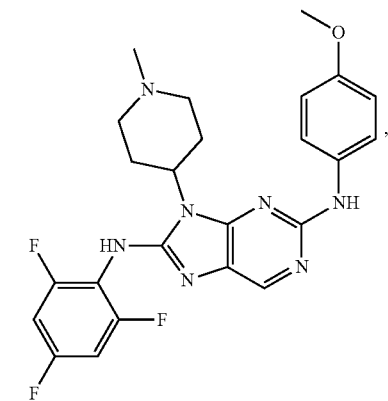

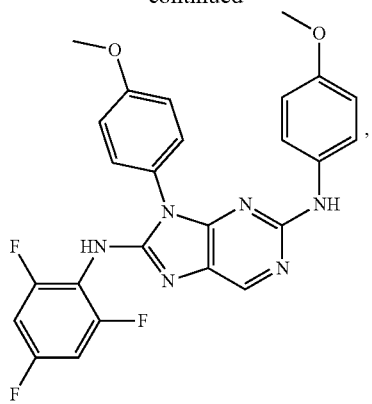
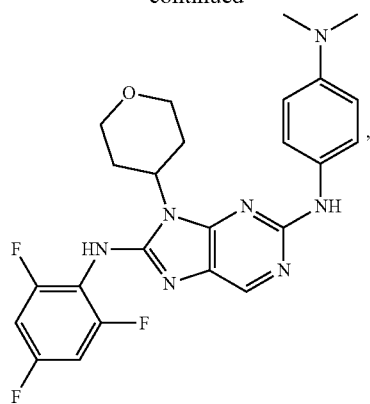
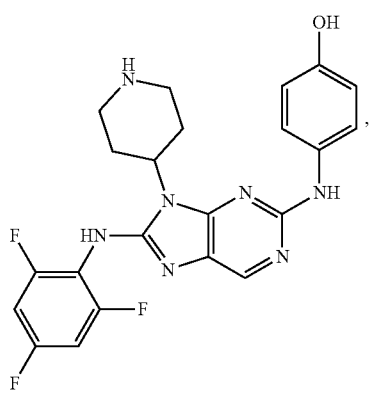
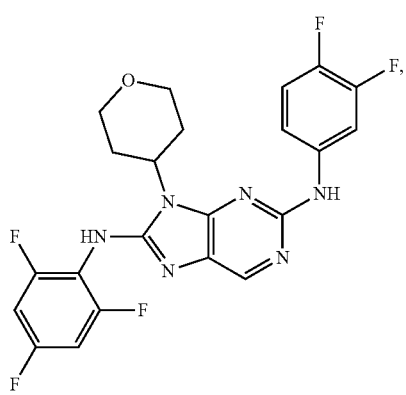
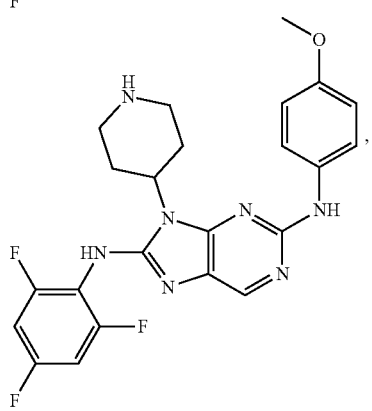
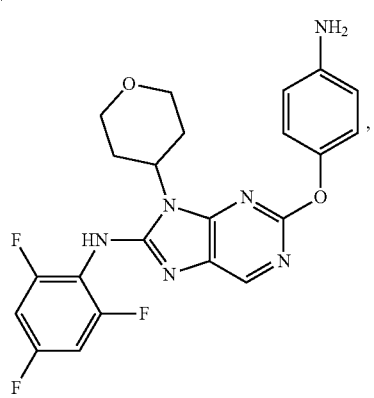
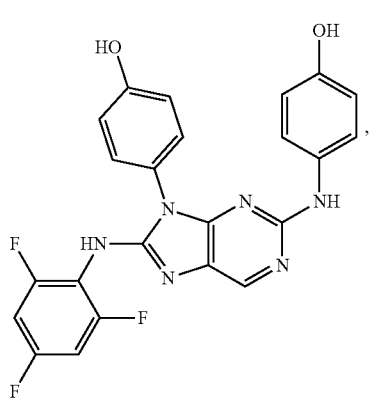
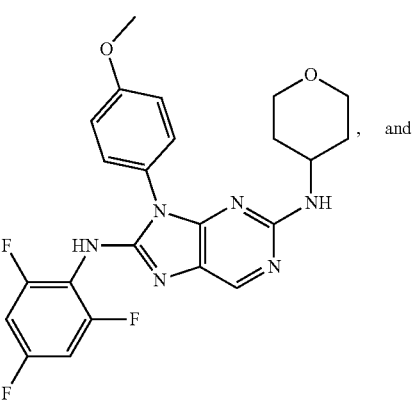, and -continued
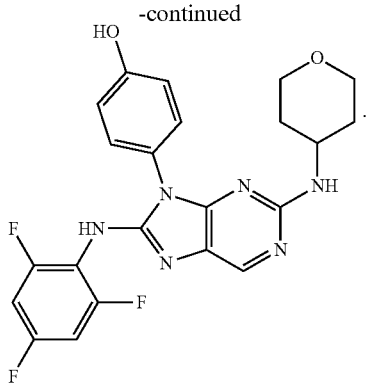
15. A pharmaceutical composition comprising an effective amount of the compound of claim 1, and a pharmaceutically acceptable carrier.
* * * * *